（12) United States Patent
Stranix et al.

(10) Patent No.: US 6,528,532 B1
(45) Date of Patent: Mar. 4, 2003

(54) UREA DERIVATIVES AS HIV ASPARTYL PROTEASE INHIBITORS

(75) Inventors: Brent Richard Stranix, Pointe-Claire (CA); Abderrahim Bouzide, Thornton, CO (US); Gilles Sauvé, Laval (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 10/143,095

(22) Filed: May 13, 2002

(30) Foreign Application Priority Data

Mar. 4, 2002 (CA) ............................................. 2374362

(51) Int. Cl.[7] ........................ A61K 31/44; C07D 401/02
(52) U.S. Cl. ........................ 514/318; 514/326; 514/357; 514/464; 514/602; 514/603; 514/604; 546/194; 546/213; 546/332; 549/438; 560/13; 562/430; 564/86; 564/90
(58) Field of Search ................................ 546/194, 213, 546/332; 549/438; 560/13; 562/430; 564/86, 90; 514/318, 326, 357, 464, 602, 603, 604

(56) References Cited

U.S. PATENT DOCUMENTS 6,455,587 B1 * 9/2002 Bouzide et al. ............. 514/602

OTHER PUBLICATIONS

Dankwardt et al, Bioorganic and Medicinal Chemistry Letters, vol. 12, pp. 1233–1235, Jan. 2002.*

* cited by examiner

*Primary Examiner*—Zinna Northington Davis
(74) *Attorney, Agent, or Firm*—Ronald S. Kosie; Robert Brouillette; Gaetan Prince

(57) ABSTRACT

The present invention provides HIV aspartyl protease inhibitors of the formula:

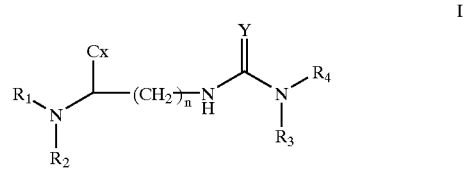

and when the compound of formula I comprises an amino group, pharmaceutically acceptable ammonium salts thereof, wherein n is 3 or 4, Y is O, S, NH or N—CN, wherein Cx may be, for example COOH, or $CH_2OH$, wherein $R_1$ is selected from the group consisting of a benzenesulfonyl group of formula II as defined herein, wherein $R_2$ may be, for example, iso-butyl, or 3-methylbutyl, and wherein $R_3$ and $R_4$ are as defined herein.

57 Claims, No Drawings

UREA DERIVATIVES AS HIV ASPARTYL PROTEASE INHIBITORS

TECHNICAL FIELD OF THE INVENTION

This invention concerns a novel class of urea derivatives possessing aspartyl protease inhibitory properties. It describes the synthetic methodology used to make these urea derivatives from readily available L-lysine analogues and their biological applications. In addition, this invention relates to different pharmaceutical compositions comprising these compounds. The compounds and the pharmaceutical compositions of this invention have been shown to inhibit the activity of HIV aspartyl protease, an enzyme essential for virus maturation and infectivity. The inhibitory property may be advantageously used to provide compounds with antiviral properties against HIV viruses, including the HIV-1 and HIV-2 viruses.

BACKGROUND OF THE INVENTION

HIV, the human immunodeficiency virus, causes AIDS through infection of specialized cells of the immune system carrying CD4 receptors. The HIV retrovirus reproduces in these cells, especially the so-called T-helper cells, and kills them in the process. While the body has the ability to re-generate T-helper cells to some extent, after years of continuous cell destruction by HIV and fighting back by the immune system, the virus eventually emerges as the battle's winner. The progressive destruction of T-helper cells leads to weakening of the immune system which in turn, opens the door to opportunistic pathogens. When this happens, HIV-infected people start to show clinical symptoms. If left unchecked, HIV infection leads to death in a matter of years.

In order to reproduce in infected cells, HIV needs three major enzymes that are carried inside the viral particle. These three enzymes, reverse transcriptase, protease and integrase, thus represent ideal targets for antiviral therapy. Of these, reverse transcriptase has been the first enzyme targeted by the pharmaceutical industry. Inhibitors of the viral protease have been developed more recently and their use as drugs for AIDS treatment began only in 1996.

Although the development of reverse transcriptase and protease inhibitors has improved significantly the survival time and quality of life of HIV-infected patients, their use leads to unwanted side effects, such as anemia, neurotoxicity, bone marrow suppression and lipodystrophy. Most of the currently available anti-protease drugs are large molecules with limited ability to cross the blood-brain barrier. New compounds devoid of these drawbacks are urgently needed to treat HIV infections. In addition, HIV has the ability to develop resistance to the currently available drugs, so new compounds with original structure are desirable to fight these resistant viral strains.

SUMMARY OF THE INVENTION

The present invention provides a novel class of compounds, including their pharmaceutically acceptable derivatives. These compounds have an affinity for aspartyl proteases, in particular, HIV aspartyl protease. Therefore, these compounds are useful as inhibitors of such proteases. These compounds can be used alone or in combination with other therapeutic or prophylactic agents for the treatment or prophylaxis of viral infection.

According to a preferred embodiment, the compounds of this invention are capable of inhibiting HIV viral replication in human cells (e.g., CD4+ T-cells), by inhibiting the ability of HIV aspartyl protease to catalyse the hydrolysis of peptide bonds present in viral Gag and Gag-Pol polyproteins. These novel compounds can thus serve to reduce the production of infectious virions from acutely and chronically infected cells, and can inhibit the initial or further infection of host cells. Accordingly, these compounds are useful as therapeutic and prophylactic agents to treat or prevent infection by HIV-1 and HIV-2, which may result in asymptomatic infection, AIDS-related complex (ARC), acquired immunodeficiency syndrome (AIDS), AIDS-related dementia, or similar diseases of the immune system, and related viruses such as HTLV-I and HTLV-II, and simian immunodeficiency virus.

It is the main objective of this invention to provide a novel class of molecules that are aspartyl protease inhibitors, and particularly, HIV aspartyl protease inhibitors.

The present invention relates to a class of Nε-amino acid substituted L-lysine derivatives (including its lower and higher homologues and analogs) as well as their pharmaceutically acceptable derivatives (e.g., salts).

Accordingly, the present invention in accordance with one aspect thereof provides a compound(s) of formula I

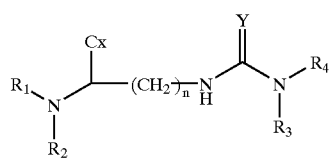

I and when the compound of formula I comprises an amino group, pharmaceutically acceptable ammonium salts thereof, wherein n may be 3, 4 or 5, wherein Y may be O, S, NH or N—CN, wherein Cx may be selected from the group consisting of —COOM, —COOR$_5$, and —CH$_2$OR$_6$ wherein M may be selected from the group consisting of alkali metals (e.g., Na, K, Cs, etc) and alkaline earth metals (e.g., Ca, Mg, etc.), wherein R$_1$ may be a benzenesulfonyl group of formula II

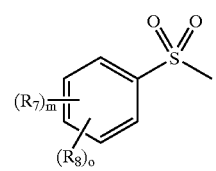

II wherein R$_2$ may be selected from the group consisting of a straight alkyl group of 1 to 6 carbon atoms, a branched alkyl group of 3 to 6 carbon atoms, and a cycloalkylalkyl group having 3 to 6 carbon atoms in the cycloalkyl part thereof and 1 to 3 carbon atoms in the alkyl part thereof, wherein R$_3$ may be selected from the group consisting of H, a straight alkyl group of 1 to 6 carbon atoms, a branched alkyl group of 3 to 6 carbon atoms, a piperonyl group, a phenyl group, a picolyl group selected from the group consisting of a picolyl group selected from the group consisting of

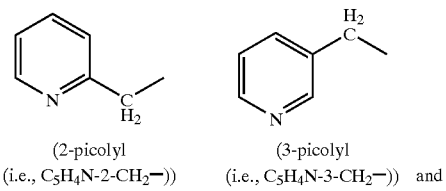
(2-picolyl (i.e., C₅H₄N-2-CH₂—))   (3-picolyl (i.e., C₅H₄N-3-CH₂—))  and

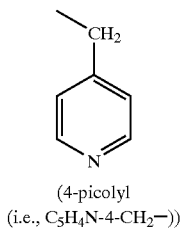
(4-picolyl (i.e., C₅H₄N-4-CH₂—))

a thiophene group selected from the group consisting of

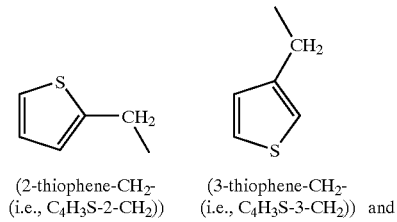
(2-thiophene-CH₂- (i.e., C₄H₃S-2-CH₂))   (3-thiophene-CH₂- (i.e., C₄H₃S-3-CH₂))  and

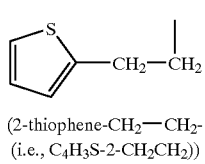
(2-thiophene-CH₂—CH₂- (i.e., C₄H₃S-2-CH₂CH₂))

and a benzyl group of formula III

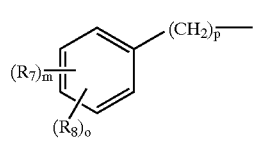

wherein R₄ may be selected from the group consisting of a straight alkyl group of 1 to 6 carbon atoms, a branched alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl, (S)-2-hydroxy-1-indanyl, 1-isoquinolyl, 2-quinolyl, a group of formula IIIa

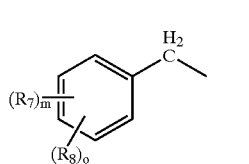

a picolyl group selected from the group consisting of

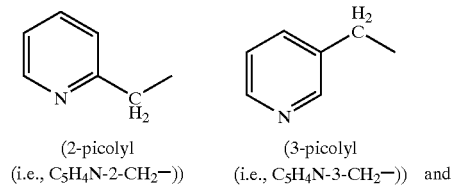
(2-picolyl (i.e., C₅H₄N-2-CH₂—))   (3-picolyl (i.e., C₅H₄N-3-CH₂—))  and

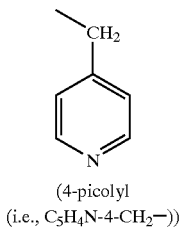
(4-picolyl (i.e., C₅H₄N-4-CH₂—))

a thiophene group selected from the group consisting of

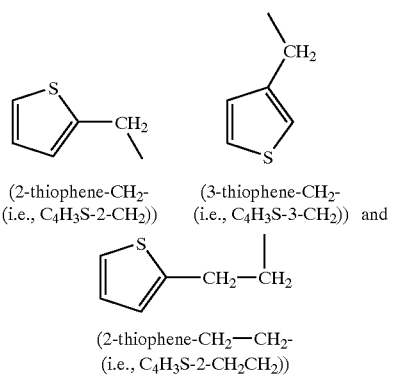
(2-thiophene-CH₂- (i.e., C₄H₃S-2-CH₂))   (3-thiophene-CH₂- (i.e., C₄H₃S-3-CH₂))  and

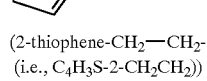
(2-thiophene-CH₂—CH₂- (i.e., C₄H₃S-2-CH₂CH₂))

a group of formula,

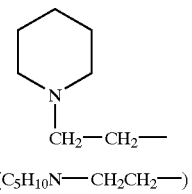
(C₅H₁₀N—CH₂CH₂—)

a group of formula,

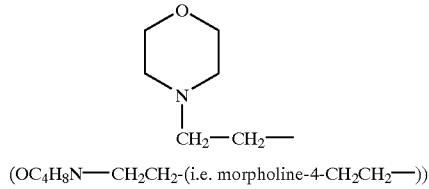
(OC₄H₈N—CH₂CH₂-(i.e. morpholine-4-CH₂CH₂—))

a group of formula,

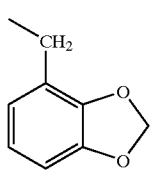

(2,3-methylenedioxybenzyl (i.e., 2,3-(OCH₂O)C₆H₃CH₂—))

a group of formula,

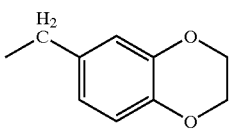

(3,4-ethylenedioxybenzyl (i.e., 3,4-(OCH₂CH₂O)C₆H₃CH₂—))

a group of formula,

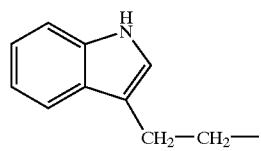

(indole-3-CH₂CH₂—)

a group of formula,

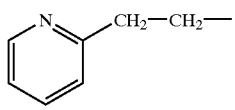

(C₅H₄N-2-CH₂CH₂- (i.e. pyridine-2-ethyl))

a group of formula,

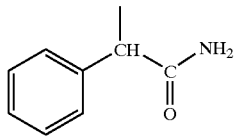

(C₆H₅CH(CONH₂))

a group of formula,

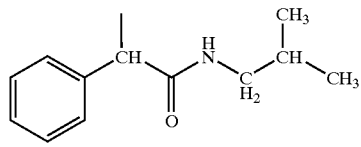

(C₆H₅CH(CONH-i-C₄H₉))

a group of formula,

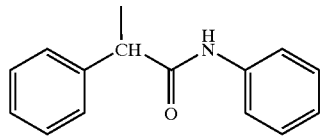

(C₆H₅CH(CONHC₆H₅))

a group of formula,

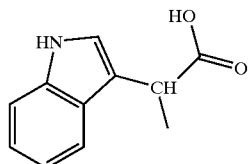

(3-indole-CH₂CH(CO₂H))

a group of formula,

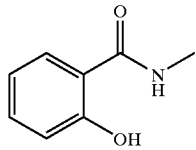

(2-HO—C₆H₄CONH—)

and a group of formula,

(C₅H₄N-4-CONH—)

wherein $R_5$ may be selected from the group consisting of H, a straight alkyl group of 1 to 4 carbon atoms and a branched alkyl group of 3 or 4 carbon atoms, wherein $R_6$ may be selected from the group consisting of H, a straight alkyl group of 1 to 4 carbon atoms and a branched alkyl group of 3 or 4 carbon atoms, wherein $R_7$ and $R_8$, same or different, may be selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$, wherein $R_9$ and $R_{10}$, same or different, may be selected from the group consisting of H, a straight alkyl group of 1 to 4 carbon atoms and a branched alkyl group of 3 or 4 carbon atoms, wherein m may be 0 or 1, wherein o may be 0, 1 or 2, and wherein p may be 0, 1 or 2.

In a further aspect, the present invention provides, a compound(s) of formula IA,

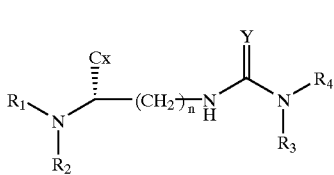

IA and when the compound of formula IA comprises an amino group, pharmaceutically acceptable ammonium salts thereof, wherein n may be 3, 4 or 5, wherein Y may be O, S, NH or N—CN, wherein Cx may be selected from the group consisting of —COOM, —COOR$_5$, and —CH$_2$OR$_6$ wherein M may be selected from the group consisting of alkali metals (e.g., Na, K, Cs, etc) and alkaline earth metals (e.g., Ca, Mg, etc.), wherein R$_1$ may be a benzenesulfonyl group of formula II

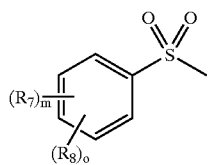

II wherein R$_2$ may be selected from the group consisting of a straight alkyl group of 1 to 6 carbon atoms, a branched alkyl group of 3 to 6 carbon atoms, and a cycloalkylalkyl group having 3 to 6 carbon atoms in the cycloalkyl part thereof and 1 to 3 carbon atoms in the alkyl part thereof, wherein R$_3$ may be selected from the group consisting of H, a straight alkyl group of 1 to 6 carbon atoms, a branched alkyl group of 3 to 6 carbon atoms, a piperonyl group, a phenyl group, a picolyl group selected from the group consisting of

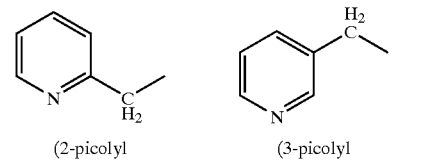

(2-picolyl (i.e., C$_5$H$_4$N-2-CH$_2$—))   (3-picolyl (i.e., C$_5$H$_4$N-3-CH$_2$—))   and

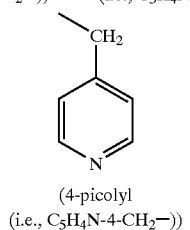

(4-picolyl (i.e., C$_5$H$_4$N-4-CH$_2$—))

a thiophene group selected from the group consisting of

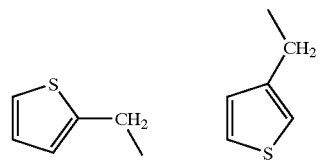

(2-thiophene-CH$_2$- (i.e., C$_4$H$_3$S-2-CH$_2$))   (3-thiophene-CH$_2$- (i.e., C$_4$H$_3$S-3-CH$_2$))   and

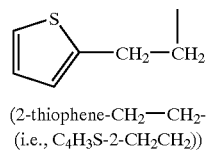

(2-thiophene-CH$_2$—CH$_2$- (i.e., C$_4$H$_3$S-2-CH$_2$CH$_2$))

and a benzyl group of formula III

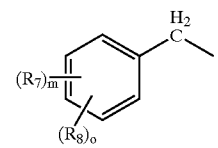

III wherein R$_4$ may be selected from the group consisting of a straight alkyl group of 1 to 6 carbon atoms, a branched alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl, (S)-2-hydroxy-1-indanyl, 1-isoquinolyl, 2-quinolyl, a group of formula IIIa

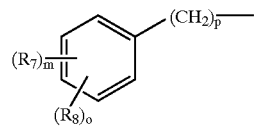

IIIa a picolyl group selected from the group consisting of

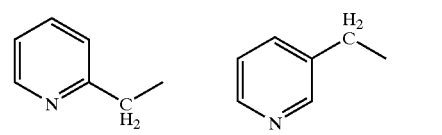

(2-picolyl (i.e., C$_5$H$_4$N-2-CH$_2$—))   (3-picolyl (i.e., C$_5$H$_4$N-3-CH$_2$—))   and

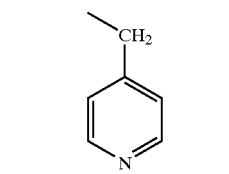

(4-picolyl (i.e., C$_5$H$_4$N-4-CH$_2$—))

a thiophene group selected from the group consisting of (2-thiophene-CH$_2$-
(i.e., C$_4$H$_3$S-2-CH$_2$))

(3-thiophene-CH$_2$-
(i.e., C$_4$H$_3$S-3-CH$_2$)) and (2-thiophene-CH$_2$—CH$_2$-
(i.e., C$_4$H$_3$S-2-CH$_2$CH$_2$))

a group of formula, (C$_5$H$_{10}$N—CH$_2$CH$_2$—)

a group of formula, (OC$_4$H$_8$N—CH$_2$CH$_2$-(i.e. morpholine-4-CH$_2$CH$_2$—))

a group of formula, (2,3-methylenedioxybenzyl (i.e., 2,3-(OCH$_2$O)C$_6$H$_3$CH$_2$—))

a group of formula, (3,4-ethylenedioxybenzyl (i.e., 3,4-(OCH$_2$CH$_2$O)C$_6$H$_3$CH$_2$—))

a group of formula, (indole-3-CH$_2$CH$_2$—)

a group of formula, (C$_5$H$_4$N-2-CH$_2$CH$_2$- (i.e. pyridine-2-ethyl))

a group of fonnula, (C$_6$H$_5$CH(CONH$_2$))

a group of formula, (C$_6$H$_5$CH(CONH-i-C$_4$H$_9$))

a group of formula, (C$_6$H$_5$CH(CONHC$_6$H$_5$))

a group of formula, (3-indole-CH$_2$CH(CO$_2$H))

a group of formula,

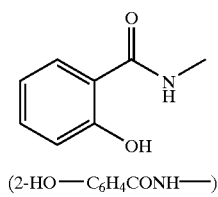

(2-HO—C$_6$H$_4$CONH—)

and a group of formula,

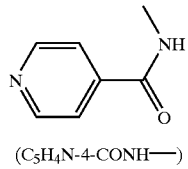

(C$_5$H$_4$N-4-CONH—)

wherein R$_5$ may be selected from the group consisting of H, a straight alkyl group of 1 to 4 carbon atoms and a branched alkyl group of 3 or 4 carbon atoms, wherein R$_6$ may be selected from the group consisting of H, a straight alkyl group of 1 to 4 carbon atoms and a branched alkyl group of 3 or 4 carbon atoms, wherein R$_7$ and R$_8$, same or different, may be selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, wherein R$_9$ and R$_{10}$, same or different, may be selected from the group consisting of H, a straight alkyl group of 1 to 4 carbon atoms, and a branched alkyl group of 3 or 4 carbon atoms, wherein m may be 0 or 1, wherein o may be 0, 1 or 2, and wherein p may be 0, 1 or 2.

More particularly, the present invention provides compounds wherein Cx may be —CO$_2$H, Y may be O and n may be 4.

In accordance with the present invention, R$_2$ may be iso-butyl.

Also in accordance with the present invention, R$_1$ may be selected from the group consisting of 4-CH$_3$C$_6$H$_4$SO$_2$— and 4-NH$_2$C$_6$H$_4$SO$_2$—.

In accordance with the present invention, R$_1$ may be selected from the group consisting of 4-CH$_3$C$_6$H$_4$SO$_2$— and 4-NH$_2$C$_6$H$_4$SO$_2$— while R$_2$ may be iso-butyl.

The present invention also provides compounds wherein Cx may be —CH$_2$OH, Y may be O and n may be 4.

In accordance with the present invention, R$_2$ may be selected from the group consisting of iso-butyl, 2-methylbutyl and 3-methylbutyl.

Also in accordance with the present invention, R$_1$ may be selected from the group consisting of 4-CH$_3$C$_6$H$_4$SO$_2$— and 4-NH$_2$C$_6$H$_4$SO$_2$— while R$_2$ may be iso-butyl.

In accordance with the present invention, R$_1$ may be 4-NH$_2$C$_6$H$_4$SO$_2$— while R$_2$ may be selected from the group consisting of 2-methylbutyl and 3-methylbutyl.

In addition, the present invention provides compounds wherein Cx may be —CO$_2$H, Y may be S and n may be 4.

In accordance with the present invention, R$_1$ may be 4-CH$_3$C$_6$H$_4$SO$_2$— while R$_2$ may be iso-butyl.

Furthermore, the present invention provides compounds wherein Cx may be —CH$_2$OH, Y may be S and n may be 4.

In an additional aspect, the present invention provides a compound(s) of formula Ia

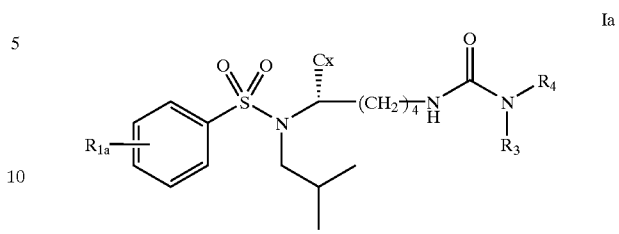

and when the compound of formula Ia comprises an amino group, pharmaceutically acceptable ammonium salts thereof, wherein Cx may be selected from the group consisting of —COOM, —COOH and —CH$_2$OH, wherein M may be selected from the group consisting of alkali metals (e.g., Na, K, Cs, etc) and alkaline earth metals (e.g., Ca, Mg, etc.), wherein R$_{1a}$ may be selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, and wherein R$_3$, R$_4$, R$_9$ and R$_{10}$ may be as defined above.

More particularly, the present invention provides compounds wherein R$_3$ may be a group selected from the group consisting of

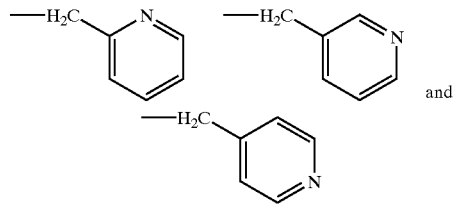

Furthermore, the present invention provides compounds wherein R$_3$ may be a group of formula IV

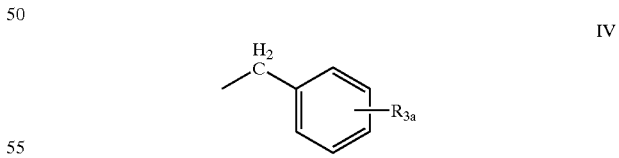

where R$_{3a}$ may be selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH.

In yet a further aspect, the present invention provides a compound(s) of formula Ib

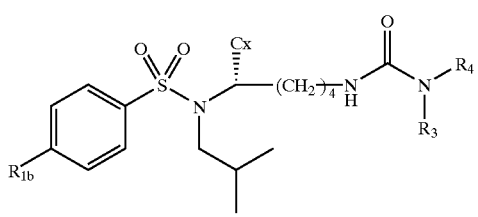

Ib

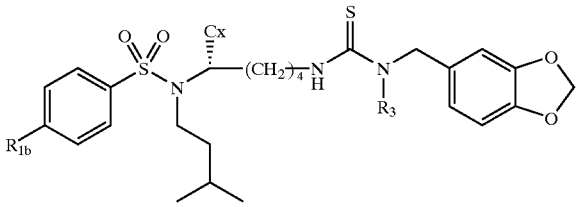

Id and when the compound of formula Ib comprises an amino group, pharmaceutically acceptable ammonium salts thereof, wherein Cx may be selected from the group consisting of —COOM, —COOH and —CH$_2$OH, wherein M may be selected from the group consisting of alkali metals (e.g., Na, K, Cs, etc) and alkaline earth metals (e.g., Ca, Mg, etc.), wherein $R_{1b}$ may be selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, and wherein R$_3$, R$_4$, R$_9$ and R$_{10}$ may be as defined above.

More particularly, the present invention provides compounds wherein Cx may be selected from the group consisting of —COOH and —COOM, and wherein M may be selected from the group consisting of Na, K and Cs.

In addition, the present invention provides compounds wherein Cx may be —CH$_2$OH.

In another aspect, the present invention provide a compound(s) of formula Ic

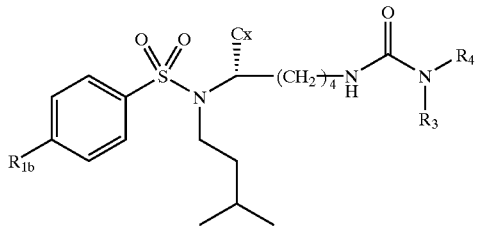

Ic and when the compound of formula Ic comprises an amino group, pharmaceutically acceptable ammonium salts thereof, wherein Cx may be selected from the group consisting of —COOM, —COOH and —CH$_2$OH, wherein M may be selected from the group consisting of alkali metals (e.g., Na, K, Cs, etc) and alkaline earth metals (e.g., Ca, Mg, etc.), wherein $R_{1b}$ may be selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, and wherein R$_3$, R$_4$, R$_9$ and R$_{10}$ may be as defined above.

More particularly, the present invention provides compounds wherein Cx may be —CH$_2$OH.

In yet another aspect, the present invention provides compound(s) of formula Id and when the compound of formula Id comprises an amino group, pharmaceutically acceptable ammonium salts thereof, wherein Cx may be selected from the group consisting of —COOM, —COOH and —CH$_2$OH, wherein M may be selected from the group consisting of alkali metals (e.g., Na, K, Cs, etc) and alkaline earth metals (e.g., Ca, Mg, etc.), wherein $R_{1b}$ may be selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, and wherein R$_3$, R$_4$, R$_9$ and R$_{10}$ may be as defined above.

More particularly, the present invention provides compounds wherein Cx may be —CH$_2$OH.

It is to be understood herein that benzyl groups of formula III encompass, for example, without limitation, groups of formula

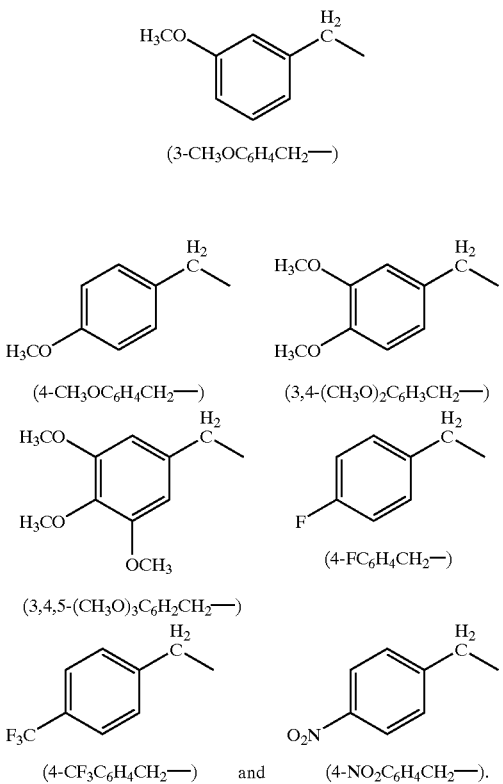

It is also to be understood herein that groups of formula IIIa encompass for example, without limitation, groups of formula,

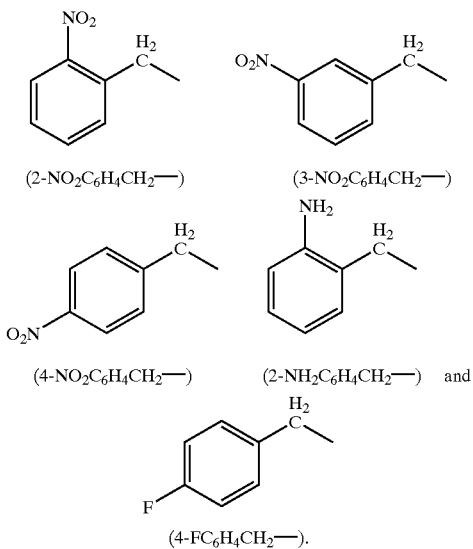

(2-NO₂C₆H₄CH₂—)   (3-NO₂C₆H₄CH₂—)

(4-NO₂C₆H₄CH₂—)   (2-NH₂C₆H₄CH₂—) and (4-FC₆H₄CH₂—).

This invention also provides in a further aspect, pharmaceutical compositions comprising a pharmaceutically acceptable carrier and at least one compound of formula I, IA, Ia, Ib, Ic, and Id as defined herein. The pharmaceutical composition may comprise, for example, a pharmaceutically effective amount of such one or more compounds or as applicable, pharmaceutically acceptable ammonium salts thereof.

The term "pharmaceutically effective amount" refers to an amount effective in treating HIV infection in a patient. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount having an inhibitory effect on HIV (HIV-1 and HIV-2 as well as related viruses (e.g., HTLV-I and HTLV-II, and simian immunodeficiency virus)) infection cycle (e.g., inhibition of replication, reinfection, maturation, budding etc.) and on any organism depending on aspartyl proteases for their life cycle.

In addition, this invention provides pharmaceutical compositions in which these novel compounds of formula I, (as well as of formulae IA, Ia, Ib, Ic and Id) derived from L-lysine or L-lysine derivatives (as well as lower and higher homologues) are used to inhibit aspartyl proteases, including HIV aspartyl protease, thus providing protection against HIV infection.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "prophylactically effective amount" refers to an amount effective in preventing HIV infection in a patient. As used herein, the term "patient" refers to a mammal, including a human.

The terms "pharmaceutically acceptable carrier", "pharmaceutically acceptable adjuvant" and "physiologically acceptable vehicle" refer to a non-toxic carrier or adjuvant that may be administered to a patient, together with a compound of this invention, and which does not destroy the pharmacological activity thereof.

The compounds of this invention include pharmaceutically acceptable derivatives of the compounds of formula I (as well as of formulae IA, Ia, Ib, Ic and Id) and as applicable pharmaceutically acceptable ammonium salts thereof. A "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an antivirally active metabolite or residue thereof.

It is to be understood herein that a "straight alkyl group of 1 to 6 carbon atoms" includes for example, methyl, ethyl, propyl, butyl, pentyl, hexyl.

It is to be understood herein that a "branched alkyl group of 3 to 6 carbon atoms" includes for example, without limitation, iso-butyl, tert-butyl, 2-pentyl, 3-pentyl, etc.

It is to be understood herein, that a "cycloalkyl group having 3 to 6 carbon" includes for example, without limitation, cyclopropyl, cyclobutyl, cyclopentyl, cyclocyclohexyl (i.e., $C_6H_{11}$).

Salts derived from appropriate bases include alkali metal (e.g., sodium), alkaline earth metal (e.g., magnesium), ammonium and N—$(C_{1-4}$ alkyl$)_4^+$ salts.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quatemization of any basic nitrogen containing groups of the compounds disclosed herein. The basic nitrogen can be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

It is to be understood herein, that if a "range", "group of substances" or particular characteristic (e.g., temperature, concentration, time and the like) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example,

- with respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.
- with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;
- and similarly with respect to other parameters such as concentrations, elements, etc. . . .

It is in particular to be understood herein that the compound formulae each include each and every individual compound described thereby as well as each and every possible class or sub-group or sub-class of compounds whether such class or sub-class is defined as positively including particular compounds, as excluding particular compounds or a combination thereof.

It is also to be understood herein that "g" or "gm" is a reference to the gram weight unit and "C", or "° C. " is a reference to the Celsius temperature unit.

first strategy uses an isocyanate (or thioisocyanate) intermediate obtained from a L-lysine derivative which is further reacted with diverse primary and secondary amines to yield the urea (or thiourea) end products. The second methodology uses a solid phase approach in which a L-lysine derivatives (or lysinol derivative) is transformed into various ureas upon reaction 1,1'-carbonyldiimidazole (or 1,1'-thiocarbonyldiimidazole) and a suitable amine synthon. The detailed description of these strategies are presented in schemes 1 to 6 discussed below.

Scheme 1 illustrates a generic example for the preparation of a key L-lysine intermediate IV needed for the synthesis of HIV protease inhibitors according to the first strategy (see schemes 1 and 2, see examples 2 and 18 in the experimental portion of this document).

Note:
a) For scheme 1, $R_1$ represents a benzenesulfonyl group of formula II as defined above,
b) $R_2$ represents an alkyl side chain as defined above (e.g., i-$C_4H_9$ (iso-butyl), 2-methylbutyl, 3-methylbutyl, etc.)

Scheme 1 can be used for the preparation of Nα-isobutyl-Nα-(4-methylbenzenesulfonyl)-L-lysine methyl ester (IVa) and Nα-(4-aminobenzenesulfonyl)-Nα-isobutyl-L-lysine methyl ester (IVb). It proceeds by using commercially available Nε-benzyloxycarbonyl-L-lysine methyl ester hydrochloride (I) as the starting material. Reductive alkylation of derivative I with an appropriate aldehyde and sodium cyanoborohydride provided the derivative II. Then, sulfonation with benzenesulfonyl chloride (or substituted-benzenesulfonyl chloride) in the presence of triethylamine in dichloromethane gave compound III in excellent yields for the two first steps. Removal of the benzyloxycarbonyl group (Z group) by hydrogen gas in presence of 10% Pd/C yielded the free Nε-amino derivative IV quantitatively.

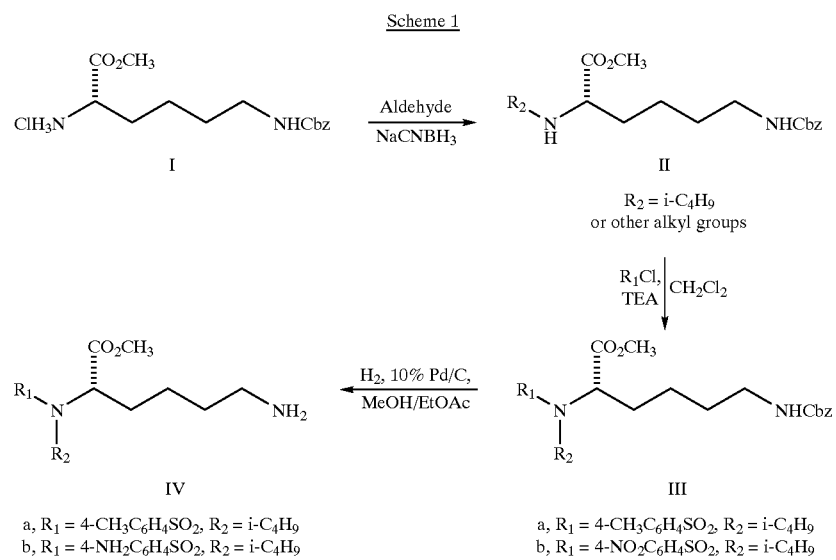

The compounds of this invention are easily prepared using conventional techniques from readily available and inexpensive starting materials. Two different strategies were used to prepared the new urea and thiourea derivatives. The Scheme 2 illustrates a generic example for the preparation of HIV protease inhibitors bearing either a carboxylic function, compound VII, or an alcohol function, compound VIII, on the final product. In other words, this scheme shows the synthesis of a L-lysine urea derivative or a (2S) 2,6-diaminohexanol urea derivative.

Note:
a) For scheme 2, $R_1$ and $R_2$ are as defined in the first aspect of the invention,
b) $R_3$ represents H, a straight alkyl group of 1 to 6 carbon atoms, a branched alkyl group of 3 to 6 carbon atoms, a picolyl group (i.e. 2-, 3-, or 4-picolyl), 2-thiophene-$CH_2$—, 2-thiophene-$CH_2CH_2$—, a piperonyl group a phenyl or a benzyl group of formula III as defined above
c) $R_4$ represents a straight alkyl group of 1 to 6 carbon atoms, a branched alkyl group of 3 to 6 carbon atoms, a cycloalkyl group having 3 to 6 carbon, a group of formula IIIa as defined above, $C_5H_{10}N$—$CH_2CH_2$—, $OC_4H_8N$—$CH_2CH_2$— (i.e. morpholine-4-$CH_2CH_2$—), (i.e. 2-picolyl), $C_5H_4N$-3-$CH_2$— (i.e. 3-picolyl), $C_5H_4N$-4-$CH_2$— (i.e. 4-picolyl), 2-thiophene-$CH_2$—, 2-thiophene-$CH_2CH_2$—, piperonyl, 1-indanyl, (R)-2-hydroxy-1-indanyl, (S)-2-hydroxy-1-indanyl, indole-3-$CH_2CH_2$, $C_5H_4N$-2-$CH_2CH_2$— (i.e. pyridine-2-ethyl), 1-isoquinol, 2-quinolyl, $C_6H_5CH(CONH_2)$, $C_6H_5CH(CONH$-i-$C_4H_9)$, $C_6H_5CH(CONHC_6H_5)$, 3-indole-$CH_2CH$ $(CO_2H)$, 2-HO—$C_6H_4CONH$— or $C_5H_4N$-4-$CONH$—

Treatment of derivative IV with 1,1'-carbonyldiimidazole (or 1,1'-thiocarbonyldiimidazole) provided the intermediate isocyanate (or thioisocyanate) in excellent yields. This intermediate is stable in solution for months. The isocyanate (or thioisocyanate) can be treated with the desired primary or secondary amine to yield derivative VI in good to excellent yield. The final HIV protease inhibitors VII and VIII are easily obtained from the methyl ester VI by hydrolysis with sodium hydroxide in a mixture of THF and methanol giving the acid VII or by reduction with lithium aluminum hydride (LAH) giving the alcohol VIII, both in excellent yields. It is noteworthy that, under basic hydrolysis of VI to produce compound VII, some racemization may occur. However, it is not the case when compound VI is reduced with LAH to give derivative VIII.

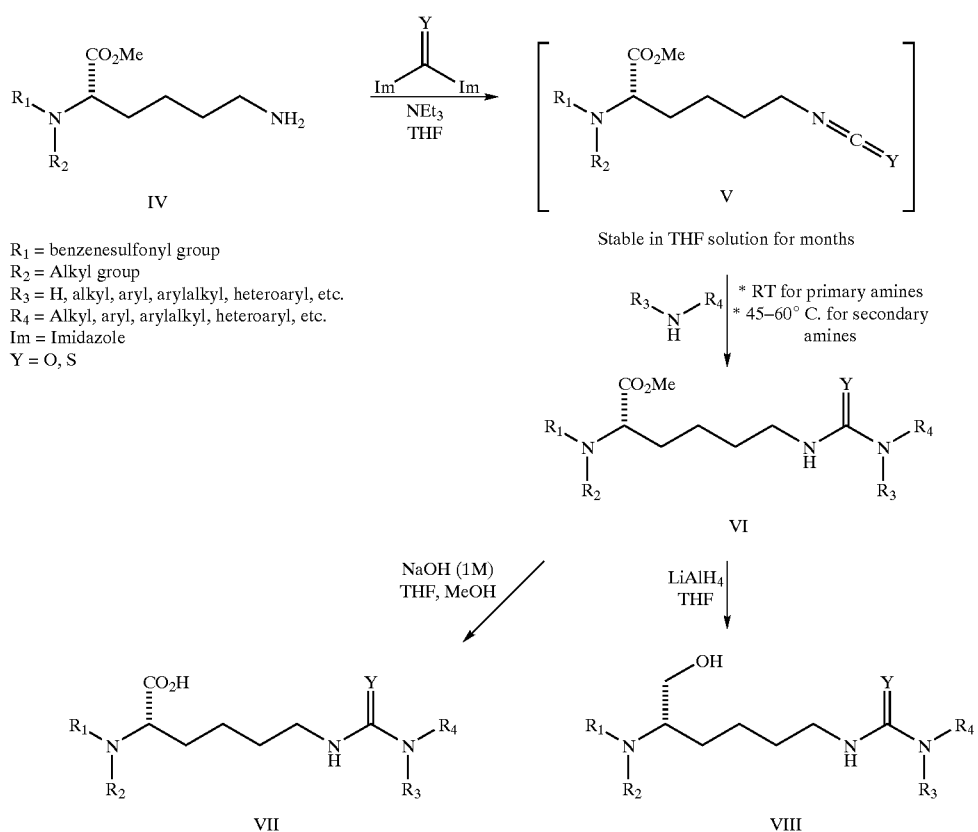

The derivatives VII (or VIII) can be further transformed into a variety of amidine or cyanoamidine of formula IX as shown in scheme 3. These transformations are done under standard reaction conditions. For example, the synthesis of cyanoamidine IX (Y=NCN) can be achieved upon reaction of VII with cyanamide in the presence of mercuric acetate for a period of 3 h. The amidine IX (Y=NH) derivatives is obtained as described above for the cyanamide by replacing cyanamide with ammonia.

Note:
a) For scheme 3, R represents Me or $NH_2$,
b) Cx represents $CO_2H$ or $CH_2OH$,
c) $R_3$ and $R_4$ are as defined above or in scheme 2

Scheme 3

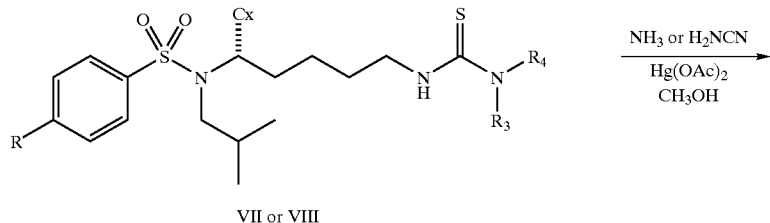

VII or VIII

R = Me, NH$_2$
Cx = CO$_2$H, CH$_2$OH

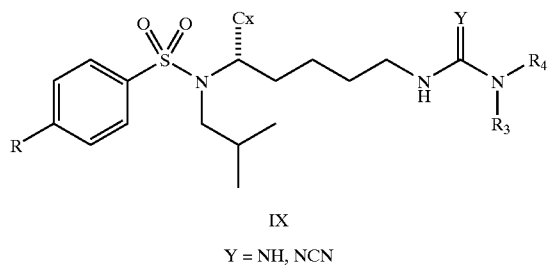

IX

Y = NH, NCN

Scheme 4 illustrates a generic example for the transformation of L-lysine monohydrochloride into a Nα,Nα-disubstituted L-lysine derivatives such as, for example, Nα-isobutyl-Nα-(4-methylbenzenesulfonyl)-L-lysine hydrochloride.

Note:

a) For scheme 4, $R_1$ represents a benzenesulfonyl group of formula II as defined in the first aspect of the invention, b) $R_2$ represents an alkyl side chain as defined above (e.g., i-C$_4$H$_9$ (iso-butyl), 2-methylbutyl, 3-methylbutyl, etc.)

As shown in scheme 4, the Nα,Nα-disubstituted L-lysine derivative XIV was obtained from commercially available L-lysine X in a four-step reaction sequence. This preparation uses the cyclic form of L-lysine in order to manipulate the Nα-amino group without the need for protective groups. First, L-lysine was transformed into L-α-amino-ε-caprolactam XI upon treatment with hydrochloric acid in methanol followed by neutralization with sodium hydroxide. The caprolactam XI is also commercially available. Reductive alkylation of derivative XI with an appropriate aldehyde and NaBH(OAc)$_3$ in dichloroethane led to the Nα-alkylamino-ε-caprolactam XII. Then, sulfonation with an arylsulfonyl chloride (or a substituted-arylsulfonyl chloride) in the presence of triethylamine in dichloromethane gave compound XIII in excellent yields. The Nα,Nα-disubstituted L-lysine derivative XIV was obtained quantitatively by acid hydrolysis of the cyclic amide XIII.

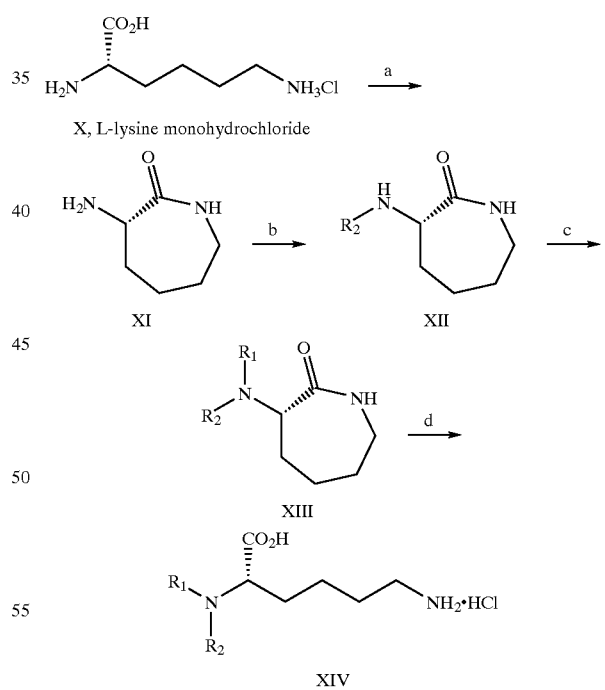

Scheme 4

X, L-lysine monohydrochloride

XI

XII

XIII

XIV

Reagents: a) 1) MeOH/H$^+$ (99.4%); 2) NaOMe, NH$_4$Cl, pH 11.5 (85%); b) Aldehyde, NaBH(OAc)$_3$, DCE; c) arylsulfonyl chloride or substituted-arylsulfonyl chloride; TEA, CH$_2$Cl$_2$, 3 h; d) 6N HCl, reflux, 12 h Scheme 5 and 6 illustrate a second approach for the preparation of an anti-protease derivative using a solid phase methodology in accordance with the present invention. More specifically, scheme 5 presents the method for the synthesis of Nα,Nα-disubstituted-L-lysine derivatives (see example 1) and scheme 6 describes the synthesis of Nα,Nα-disubstituted-L-lysinol derivatives (see example 65). Any suitable solid phase substrate could be used in such preparation (K. Burgess, Solid phase organic synthesis, Wiley-Interscience, 2000).

thiocarbonyldiimidazole) to give the intermediate isocyanate (or thioisocyanate) which is further treated with the an amine (or hydrazide) to yield component XVII. Cleavage of the resin with 95% trifluoroacetic acid (TFA) in $CH_2Cl_2$ leads to the desired L-lysine derivative VII.

Scheme 5

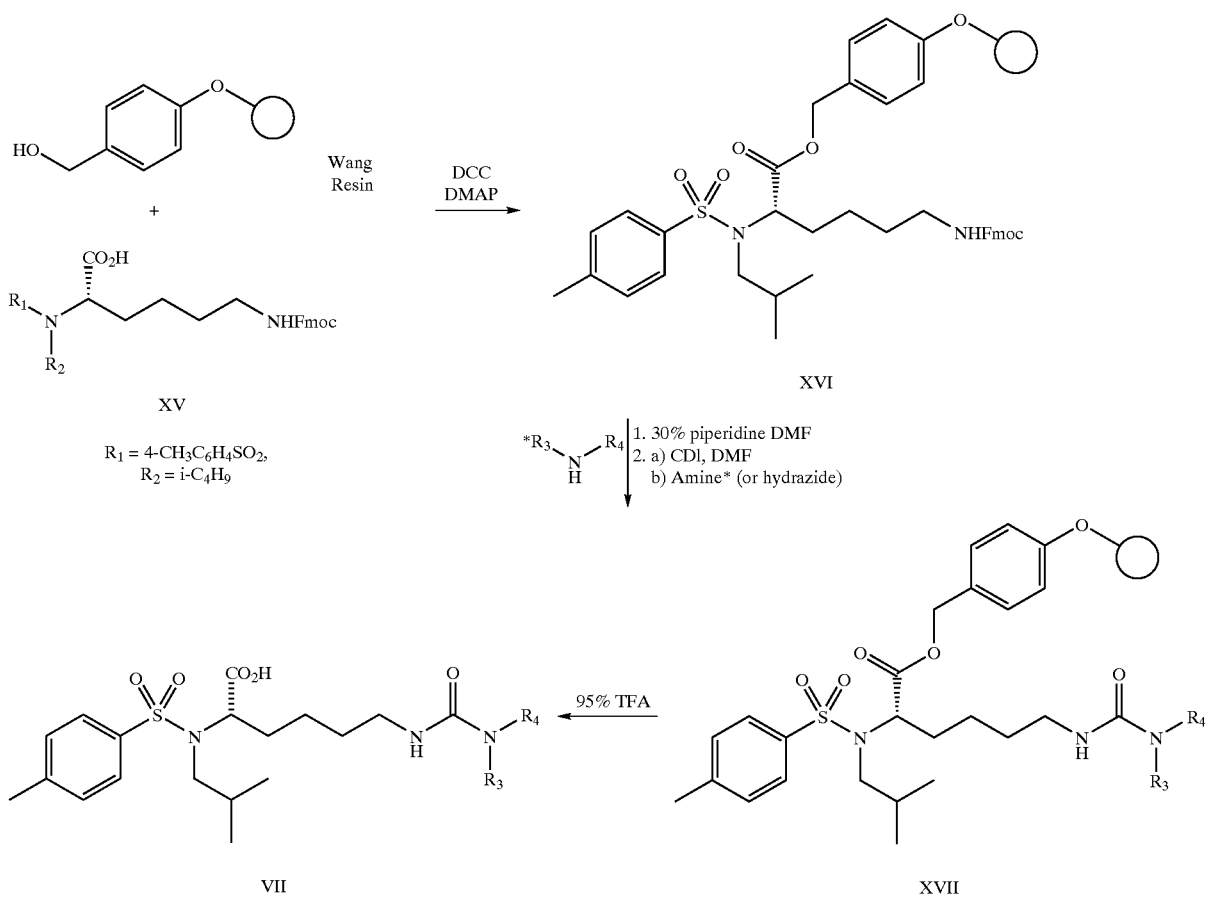

◯ = Any suitable solid phase support could be used, such as, for example, polystyrene (Ps) see K. Burgess, Solid phase organic synthesis, Wiley-Interscience, 2000.
Note:
a) For Scheme 6, $R_1$ is 4-aminobenzenesulfonyl, $R_2$ is iso-butyl,
$R_3$ and $R_4$ are as defined above.

Note:
a) For scheme 5, $R_1$ is 4-methylbenzenesulfonyl, $R_2$ is iso-butyl, $R_3$ and $R_4$ are as defined above.

This process allows the introduction of pharmacophores to a Nα,Nα-disubstituted-L-lysine derivative (such as XV) via the N-terminal function. Thus, in scheme 5, Nα-isobutyl-Nα-(4-methylbenzenesulfonyl)-Nε-(9-fluorenylmethoxycarbonyl)-L-lysine XV is immobilized on a p-benzyloxybenzylalcohol resin (Wang resin) in DMF for a period of 16 h. The resulting component XVI contained 0.28 meq. of L-lysine derivative/g of resin. At this stage, after removal of the Fmoc protective group under standard reaction conditions (30% piperidine in DMF see T. W. Greene and P. G. M. Wuts, Protective groups in Organic Synthesis, 3$^{rd}$ Edition, John Wiley & Sons, Inc. 2000), the resin can be reacted with 1,1'-carbonyldiimidazole (or 1,1'-

This second solid phase approach allows the introduction of pharmacophores to a Nα,Nα-disubstituted-L-lysinol derivative (such as XVIII) via the N-terminal function. Initially, (2S) 2-N-(4-aminobenzenesulfonyl)-2-N-isobutyl-6-N-(9-fluorenylmethoxycarbonyl)-2,6-diaminohexanol XVIII is immobilised on a trityl chloride resin in DCM for a period of 30 minutes. The resulting component IXX contained 0.19 meq. of L-lysinol derivative/g of resin. At this stage, after removal of the Fmoc protective group under standard reaction conditions, the resin can be reacted with 1,1'-carbonyldiimidazole (or 1,1'-thiocarbonyldiimidazole) to give the intermediate isocyanate (or thioisocyanate) which is then further treated with the an amine to yield component XX. Cleavage of the resin with, in this case, 1% trifluoroacetic acid (TFA) in $CH_2Cl_2$ for 3 h leads to the desired L-lysinol urea derivative VIII (i.e. (2S) 2,6-diaminohexanol urea).

Scheme 6

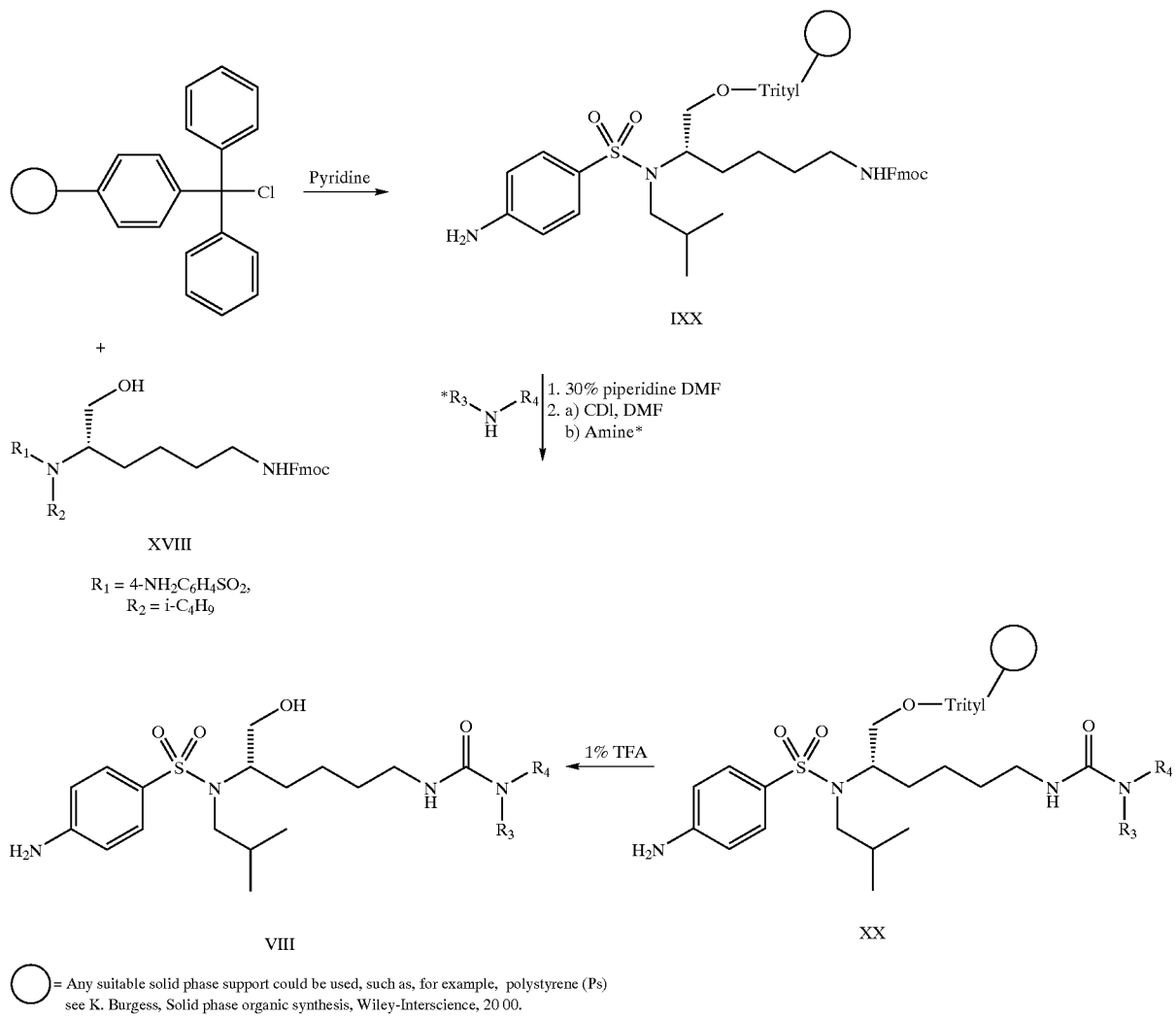

As it can be appreciated by the skilled artisan, the above synthetic schemes are not intended to be a comprehensive list of all means by which the compounds described and claimed in this application may be synthesized. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the novel compounds of the present invention are excellent ligands for aspartyl proteases, particularly HIV-1 protease. Accordingly, these compounds are capable of targeting and inhibiting late stage events in the replication, i.e. the processing of the viral polyproteins by HIV encoded protease. Compounds according to this invention advantageously inhibit the ability of the HIV-1 virus to infect immortalized human T cells over a period of days, as determined by an assay measuring the amount of extracellular p24 antigen—a specific marker of viral replication (see, Meek et al., Nature, 343, pp. 90–92 (1990)).

In addition to their use in the prophylaxis or treatment of HIV or HTLV infection, the compounds according to this invention may also be used as inhibitory or interruptive agents for other viruses which depend on aspartyl proteases, similar to HW or HTLV aspartyl proteases, for obligatory events in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from acutely and chronically infected cells. The compounds of this invention advantageously inhibit aspartyl proteases, thus blocking the ability of aspartyl proteases to catalyse the hydrolysis of peptide bonds.

The compounds of this invention may be employed in a conventional manner for the treatment or prevention of HIV, HTLV, and other viruses, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period of time against viral infections, such as HIV infection. As such, the novel protease inhibitors of this invention can be administered as agents for treating or preventing viral infections, including HIV infection, in a mammal.

The compounds of this invention may be administered to a healthy or HIV-infected patient either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent can be one which targets early events in the viral life cycle, such as attachment to the cell receptor and cell entry, reverse transcription and viral DNA integration into cellular DNA. Antiviral agents targeting such early life cycle events include among others polysulfated polysaccharides, sT4 (soluble CD4) and other compounds which block binding of virus to CD4 receptors on CD4 bearing T-lymphocytes and other CD4(+) cells, or inhibit fusion of the viral envelope with the cytoplasmic membrane, and didanosine (ddI), zalcitabine (ddC), stavudine (d4T), zidovudine (AZT) and lamivudine (3TC) which inhibit reverse transcription. Other anti-retroviral and antiviral drugs may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, other types of drugs may be used to potentiate the effect of the compounds of this invention, such as viral uncoating inhibitors, inhibitors of Tat or Rev trans-activating proteins, antisense molecules or inhibitors of the viral integrase. These compounds may also be co-administered with other inhibitors of HIV aspartyl protease.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce the potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI, ddC, d4T or other reverse transcriptase inhibitors.

Alternatively, the compounds of this invention may also be co-administered with other HIV protease inhibitors such as Ro 31-8959 (Saquinavir; Roche), L-735,524 (Indinavir; Merck), AG-1343 (Nelfinavir; Agouron), A-84538 (Ritonavir; Abbott), ABT-378/r (Lopinavir; Abbott), and VX-478 (Amprenavir; Glaxo) to increase the effect of therapy or prophylaxis against various viral mutants or members of other HIV quasi species.

We prefer administering the compounds of this invention as single agents or in combination with retroviral reverse transcriptase inhibitors, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate sodium, tumor necrosis factor, naltrexone and rEPO) antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar aspartyl proteases for obligatory events in their life cycle. These viruses include, but are not limited to, retroviruses causing AIDS-like diseases such as simian immunodeficiency viruses, HIV-2, HTLV-I and HTLV-II. In addition, the compounds of this invention may also be used to inhibit other aspartyl proteases and, in particular, other human aspartyl proteases including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are amino acid, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene or polyoxypropylene compound, emulsifying wax and water. Alternatively, the pharmaceutical compositions can be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide by an aspartyl protease, or may be derivatized to bind to a stable resin as a tethered substrate for affinity chromatography applications. These and other uses which characterize commercial aspartyl protease inhibitors will be evident to those of ordinary skill in the art.

In the description herein, the following abbreviations are used:

| Abbreviation | Meaning |
| --- | --- |
| Ac | Acetyl |
| AcOH | Acetic acid |

-continued

| Abbreviation | Meaning |
| --- | --- |
| APCI | Atmospheric pressure chemical ionization |
| ARC | AIDS-related complex |
| AIDS | Acquired Immunodeficiency Syndrome |
| AZT | 3-Azido-3-deoxythymine (Zidovudine) |
| i-Bu | iso-Butyl |
| t-Bu | tert-Butyl |
| CAM | Cerium ammonium molybdate |
| Cbz | benzyloxycarbonyl |
| CDI | N,N-carbonyldiimidazole |
| DABCYL | 4-[[4'-(dimethylamino)phenyl]azo]benzoic acid |
| DCC | Dicyclohexylcarbodiimide |
| DCE | Dichloroethane |
| DCM | Dichloromethane |
| DIEA | N,N-Diisopropylethylamine |
| DMAP | N,N-dimethylaminopyridine |
| DMSO | Dimethylsulfoxide |
| DMF | Dimethylformamide |
| DNA | Deoxyribonucleic acid |
| EDANS | 5-[(2'-aminoethyl)amino]naphthalene sulfonic acid |
| EtOAc | Ethyl acetate |
| EtOH | Ethyl alcohol |
| Fmoc | 9-Fluorenylmethoxycarbonyl |
| FRET | Fluorescence resonance energy transfer |
| g | Gram |
| h | hour |
| HIV-1, -2 | Human immunodeficiency virus type 1, type 2 |
| HOBt | 1-Hydroxybenzotriazole |
| HPLC | High performance liquid chromatography |
| HTLV-I, -II | Human T-cell lymphotropic virus type I, type II |
| IL-2 | Interleukin-2 |
| Kg | Kilogram |
| L | Liter |
| LAH | Lithium aluminum hydride |
| LC-MS | Liquid chromatography-mass spectrometry |
| M | Molar |
| MeOH | Methyl alcohol |
| mg | Milligram |
| mp | Melting point |
| min | Minute |
| mol | Mole |
| mL | Milliliter |
| mmol | Millimole |
| MTT | 3-(dimethylthiazol-2-yl)-2,5-diphenyl-2H-tetrazolium bromide |
| nM | Nanomolar |
| rEPO | Recombinant erythropoietin |
| RNA | Ribonucleic acid |
| 3TC | 2',3'-Dideoxy-3-thiacytidine |
| TFA | Trifluoroacetic acid |
| THF | Tetrahydrofuran |

EXAMPLES

This section describes the synthesis of several molecules that are presented in this document. These examples are for the purpose of illustration only and are not to be construed as limiting the scope of the invention in any way. This section presents the detailed synthesis of compounds no. 1 to 110 of this invention.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Preparative HPLC were perform on a Gilson apparatus equipped with a C18 column, a 215 liquid handler module and 15 mL/min capacity head pumps. The HPLC is operated with a Gilson UniPoint System Software. A solvent gradient was used starting from $H_2O/CH_3CN$ (95%:5%) to 100% $CH_3CN$ over 25 min, and 100% $CH_3CN$ for a further 20 min to clean the column.

Unless otherwise indicated, all starting materials were purchased from a commercial source such as Aldrich Co. or Sigma Co.

Melting points (mp) were determined on a Buchi 530 melting point apparatus in capillary tubes and were uncorrected.

Optical rotations ($[\alpha]_D^t$) were measured using a Jasco DIP-370 digital polarimeter at 589 nm (the D line of sodium). Specific rotation is calculated from the observed rotation according to the expression:

$$[\alpha]_D^t = 100\alpha/l \cdot c.$$

where $[\alpha]_D$=specific rotation,

α=observed rotation, c=concentration of the sample in grams per 100 mL of solution, l=the length of the polarimeter tube in decimeters, t=temperature (° C.).

Mass spectra were recorded on a Hewlett Packard LC/MSD 1100 system APCI either in negative mode or positive mode.

Nuclear magnetic resonance (NMR) spectra were recorded on a Bruker AMX 500 equipped with a reversed or QNP probe. Samples were dissolved in deuterochloroform ($CDCl_3$), deuteroacetone (acetone-$d_6$) or deuterodimethylsulfoxide (DMSO-$d_6$) for data acquisition using tetramethylsilane as internal standard. Chemical shifts (δ) are expressed in parts per million (ppm), the coupling constants (J) are expressed in hertz (Hz) whereas multiplicities are denoted as s for singlet, d for doublet, dd for doublet of doublets, t for triplet, q for quartet, m for multiplet, and br s for broad singlet.

GENERAL PROCEDURES

General Procedures for the Preparation of Urea
A. CDI (thio-CDI) Method:

To a stirred solution of Nα-isobutyl-Nα-(4-methylbenzenesulfonyl)-L-lysine methyl ester (see IVa, example 2, step C) (1 mmol) in THF (4 mL) was added 1,1'-carbonyldiimidazole (CDI, 180 mg, 1.1 mmol (or thio-CDI)) followed by triethylamine (278 μL, 2 mmol). The reaction mixture was stirred for 3 h, then amine (commercially available or prepared in one step (see general procedure F)) (1.2–2 mmol) was added in one portion. The reaction was stirred overnight at room temperature for the primary amine or at 45° C. for 15–35 h for the secondary amine. The reaction was diluted with 1N HCl and extracted with ethyl acetate, the organic layer was concentrated and rediluted in THF/MeOH (2 mL/1 mL) and treated with NaOH (1N) (1.2 mmol). The reaction was stirred until complete consumption of the starting material. The reaction mixture was then diluted with diethyl ether (5 mL) and water (5 mL). After stirring vigorously, the aqueous layer was isolated and acidified with 1N HCl until acidic pH (6) and the desired product was isolated in good yields. In some cases a flash chromatography is necessary to eliminate small impurities. N.B.: Precaution must be taken when molecule contain basic site like pyridine.

B. Solid Phase Method with Nα-Isobutyl-Nα-(4-methylbenzenesulfonyl)-Nε-(9-fluorenylmethoxycarbonyl)-L-lysine (XV):

Preparation of Solid Phase Bound Nα-Isobutyl-Nα-(4-methylbenzenesulfonyl)-Nε-(9-fluorenylmethoxycarbonyl)-L-lysine Nα-isobutyl-Nα-(4-methylbenzenesulfonyl)-Nε-(9-fluorenylmethoxycarbonyl)-L-lysine (see XV, 1.51 g, 2.6 mmol) was dissolved in DCM (70 mL) containing DCC (1.5 g). The solution was stirred at room temperature for 8 h and then filtered. The filtrate was added to 5.0 g dried washed Wang resin (0.73 meq/g) to which 150 mg N,N-dimethylaminopyridine (DMAP) was added. The suspension was stirred at room temperature for 12 h. Then, the resin was filtered and washed successively with DCM (100 mL, 2×), 1:1 DCM: MeOH (100 mL, 3×), MeOH (50 mL, 2×) and ether (100 mL). The resin was again swollen in DCM to which acetic anhydride (20 mL) was added. It was left to stand for 3 h and then filtered and washed as above. The resulting resin was dried at room temperature in a dessicator in vacuo. The resulting resin (5.92 g) contained 0.28 meq/g L-lysine derivative.

Deprotection

In a typical experiment, 450 mg (0.125 mmol) of resin-bound Fmoc-lysine was added to a syringe type reaction vessel with Teflon frits and stopcock. The resin was swollen with DCM and washed after 15 min. It was treated with 30% piperidine in DMF (4 mL) and left for 15 min before being successively washed with DMF (5 mL, 2×), DCM (5 mL, 4×), and ether (5 mL, 4×). This process was repeated once.

Coupling

In a typical experiment, 300 mg of CDI was added to the DMF swollen resin-bound lysine and reacted for 10 min. The excess was filtered out and the appropriate amine (or hydrazide) (1.1 molar excess) was dissolved in DMF and added. The coupling reaction was allowed to proceed for 2 h at room temperature. The resin was then washed successively with DCM, MeOH and ether as described above then dried in vacuo.

Cleavage

The dried resin was swollen with DCM, filtered and treated with 95% TFA (4 mL). The resulting mixture was stirred for a period of 3 h. Then, the solution was filtered off and evaporated. The residue was triturated with ether and the pasty solid placed under high vacuum for 4 h. The solid was purified by preparative HPLC to give the final coupled product. The yield of the reactions will be indicated in each specific example.

C. Solid Phase Method with (2S) 2-N-(4-Aminobenzenesulfonyl)-2-N-isobutyl-6-N-(9-fluorenylmethoxycarbonyl)-2,6-diaminohexanol (XVIII):

Preparation of Solid Phase Bound (2S) 2-N-(4-Aminobenzenesulfonyl)-2-N-isobutyl-6-N-(9-fluorenylmethoxycarbonyl)-2,6-diaminohexanol The chlorotrityl resin (16.0 g, 1.3 meq/g) was suspended in a solution of (2S) 2-N-(4-aminobenzenesulfonyl)-2-N-isobutyl-6-N-(9-fluorenylmethoxycarbonyl)-2,6-diaminohexanol (5.0 g) in DCM (200 mL). The mixture was stirred for a few minutes before adding pyridine (5 mL) and leaving the solution to stand for 1 h. Then, the beads were filtered and washed successively with DCM (100 mL, 2×) and ether (100 mL, 3×). After drying, the resulting off white resin (20.62 g) contained 1.0 meq/g of (2S) 2,6-diaminohexanol derivative.

Deprotection

The deprotection of this resin was achieved under the same reaction conditions as for the deprotection of the Wang resin (see general procedure B). In this case, only 100 mg (0.125 mmol) of the resin was used for the deprotection step.

Coupling

The coupling of this resin was done under the same reaction conditions as for the coupling of the Wang resin (see general procedure B). In this case, 200 mg of CDI (or thio-CDI) and 1.1 molar excess of the appropriate amine was used for the coupling step.

Cleavage

The cleavage of this resin was done as for the cleavage of the Wang resin (see general procedure B) using 1% TFA instead of 95% TFA. The resulting solid was purified by preparative HPLC to give the final coupled product. The yield of the reactions will be indicated in each specific example.

D. Catalytic Hydrogenation

A stirred suspension of a nitro derivative (0.1 mmol) and 10% Pd/C (50 mg) in EtOAc (2 mL) was stirred under hydrogen atmospheric pressure for 5–10 min. The reaction has to be followed by TLC until completion. Short reaction time must be used in order to prevent the debenzylation side reaction. The insoluble material was filtered off and the filtrate was concentrated and purified by column chromatography. The yield of the reactions will be indicated in each specific example.

E. General Procedure for the Reduction of Esters with $LiAlH_4$

To a stirred solution of the ester (0.5 mmol) in THF (2 mL) was added at 0° C. $LiAlH_4$ (2 mmol). The mixture was stirred at room temperature for 5–10 min. The reaction has to be closely followed by TLC until completion in order to prevent the reduction of nitro function, when present on the molecule. Afterwards, the reaction was diluted with HCl (1N) and extracted with EtOAc. The organic phase was dried ($MgSO_4$) and concentrated. The crude was purified by column chromatography. The yield of the reactions will be indicated in each specific example.

F. General Method for the Synthesis of Secondary Amines

In a typical experiment, a primary amine (10 mmol) and an aldehyde (10 mmol) are mixed/melted together and diluted with DCE (30 mL). The resulting solution is treated with sodium triacetoxyborohydride (12 mmol) along with acetic acid (1 mL). The mixture is heated to reflux briefly and left to stand at room temperature for 2 h. Afterwards, the solution is extracted with a 5% aqueous NaOH solution (5 mL, 2×) and the DCE is evaporated. The residue is taken up in EtOH (5 mL) and a 6M hydrochloric solution is added (1–2 mL). A White precipitate is formed which is filtered and dried to give the pure secondary amine hydrochloride salt. They are used as such without further purification and characterization.

N.B. Alternatively, some secondary amines were synthesized simply by heating to reflux benzylamine (or substituted benzylamine) (10 mmol) with a substituted benzylchloride (or other halide such as for example piperonylchloride, 6-chloropiperonylchloride, 2-chloromethylthiophene) (10 mmol) in ethanol for a period of 20 to 24 hours. Afterwards, the mixture was concentrated and treated with concentrated hydrochloric acid. The resulting hydrochloride salt was filtered, washed with $Et_2O$ and dried. Typical yields are from 30% to 80%. The final products were used as such without further purification and characterization.

DETAILED DESCRIPTION OF THE INVENTION EXAMPLES

Specific Examples for the Preparation of Derivatives of General Formula I

The following compounds were prepared from either from L-lysine or L-lysine derivatives using the procedures summarized in schemes 1, 2, 3, 4, 5 and 6.

Example 1

Preparation of Nα-Isobutyl-Nα-(4-methylbenzenesulfonyl)-Nε-(2'-phenethylaminocarbonyl)-L-lysine The preparation of the title compound is based on schemes 4 and 5 of this invention.
Step A. Preparation of L-lysine Methyl Ester Dihydrochloride.MeOH (J. Org. Chem. 44, 4841 (1979))

To a stirred suspension of L-lysine monohydrochloride (X) (190.7 g, 1.08 mol) in MeOH (3 L) was added (via a cannula) trimethylsilylchloride (350 mL). The mixture quickly became clear and homogeneous. The solution was stirred at reflux for 3 h and then at room temperature for 2 h. The reaction flask was left overnight in a refrigerator cooled to −75° C. The large crystals obtained were filtered, washed with cold MeOH (100 mL) and dried in vacuo for 24 h at room temperature. L-lysine methyl ester dihydrochloride.MeOH (275.8 g) was obtained in 99.4% yield.

$^1$H NMR (DMSO-$d_6$): δ 1.36 (m, 1H), 1.45 (m, 1H), 1.58 (m, 2H), 1.81 (m, 2H), 2.74 (br s, 2H), 3.11 (s, 3H), 3.72 (s, 3H), 3.94 (t, J=4.0, 1H), 8.12 (br s, 3H), 8.72 (br s, 3H).
Step B. Preparation of L-α-Amino-ε-caprolactam hydrochloride (XI) (J. Org. Chem. 44, 4841 (1979))

Sodium methylate 58.73 g (1 mole) was dissolved in cold MeOH (1 L). About one half of this solution was cannulated into a solution of L-lysine methyl ester dihydrochloride.MeOH (132.5 g, 0.5 mole) in 1 L MeOH. The suspension was allowed to warm and dissolved. The remainder sodium methylate was added with concurrent apparition of NaCl. The mixture was then allowed to reflux for 4 h, after which 5 g of $NH_4Cl$ was added. The solution then sat at RT for 18 h and was filtered through celite. Evaporation of the MeOH resulted in a thick opaque syrup. The excess NaCl was removed by redissolving the mixture in boiling glyme (100 mL, 2×), filtering through celite and evaporating in vacuo. The resulting clear oil was taken up in ethanol and acidified with 1N HCl. Cooling gave a mass of fine white needles which were filtered and dried in vacuo to yield 69.71 g, 85% of the title compound. mp: 301–306° C.

LC-MS: 129.1 $(M+H)^+$, 99% pure. $[α]_D^{20}$=-24.8 (c=3.4, 1N HCl). $^1$H NMR (DMSO-$d_6$): δ 1.17 (q, J=12.6, 1H), 1.45 (q, J=12.6, 1H), 1.58 (q, J=12.6, 1H), 1.71 (d, J=12.6, 1H), 1.86 (d, J=12.6, 1H), 1.94 (d, J=12.6, 1H), 3.03 (m, 1H), 3.15 (m, 1H), 4.03 (d, J=12.6, 1H), 8.12 (br s, 1H), 8.22 (Br s, 3H), $^{13}$C NMR (DMSO-$d_6$): δ 28.2, 29.7, 29.9, 41.6, 53.4, 173.2.

Step C. Preparation of Nα-Isobutyl-L-α-amino-ε-caprolactam (XII)

L-α-amino-ε-caprolactam (XI) (60.0 g, 0.47 mol) was dissolved in dichloroethane (DCE, 100 mL) containing isobutyraldehyde (37.0 g, 0.5 mole) and stirred until the heat evolved was dissipated. Then, DCE (2 L) and AcOH (35 mL) were added to the solution followed by 0.5 mole of powdered $NaBH(OAc)_3$. The slightly turbid mixture was stirred at 60° C. for 2 h, and at room temperature for 12 h. The solution was treated with 1M $K_2CO_3$ (1 L) and stirred for a further 2 h. The DCE layer was dried with $MgSO_4$, filtered and evaporated. The oil thus obtained crystallizes slowly on standing (87 g, 94.5%) and was used without further purification in the next step. mp: 52–54° C. A small sample was converted to the hydrochloride salt by adding the solid to a solution of 1N HCl in 95% EtOH.

$^1$H NMR (CDCl$_3$): δ 0.93 (d, J=6.5, 3H), 0.97 (d, J=6.5, 3H), 1.39 (t, J=9.8, 1H), 1.47 (m, 1H), 1.78–1.65 (m, 2H), 2.00–1.93 (m, 2H), 2.32–2.2 (m, 2H), 2.38 (t, J=9.7, 1H), 3.16 (m, 3H), 6.62 (s, 1H (NH)).
Step D. Preparation of Nα-Isobutyl-Nα-(4-methylbenzenesulfonyl)-L-α-amino-ε-caprolactam (XIII)

Compound XII, prepared in step C of this example (10.0 g, 51 mmol, free base), was dissolved in DCM (100 mL) and treated with diisopropylethylamine (10 mL) followed by freshly recrystallized 4-methylbenzenesulfonyl chloride (11.4 g, 57.3 mmol). The mixture was stirred overnight (TLC shows the reaction to be complete after 2 h). The solution was extracted with 1N HCl and the organic layer was dried and evaporated. Then, the residue was dissolved in boiling CHCl$_3$ (5 mL), diluted with hexanes (200 mL) and placed in the refrigerator for 3 h. The precipitated product was filtered off and air dried giving 15.5 g of pure product. mp: 49–51° C.

$^1$H NMR (CDCl$_3$): δ 0.74 (d, J=6.2, 3H), 0.80 (d, J=6.2, 3H), 1.12 (q, J=8.3, 1H), 1.56–1.73 (m, 4H), 1.84–1.87 (m, 1H), 1.96–1.99 (m, 1H), 2.33 (s, 3H), 2.86–2.89 (m, 1H), 2.97–2.98 (m 1H), 3.1–3.06 (m, 2H), 3.21–3.26 (m, 1H), 4.48 (d, J=10.6, 1H), 5.7 (s, 1H (NH)), 7.29 (d, J=7.7, 2H), 7.59 (d, J=7.7, 2H).
Step E. Preparation of Nα-Isobutyl-Nα-(4-methylbenzenesulfonyl)-L-lysine Hydrochloride (XIV)

A mixture of Nα-isobutyl-Nα-(4-methylbenzenesulfonyl)-L-α-amino-ε-caprolactam (XIII) (13.5 g, 40 mmol), AcOH (4 mL) and 6N HCl (200 mL) was refluxed for 12 h until all solids had disappeared. Afterwards, the solution was evaporated to give 11.0 g, 77% of the hydrochloride salt.

$^1$H NMR (DMSO-$d_6$): δ 0.72 (dd, J=5.8 & 6.4, 6H), 1.13–1.17 (m, 2H), 1.17–1.24 (m 2H), 1.42–1.48 (m, 2H), 2.3 (s, 3H), 2.67 (t, J=7.2, 2H), 2.80–2.91 (m, 2H), 4.13 (t, J=7.2, 1H), 7.22 (d, J=8.5, 2H), 7.64 (d, J=8.5, 2H).
Step F. Preparation of Nα-Isobutyl-Nα-(4-methylbenzenesulfonyl)-Nε-(9-fluorenylmethoxycarbonyl)-L-lysine (XV)

The product of step E of this example (1 mmol) was partially dissolved in $K_2CO_3$ (1M)/THF/CH$_3$CN (4 mL/4 mL/4 mL). To this suspension was added N-(9-fluorenylmethoxycarbonyloxy) succinimide (371 mg, 1.10 mmol). The reaction turned slowly to colourless and was left stirring for 1 h. HCl (1M) was added until acidic pH and the reaction mixture was extracted twice with EtOAc. The combined organic layers were washed with brine, dried over MgSO$_4$ and concentrated. The residue was purified by flash chromatography eluting with a mixture of hexane/EtOAc containing 0.4% AcOH to yield 85% of the title compound.

$^1$H NMR (CDCl$_3$): δ 0.79 (d, J=7.1, 3H), 0.81 (d, J=7.1, 3H), 1.12–1.25 (m, 2H), 1.30–1.40 (m, 2H), 1.42–1.50 (m,

2H), 1.78–1.90 (m, 2H), 2.36 (s, 3H), 2.85 (m, 2H), 2.88 & 3.04 (ABX, J=14.3 & 7.3, 2H), 4.16–4.21 (m, 2H), 4.28 (d, J=7.0, 2H), 7.30–7.42 (m, 6H), 7.60 (m, 4H), 7.88 (d, J=7.5, 2H), 12.69 (br s, 1H).

Step G. Preparation of Nα-Isobutyl-Nα-(4-methylbenzenesulfonyl)-Nε-[N'α-(4-methylbenzenesulfonyl)-glycyl]-L-lysine The title compound was prepared from solid phase bound Nα-isobutyl-Nα-(4-methylbenzenesulfonyl)-Nε-(9-fluorenylmethoxycarbonyl)-L-lysine (step F) as described in general procedure B using commercially available phenylethylamine (1.1 molar excess). The final product was purified by preparative HPLC to yield 30 mg (6.0%) of the desired material.

LC-MS: 502.5 (M–H)⁻, 95% pure.

Example 2

Preparation of Nα-Isobutyl-Nα-(4-methylbenzenesulfonyl)-Nε-(benzylaminocarbonyl)-L-lysine The preparation of the title compound is based on schemes 1 and 2 of this invention.

Step A. Preparation of Nα-Isobutyl-Nε-benzyloxycarbonyl-L-lysine Methyl Ester (II)

To a stirred solution of commercially available Nε-benzyloxycarbonyl-L-lysine methyl ester hydrochloride (I) (9.92 g, 30 mmol), AcOH (6 mL) and NaCNBH$_3$ (33 mmol) in MeOH (250 mL) at 0° C. was added a solution of isobutyraldehyde (3.01 mL, 33 mmol) in MeOH (80 mL). The solution was warmed to room temperature and stirred for 2 h. A saturated solution of K$_2$CO$_3$ (150 mL) was added and the solution was decanted from the solid and coevaporated on vacuo. The residue was partitioned between EtOAc (300 mL) and H$_2$O (200 mL). The organic layer was washed with K$_2$CO$_3$ (1M) and with brine, then dried and concentrated. The crude was used in the next step without further purification.

Step B. Preparation of Nα-Isobutyl-Nα-(4-methylbenzenesulfonyl)-Nε-benzyloxycarbonyl-L-lysine Methyl Ester (IIIa)

To a stirred solution of Nα-isobutyl-Nε-benzyloxycarbonyl-L-lysine methyl ester (II) (336 mg, 1 mmol) in CH$_2$Cl$_2$ (2 mL) was added 4-methylbenzenesulfonyl chloride (286 mg, 1.5 mmol) and triethylamine (174 μL, 1 mmol). The reaction mixture was allowed to stir for 3 days, then it was diluted with 1N HCl and extracted with CH$_2$Cl$_2$. The organic layer was dried (MgSO$_4$) and concentrated. The crude was flash chromatographed using hexane/EtOAc as eluent to obtain the corresponding sulfonamide.

Yield: 71% (steps A and B) ¹H NMR (DMSO-d$_6$): δ 0.84 (d, J=7.2, 3H), 0.86 (d, J=6.3, 3H), 1.30–1.68 (m, 5H), 1.88–2.00 (m, 2H), 2.42 (s, 3H), 2.92 & 3.00 (ABX, J=14.7 & 8.2, 2H), 3.18 (m, 2H), 3.50 (s, 3H), 4.40 (t, J=7.4, 1H), 4.78 (br s, 1H), 5.11 (s, 2H), 7.27–7.71 (m, 9H).

Step C. Preparation of Nα-Isobutyl-Nα-(4-methylbenzenesulfonyl)-L-lysine Methyl Ester (IVa)

Pd/C 10% (120 mg) was added to a solution of the above sulfonamide IIIa (491 mg, 1 mmol) in EtOAc/MeOH (3 mL/3 mL). The suspension was flushed with H$_2$ and maintained under H$_2$ pressure until complete consumption of the starting material. The insoluble material was filtered off, and the filtrate was concentrated under reduced pressure to give the desired amine in quantitative yield. This compound was used without purification in the next step.

Step D. Preparation of Nα-Isobutyl-Nα-(4-methylbenzenesulfonyl)-Nε-(benzylaminocarbonyl)-L-lysine The title compound was prepared from Nα-isobutyl-Nα-(4-methylbenzenesulfonyl)-L-lysine methyl ester (IVa, step C) as described in general procedure A using benzylamine. The final product was obtained in 82% yield.

¹H NMR (DMSO-d$_6$): δ 0.80 (d, J=6.5, 3H), 0.82 (d, J=6.5, 3H), 1.12–1.50 (m, 5H), 1.75–1.95 (m, 2H), 2.37 (s, 3H), 2.85–2.91 (m, 3H), 3.00 (dd, J=14.0 & 7.4, 1H), 4.17 (s, 2H), 4.19 (m, 1H), 5.85 (t, J=5.0, 1H), 6.25 (t, J=5.0, 1H), 7.18–7.35 (m, 5H), 7.37 (d, J=8.4, 2H), 7.67 (d, J=8.4, 2H), 12.70 (br s, 1H).

Example 3

Preparation of Nα-Isobutyl-Nα-(4-methylbenzenesulfonyl)-Nε-[N'-(2-picolyl) aminocarbonyl]-L-lysine The title compound was prepared from Nα-isobutyl-Nα-(4-methylbenzenesulfonyl)-L-lysine methyl ester (IVa) (example 2, step C) as described in general procedure A using 2-picolylamine. The final product was obtained in 32% yield.

¹H NMR (DMSO-d$_6$): δ 0.79 (d, J=6.5, 3H), 0.82 (d, J=6.5, 3H), 1.12–1.50 (m, 5H), 1.75–1.95 (m, 2H), 2.37 (s, 3H), 2.85–2.91 (m, 3H), 3.00 (dd, J=14.0 & 7.4, 1H), 4.17 (s, 2H), 4.19 (m, 1H), 5.85 (t, J=5.0, 1H), 6.25 (t, J=5.0, 1H), 7.18–7.35 (m, 4H), 7.37 (d, J=8.4, 2H), 7.67 (d, J=8.4, 2H), 12.70 (br s, 1H).

Example 4

Preparation of (1S,1'RS) Nα-Isobutyl-Nα-(4-methylbenzenesulfonyl)-Nε-(indanyl-1'-aminocarbonyl)-S-lysine The title product was obtained in 73% yield from Nα-isobutyl-Nα-(4-methylbenzenesulfonyl)-L-lysine methyl ester (IVa) (example 2, step C) utilising general procedure A with 1-aminoindan.

¹H NMR (DMSO-d$_6$): δ 0.79 (d, J=6.5, 3H), 0.82 (d, J=6.5, 3H), 1.15–1.50 (m, 5H), 1.60–1.72 (m, 1H), 1.78–1.95 (m, 2H), 2.40 (s, 3H), 2.75 (m, 1H), 2.80–3.02 (m, 5H), 4.20 (t, J=7.0, 1H), 5.10 (t, J=8.0, 1H), 5.75 (s, 2H), 6.12 (d, J=8.5, 1H), 7.15–7.22 (m, 4H), 7.38 (d, J=7.5, 2H), 7.68 (d, J=7.5, 2H), 12.70 (br s, 1H).

Example 5

Preparation of Nα-Isobutyl-Nα-(4-methylbenzenesulfonyl)-Nε-[2'-(4-hydroxyphenethyl)aminocarbonyl]-L-lysine The title compound was prepared from Nα-isobutyl-Nα-(4-methylbenzenesulfonyl)-L-lysine methyl ester (IVa) (example 2, step C) as described in general procedure A using 4-(2'-aminoethyl)phenol. The final product was obtained in 72% yield.

¹H NMR (DMSO-d$_6$): δ 0.80 (d, J=6.5, 3H), 0.82 (d, J=6.5, 3H), 1.15–1.50 (m, 5H), 1.75–1.95 (m, 2H), 2.37 (s, 3H), 2.52 (t, J=7.0, 2H), 2.85–3.00 (m, 4H), 3.13 (m, 2H), 4.17 (t, J=7.0, 1H), 5.70 (t, J=5.0, 1H), 5.80 (t, J=5.0, 1H), 6.66 (d, J=7.4, 2H), 6.97 (d, J=7.5, 2H), 7.37 (d, J=7.5, 2H), 7.67 (d, J=7.5, 2H), 12.70 (br s, 1H).

Example 6

Preparation of Nα-Isobutyl-Nα-(4-methylbenzenesulfonyl)-Nε-[2'-(3-indolyl) ethylaminocarbonyl]-L-lysine This product was obtained form Nα-isobutyl-Nα-(4-methylbenzenesulfonyl)-L-lysine methyl ester (IVa)

(example 2, step C) as described in general procedure A using 3-(2'-aminoethyl)indole. The final product was obtained in 49% yield.

$^1$H NMR (DMSO-d$_6$): δ 0.80 (d, J=6.5, 3H), 0.82 (d, J=6.5, 3H), 1.12–1.25 (m, 3H), 1.36–1.50 (m, 2H), 1.75–1.95 (m, 2H), 2.37 (s, 3H), 2.88–3.05 (m, 4H), 3.65 (br s, 1H), 4.20 (t, J=7.0 Hz, 1H), 6.95 (t, J=7.4, 1H), 7.07 (t, J=7.4, 1H), 7.14 (s, 1H), 7.33 (d, J=7.8, 1H), 7.37 (d, J=7.6, 2H), 7.60 (d, J=6.8, 1H), 7.68 (d, J=7.6, 2H), 12.70 (br s, 1H).

Example 7

Preparation of Nα-Isobutyl-Nα-(4-methylbenzenesulfonyl)-Nε-[(N'-cyclohexyl-N'-isobutyl)aminocarbonyl]-L-lysine The title product was obtained in 57% yield according the general procedure A using Nα-isobutyl-Nα-(4-methylbenzenesulfonyl)-L-lysine methyl ester (IVa) (example 2, step C) and cyclohexyl-isobutylamine.

$^1$H NMR (DMSO-d$_6$): δ 0.80 (d, J=6.5, 3H), 0.82 (d, J=6.5, 3H), 1.00–1.10 (m, 1H), 1.15 (d, J=7.0, 6H), 1.15–1.52 (m, 9H), 1.66–1.95 (m, 6H), 2.37 (s, 3H), 2.37 (s, 3H), 285–3.00 (m, 4H), 3.20 (m, 1H), 3.62 (m, 1H), 4.20 (t, J=7.0, 1H), 6.80 (t, J=5.5, 1H), 7.35 (d, J=7.5, 2H), 7.68 (d, J=7.5, 2H), 12.70 (br s, 1H).

Example 8

Preparation of Nα-Isobutyl-Nα-(4-methylbenzenesulfonyl)-Nε-[L-phenylalanylamide-N'α-carbonyl]-L-lysine This material was prepared from solid phase bound Nα-isobutyl-Nα-(4-methylbenzenesulfonyl)-Nε-(9-fluorenylmethoxycarbonyl)-L-lysine (example 1, step F) as described in general procedure B using commercially available L-phenylalanine amide (1.1 molar excess). The final product was purified by preparative HPLC to yield 17 mg (25%) of the desired material.

LC-MS: 545.2 (M–H)$^-$, 99% pure. $^1$H NMR (CDCl$_3$): δ 0.83 (d, J=6.9, 6H), 1.08–1.11 (m, 2H), 1.23–1.25 (m, 2H), 1.45–1.52 (m, 1H), 1.89–1.99 (m, 2H), 2.32 (s, 3H), 2.94–3.09 (m, 6H), 4.23 (t, J=5.9, 1H), 4.61 (m, 1H), 7.09–7.26 (m, 7H), 7.73 (d, J=8.1, 2H).

Example 9

Preparation of Nα-Isobutyl-Nα-(4-methylbenzenesulfonyl)-Nε-[D-phenylalanylamide-N'α-carbonyl]-L-lysine The title compound was prepared from solid phase bound Nα-isobutyl-Nα-(4-methylbenzenesulfonyl)-Nε-(9-fluorenylmethoxycarbonyl)-L-lysine (example 1, step F) as described in general procedure B using commercially available D-phenylalanine amide (1.1 molar excess). The final product was purified by preparative HPLC to yield 43 mg (63%) of the desired material.

LC-MS: 545.2 (M–H)$^-$, 95% pure.

Example 10

Preparation of Nα-Isobutyl-Nα-(4-methylbenzenesulfonyl)-Nε-[N$_2$-(2-hydroxybenzoyl)-hydrazino-N$_1$-carbonyl]-L-lysine This compound was prepared from solid phase bound Nα-isobutyl-Nα-(4-methylbenzenesulfonyl)-Nε-(9-fluorenylmethoxycarbonyl)-L-lysine (example 1, step F) as described in general procedure B using commercially available salicyl hydrazide (1.1 molar excess). The final roduct was purified by preparative HPLC to yield 22 mg (33%) of the final product.

LC-MS: 533.2 (M–H)$^-$, 95% pure.

Example 11

Preparation of Nα-Isobutyl-Nα-(4-methylbenzenesulfonyl)-Nε-[N$_2$-(pyridine-4-carbonyl)-hydrazino-N$_1$-carbonyl]-L-lysine The title compound was prepared from solid phase bound Nα-isobutyl-Nα-(4-methylbenzenesulfonyl)-Nε-(9-fluorenylmethoxycarbonyl)-L-lysine (example 1, step F) as described in general procedure B using commercially available isoniazide (1.1 molar excess). The final product was purified by preparative HPLC to yield 21 mg (33%) of the desired material.

LC-MS: 518.2 (M–H)$^-$, 95% pure.

Example 12

Preparation of Nα-Isobutyl-Nα-(4-methylbenzenesulfonyl)-Nε-(L-phenylalanyl-N'-isobutylamide-N'α-carbonyl)-L-lysine Step A. Preparation of L-phenylalanine Isobutylamide A solution of N-tert-butoxycarbonyl-L-phenylalanine (265 mg, 1.0 mmol) dissolved in DMF (3 mL) was treated with HOBt (135 mg, 1.0 mmol), EDAC (191 mg, 1.0 mmol) and stirred for a period of 1 h. Then, isobutylamine (140 mg, 2.0 mmol) was added and the resulting mixture stirred for 12 h. Afterwards, the final product was extracted with EtOAc (3×5 mL) and the combined organic phases were washed with a 5% aqueous solution of citric acid. Evaporation of the organic phase left a thick oil which was treated with TFA (5 mL) for 1 h. The amine was extracted with EtOAc (2×5 mL) and washed with 1 N NaOH (5 mL). The organic phase was dried with Na$_2$SO$_4$, evaporated to yield 80% of the desired material. The crude was used in the next step without purification.

Step B. Preparation of Nα-Isobutyl-Nα-(4-methylbenzenesulfonyl)-Nε-(L-phenylalanyl-N'-isobutylamide-N'α-carbonyl)-L-lysine The title compound was prepared from solid phase bound Nα-isobutyl-Nα-(4-methylbenzenesulfonyl)-Nε-(9-fluorenylmethoxycarbonyl)-L-lysine (example 1, step F) as described in general procedure B using L-phenylalanine isobutylamide (1.1 molar excess, step A). The final product was purified by preparative HPLC to yield 52 mg (69%) of the desired material.

LC-MS: 601.8 (M–H)$^-$, 98% pure.

Example 13

Preparation of Nα-Isobutyl-Nα-(4-methylbenzenesulfonyl)-Nε-(L-phenylalanyl-N'-phenylamide-N'α-carbonyl)-L-lysine Step A. Preparation of L-phenylalanine Anilide This compound was prepared as described above for the preparation of L-phenylalanine isobutylamide (example 12, step A) using aniline instead of isobutylamine. The desired material was obtained in 60% yield. The crude was used in the next step without purification.

Step B. Preparation of Nα-isobutyl-Nα-(4-methylbenzenesulfonyl)-Nε-(L-phenylalanyl-N'-phenylamide-N'α-carbonyl)-L-lysine This material was prepared from solid phase bound Nα-isobutyl-Nα-(4-methylbenzenesulfonyl)-Nε-(9-fluorenylmethoxycarbonyl)-L-lysine (example 1, step F) as described in general procedure B using L-phenylalanine anilide (1.1 molar excess, step A). The final product was purified by preparative HPLC to yield 50 mg (64%) of the final product.

LC-MS: 621.8 (M–H)⁻, 98% pure.

Example 14

Preparation of (1S,1'RS) Nα-Isobutyl-Nα-(4-methylbenzenesulfonyl)-Nε-(indanyl-1'-aminothiocarbonyl)-S-lysine This product was obtained form Nα-isobutyl-Nα-(4-methylbenzenesulfonyl)-L-lysine methyl ester (IVa) (example 2, step C) as described in general procedure A using 1,1'-thiocarbonyldiimidazole instead of 1,1'-carbonyldiimidazole and 1-aminoindan. The final product was obtained in 84% yield.

$^1$H NMR (DMSO-d$_6$): δ 0.80 (d, J=6.5, 3H), 0.82 (d, J=6.5, 3H), 1.12–1.25 (m, 3H), 1.36–1.50 (m, 2H), 1.75–1.95 (m, 2H), 2.38 (s, 3H), 2.47 (m, 1H), 2.78 (m, 1H), 2.90 (m, 1H), 2.91 & 2.97 (ABX, J=14.0 & 7.0, 2H), 4.21 (t, J=7.3, 1H), 5.80 (br s, 1H, 7.15–7.30 (m, 5H), 7.38 (d, J=7.5, 2H), 7.62 (d, J=7.5, 1H), 7.68 (d, J=7.5, 2H), 12.70 (br s, 1H).

Example 15

Preparation of Nα-Isobutyl-Nα-(4-methylbenzenesulfonyl)-Nε-[2'-(3-(indolyl)ethylaminothiocarbonyl)]-L-lysine This product was obtained form Nα-isobutyl-Nα-(4-methylbenzenesulfonyl)-L-lysine methyl ester (IVa) (example 2, step C) as described in example 6 following general procedure A with 1,1'-thiocarbonyldiimidazole instead of 1,1'-carbonyldiimidazole and 3-(2'-aminoethyl)indole. The final product was obtained in 42% yield.

$^1$H NMR (DMSO-d$_6$): δ 0.80 (d, J=6.5, 3H), 0.82 (d, J=6.5, 3H), 1.12–1.25 (m, 3H), 1.36–1.50 (m, 2H), 1.75–1.95 (m, 2H), 2.37 (s, 3H), 2.88–3.05 (m, 4H), 3.65 (br s, 1H), 4.20 (t, J=7.0 Hz, 1H), 6.95 (t, J=7.4, 1H), 7.07 (t, J=7.4, 1H), 7.14 (s, 1H), 7.33 (d, J=7.8, 1H), 7.37 (d, J=7.6, 2H), 7.60 (d, J=6.8, 1H), 7.68 (d, J=7.6, 2H), 12.70 (br s, 1H).

Example 16

Preparation of Nα-Isobutyl-Nα-(4-methylbenzenesulfonyl)-Nε-benzylaminothiocarbonyl-L-lysine This thiourea was prepared in the same manner as for the urea (general procedure A), by replacing 1,1'-carbonyldiimidazole with 1,1'-thiocarbonyldiimidazole and by using benzylamine. The final product was obtained in 77% yield.

$^1$H NMR (DMSO-d$_6$): δ 0.79 (d, J=6.5, 3H), 0.82 (d, J=6.5, 3H), 1.20 (m, 2H), 1.38–1.52 (m, 3H), 1.80–1.90 (m, 2H), 2.38 (s, 3H), 2.90 & 2.95 (ABX, J=14.0 & 7.0, 2H), 3.45 (s, 3H), 4.30 (t, J=7.0 Hz, 1H), 4.65 (br s, 1H), 7.20–7.32 (m, 5H), 7.40 (d, J=7.5, 2H), 7.45 (br s, 1H), 7.66 (d, J=7.5, 2H), 7.78 (br s, 1H).

Example 17

Preparation of Nα-Isobutyl-Nα-(4-methylbenzenesulfonyl)-Nε-[2'-(1-pyperidinyl)ethylaminocarbonyl]-L-lysine Following general procedure A with N-(2-aminoethyl)piperidine the title compound was obtained in 34% yield.

$^1$H NMR (DMSO-d$_6$): δ 0.79 (d, J=6.2, 3H), 0.82 (d, J=6.5, 3H), 1.15–1.52 (m, 8H), 1.70 (m, 5H), 1.72–1.90 (m, 2H), 2.37 (s, 3H), 2.88–3.00 (m, 8H), 3.10 (br s, 1H), 3.25–3.40 (m, 4H), 4.18 (t, J=7.3, 1H), 6.19 (t, J=5.0, 1H), 6.30 (m, 1H), 7.40 (d, J=7.5, 2H), 7.68 (d, J=7.5, 2H).

Example 18

Preparation of Nα-(4-Aminobenzenesulfonyl)-Nα-isobutyl-Nε-benzylaminocarbonyl-L-lysine The preparation of this compound is based on schemes 1 and 2 of this invention.

Step A. Preparation of Nα-Isobutyl-Nα-(4-nitrobenzenesulfonyl)-Nε-benzyloxycarbonyl-L-lysine methyl ester (IIIb)

This product was prepared following the procedure described for the preparation of Nα-isobutyl-Nα-(4-methylbenzenesulfonyl)-Nε-benzyloxycarbonyl-L-lysine methyl ester (IIIa) (example 2, step B) using 4-nitrobenzenesulfonyl chloride instead of 4-methylbenzenesulfonyl chloride. The yield of this reaction was 42%.

$^1$H NMR (CDCl$_3$): δ 0.83 (d, J=6.6, 3H), 0.86 (d, J=6.5, 3H), 1.35–1.69 (m, 5H), 1.68–2.00 (m, 2H), 2.90 and 3.04 (ABX, J=14.5, 7.5, 2H), 3.18 (m, 2H), 3.49 (s, 3H), 4.45 (t, J=6.0, 1H), 4.83 (s, 1H), 5.10 (s, 2H), 7.30–7.40 (m, 5H), 8.00 (d, J=8.5, 2H), 8.33 (d, J=8.5, 2H).

Step B. Preparation of Nα-(4-Aminobenzenesulfonyl)-Nα-isobutyl-L-lysine Methyl Ester (IVb)

The title compound was obtained by catalytic hydrogenation of Nα-isobutyl-Nα-(4-nitrobenzenesulfonyl)-Nε-benzyloxycarbonyl-L-lysine methyl ester (IIIb, step A) as described for the preparation of Nα-isobutyl-Nα-(4-methylbenzenesulfonyl)-L-lysine methyl ester (IIIa, example 2, step C). This compound was used without purification in the next step.

Step C. Preparation of Nα-(4-Aminobenzenesulfonyl)-Nα-isobutyl-Nε-benzylaminocarbonyl-L-lysine The title compound was prepared from Nα-(4-aminobenzenesulfonyl)-Nα-isobutyl-L-lysine methyl ester (IVb, step B) as described in general procedure A using benzylamine. The final product was obtained in 73% yield.

$^1$H NMR (DMSO-d$_6$): δ 0.80 (d, J=6.5, 3H), 0.82 (d, J=6.5, 3H), 1.12–1.50 (m, 5H), 1.75–1.95 (m, 2H), 2.85–2.91 (m, 3H), 2.98–3.02 (m, 1H), 4.10 (m, 1H), 4.20 (s, 2H), 5.90 (s, 2H), 6.20 (t, J=5.0, 1H), 6.60 (d, J=7.5, 2H), 7.10–7.40 (m, 7H), 12.70 (br s, 1H).

Example 19

Preparation of Nα-Isobutyl-Nα-(4-methylbenzenesulfonyl)-Nε-[(2'-pyridyl)ethylaminocarbonyl]-L-lysine Methyl Ester The title compound was prepared from Nα-isobutyl-Nε-(4-methylbenzenesulfonyl)-L-lysine methyl ester (IVa) (example 2, step C) as described in general procedure A using 2-(2-aminoethyl)pyridine. The product was isolated as the ester i.e. without being hydrolysed.

The final product was obtained in 71% yield. $^1$H NMR (DMSO-d$_6$): δ 0.78 (d, J=6.5, 3H), 0.81 (d, J=6.5, 3H), 1.12–1.50 (m, 5H), 1.75–1.90 (m, 2H), 2.38 (s, 3H), 2.88–3.00 (m, 4H), 3.44 (s, 3H), 4.30 (m, 4H), 6.10 (t, J=5.0, 1H), 6.40 (t, J=5.0, 1H), 7.20 (m, 2H), 7.40 (d, J=7.5, 2H), 7.65 (d, J=7.5, 2H), 7.75 (t, J=6.5, 1H), 8.47 (d, J=5.5, 1H).

Example 20

Preparation of Nα-Isobutyl-Nα-(4-methylbenzenesulfonyl)-Nε-(1'-isoquinolylaminocarbonyl)-L-lysine This product was obtained in 23% yield according the general procedure A using Nα-isobutyl-Nα-(4-methylbenzenesulfonyl)-L-lysine methyl ester (IVa) (example 2, step C) and 1-aminoisoquinoline.

$^1$H NMR (DMSO-d$_6$): δ 0.76 (d, J=6.5, 3H), 0.82 (d, J=6.5, 3H), 1.12–1.50 (m, 5H), 1.75–1.95 (m, 2H), 2.37 (s, 3H), 2.75–3.00 (m, 4H), 3.50 (s, 2H), 4.10 (t, J=7.0, 1H), 4.18 (m, 1H), 7.00–7.60 (m, 10H), 12.70 (br s, 1H).

Example 21

Preparation of Nα-Isobutyl-Nα-(4-methylbenzenesulfonyl)-Nε-(phenethylaminocarbonyl)-L-lysine The title product was obtained in 63% yield according the general procedure A using Nα-isobutyl-Nα-(4-methylbenzenesulfonyl)-L-lysine methyl ester (IVa) (example 2, step C) and 2-phenylethylamine.

$^1$H NMR (DMSO-d$_6$): δ 0.80 (d, J=6.5, 3H), 0.82 (d, J=6.5, 3H), 1.15–1.50 (m, 5H), 1.75–1.95 (m, 2H), 2.37 (s, 3H), 2.52 (t, J=7.0, 2H), 2.85–3.00 (m, 4H), 3.13 (m, 2H), 4.17 (t, J=7.0, 1H), 5.70 (t, J=5.0, 1H), 5.80 (t, J=5.0, 1H), 7.18–7.35 (m, 5H), 7.37 (d, J=8.4, 2H), 7.67 (d, J=8.4, 2H), 12.70 (br s, 1H).

Example 22

Preparation of (1S,1'R,2'S) Nα-Isobutyl-Nα-(4-methylbenzenesulfonyl)-Nε-(cis-2'-hydroxyindanyl-1'-aminocarbonyl)-S-lysine The title compound was prepared from Nα-Isobutyl-Nα-(4-methylbenzenesulfonyl)-L-lysine methyl ester (IVa) (example 2, step C) as described in general procedure A using (1R,2S)-(+)-cis-1-amino-2-indanol. The final product was obtained in 63% yield.

$^1$H NMR (DMSO-d$_6$): δ 0.80 (d, J=6.5, 3H), 0.82 (d, J=6.5, 3H), 1.15–1.50 (m, 5H), 1.78–1.95 (m, 2H), 2.37 (s, 3H), 2.74 (d, J=15, 1H), 2.90–3.05 (m, 5H), 4.20 (t, J=7.0, 1H), 4.35 (t, J=5.0, 1H), 5.00 (m, 1H), 6.00 (d, J=8.5, 1H), 6.25 (t, J=5.0, 1H), 7.12–7.22 (m, 4H), 7.38 (d, J=7.5, 2H), 7.70 (d, J=7.5, 2H), 12.70 (br s, 1H).

Example 23

Preparation of (1S,1'S,2'R) Nα-Isobutyl-Nα-(4-methylbenzenesulfonyl)-Nε-(cis-2'-hydroxyindanyl-1'-aminocarbonyl)-S-lysine The title compound was prepared from Nα-isobutyl-Nα-(4-methylbenzenesulfonyl)-L-lysine methyl ester (IVa) (example 2, step C) as described in general procedure A using (1S,2R)-(–)-cis-1-amino-2-indanol. The final product was obtained in 63% yield.

$^1$H NMR (DMSO-d$_6$): δ 0.80 (d, J=6.5, 3H), 0.82 (d, J=6.5, 3H), 1.15–1.50 (m, 5H), 1.78–1.95 (m, 2H), 2.37 (s, 3H), 2.74 (d, J=15, 1H), 2.90–3.05 (m, 5H), 4.20 (t, J=7.0, 1H), 4.35 (t, J=5.0, 1H), 5.00 (m, 1H), 6.00 (d, J=8.5, 1H), 6.25 (t, J=5.0, 1H), 7.12–7.22 (m, 4H), 7.38 (d, J=7.5, 2H), 7.70 (d, J=7.5, 2H), 12.70 (br s, 1H).

Example 24

Preparation of (1S,1'R) Nα-Isobutyl-Nα-(4-methylbenzenesulfonyl)-Nε-(indanyl-1'-aminocarbonyl)-S-lysine The title product was obtained in 73% yield from Nα-isobutyl-Nα-(4-methylbenzenesulfonyl)-L-lysine methyl ester (IVa) (example 2, step C) utilising general procedure A with (R)-(–)-1-aminoindan.

$^1$H NMR (DMSO-d$_6$): δ 0.79 (d, J=6.5, 3H), 0.82 (d, J=6.5, 3H), 1.15–1.50 (m, 5H), 1.60–1.72 (m, 1H), 1.78–1.95 (m, 2H), 2.40 (s, 3H), 2.75 (m, 1H), 2.80–3.02 (m, 5H), 4.20 (t, J=7.0, 1H), 5.10 (t, J=8.0, 1H), 5.75 (s, 2H), 6.12 (d, J=8.5, 1H), 7.15–7.22 (m, 4H), 7.38 (d, J=7.5, 2H), 7.68 (d, J=7.5, 2H), 12.70 (br s, 1H).

Example 25

Preparation of (1S,1'S) Nα-Isobutyl-Nα-(4-methylbenzenesulfonyl)-Nε-(indanyl-1'-aminocarbonyl)-S-lysine This product was obtained in 81% yield from Nα-obutyl-Nα-(4-methylbenzenesulfonyl)-L-lysine methyl ester (IVa) (example 2, step C) utilising general procedure A with (S)-(+)-1-aminoindan.

$^1$H NMR (DMSO-d$_6$): δ 0.79 (d, J=6.5, 3H), 0.82 (d, J=6.5, 3H), 1.15–1.50 (m, 5H), 1.60–1.72 (m, 1H), 1.78–1.95 (m, 2H), 2.40 (s, 3H), 2.75 (m, 1H), 2.80–3.02 (m, 5H), 4.20 (t, J=7.0, 1H), 5.10 (t, J=8.0, 1H), 5.75 (s, 2H), 6.12 (d, J=8.5, 1H), 7.15–7.22 (m, 4H), 7.38 (d, J=7.5, 2H), 7.68 (d, J=7.5, 2H), 12.70 (br s, 1H).

Example 26

Preparation of (1R,1'S) Nα-Isobutyl-Nα-(4-methylbenzenesulfonyl)-Nε-(indanyl-1'-aminocarbonyl)-R-lysine Step A. Preparation of Nα-Isobutyl-Nα-(4-methylbenzenesulfonyl)-D-lysine Methyl Ester The title compound was obtained using the same procedure used for the preparation of the epimer; Nα-isobutyl-Nα-(4-methylbenzenesulfonyl)-L-lysine methyl ester as described in example 2, steps A, B and C. Its $^1$H NMR is identical to that of compound IVa.

Step B. Preparation of (1R,1'S) Nα-Isobutyl-Nα-(4-methylbenzenesulfonyl)-Nε-(indanyl-1'-aminocarbonyl)-R-lysine The product was prepared according to general procedure A with (S)-(+)-1-aminoindan. The desired material was obtained in 70% yield. Its $^1$H NMR is identical to the product of example 25.

$^1$H NMR (DMSO-d$_6$): δ 0.79 (d, J=6.5, 3H), 0.82 (d, J=6.5, 3H), 1.15–1.50 (m, 5H), 1.60–1.72 (m, 1H), 1.78–1.95 (m, 2H), 2.40 (s, 3H), 2.75 (m, 1H), 2.80–3.02 (m, 5H), 4.20 (t, J=7.0, 1H), 5.10 (t, J=8.0, 1H), 5.75 (s, 2H), 6.12 (d, J=8.5, 1H), 7.15–7.22 (m, 4H), 7.38 (d, J=7.5, 2H), 7.68 (d, J=7.5, 2H), 12.70 (br s, 1H).

Example 27

Preparation of (1R,1'R) Nα-Isobutyl-Nα-(4-methylbenzenesulfonyl)-Nε-(indanyl-1'-aminocarbonyl)-R-lysine This product was obtained in 66% yield from Nα-isobutyl-Nα-(4-methylbenzenesulfonyl)-R-lysine methyl ester (IVa) (example 2, step C) utilising general procedure A with (S)-(+)-1-aminoindan. Its ¹H NMR is identical to the product of example 27.

¹H NMR (DMSO-d₆): δ 0.79 (d, J=6.5, 3H), 0.82 (d, J=6.5, 3H), 1.15–1.50 (m, 5H), 1.60–1.72 (m, 1H), 1.78–1.95 (m, 2H), 2.40 (s, 3H), 2.75 (m, 1H), 2.80–3.02 (m, 5H), 1.60–7.0, 1H), 5.10 (t, J=8.0, 1H), 5.75 (s, 2H), 6.12 (d, J=8.5, 1H), 7.15–7.22 (m, 4H), 7.38 (d, J=7.5, 2H), 7.68 (d, J=7.5, 2H), 12.70 (br s, 1H).

Example 28

Preparation of Nα-Isobutyl-Nα-(4-methylbenzenesulfonyl)-Nε-(benzylaminocarbonyl-N-cyanoamidine)-L-lysine The preparation of this product is based on scheme 3 of this invention.

The title compound was prepared from Nα-isobutyl-Nα-(4-methylbenzenesulfonyl)-Nε-benzylaminothiocarbonyl-L-lysine (product of example 16) as described for the preparation of Nα-isobutyl-Nα-(4-methylbenzenesulfonyl)-Nε-[2'-(3-indolyl)ethylaminocarbonyl-N-cyanoamidine]-L-lysine described below (see example 29). The final product was obtained in 53% yield.

¹H NMR (DMSO-d₆): δ 0.79 (d, J=6.5, 3H), 0.82 (d, J=6.5, 3H), 1.12–1.50 (m, 5H), 1.75–1.95 (m, 2H), 2.37 (s, 3H), 2.87–3.00 (m, 4H), 4.15–4.20 (m, 3H), 5.87 (t, J=5.6, 1H), 6.25 (t, J=5.6, 1H), 7.19–7.32 (m, 5H), 7.38 (d, J=7.5, 2H), 7.68 (d, J=7.5, 2H), 12.70 (br s, 1H).

Example 29

Preparation of Nα-Isobutyl-Nα-(4-methylbenzenesulfonyl)-Nε-[2'-(3-indolyl)ethylaminocarbonyl-N-cyanoamidine]-L-lysine To a stirred solution of the thiourea (Nα-isobutyl-Nα-(4-methylbenzenesulfonyl)-Nε-[2'-(3-(indolyl)ethylaminothiocarbonyl)-L-lysine, example 15, 56 mg, 0.1 mmol) in MeOH (2 mL) was added cyanamide (8 mg, 0.2 mmol). The mixture was stirred for 5 min, then mercuric acetate (48 mg, 0.15 mmol) was added. The reaction was stirred for 3 h, then was diluted with saturated NH₄Cl and extracted with EtOAc. The organic layer was washed with brine, then concentrated and the crude was purified by column chromatography to yield the desired product (42%).

¹H NMR (DMSO-d₆): δ 0.80 (d, J=6.5, 3H), 0.82 (d, J=6.5, 3H), 1.12–1.50 (m, 6H), 1.75–1.95 (m, 2H), 2.37 (s, 3H), 2.78 (t, J=7.0, 2H), 2.85–3.00 (m, 4H), 3.28 (m, 2H), 4.18 (t, J=7.0, 1H), 5.80 (m, 2H), 6.58 (s, 1H), 6.95 (t, J=7.6, 1H), 7.06 (t, J=7.6, 1H), 7.11 (s, 1H), 7.80 (d, J=7.5, 1H), 7.38 (d, J=7.5, 2H), 7.52 (d, J=7.5, 1H), 7.68 (d, J=7.5, 2H), 10.80 (s, 1H), 12.70 (br s, 1H).

Example 30

Preparation of Nα-Isobutyl-Nα-(4-methylbenzenesulfonyl)-Nω-benzyl-DL-homoarginine Step A. Preparation of Nα-Isobutyl-Nα-(4-methylbenzenesulfonyl)-Nω)-benzyl-DL-homoarginine Methyl Ester To Nα-isobutyl-Nα-(4-methylbenzenesulfonyl)-Nε-benzylaminothiocarbonyl-L-lysine methyl ester (methyl ester of the product of example 16) (100 mg, 0.2 mmol) in MeOH (3 mL) was added saturated ammonia (3 mL) and mercuric acetate (76 mg, 0.24 mmol). The reaction was stirred for 30 min, then filtered on a celite pad with MeOH (7 mL), concentrated and the crude was purified by column chromatography to yield 66% of the pure methyl ester gaunidine.

¹H NMR (DMSO-d₆): δ 0.79 (d, J=6.5, 3H), 0.81 (d, J=6.5, 3H), 1.12–1.50 (m, 5H), 1.75–1.95 (m, 2H), 2.37 (s, 3H), 2.90 & 2.97 (ABX, J=14.0 & 7.0, 2H), 3.10 (m, 2H), 3.42 (s, 3H), 4.30 (t, J=7.5, 1H), 4.42 (d, J=5.7, 2H), 7.30–7.40 (m, 7H), 7.45 (s, 1H), 7.68 (d, J=7.5, 2H), 7.90 (br s, 1H).

Saponification of the methyl ester above as usual (see in general example A) led to the desired acid in 48% yield.

¹H NMR (DMSO-d₆): δ 0.74 (d, J=7.0, 3H), 0.79 (d, J=7.0, 3H), 1.12–1.45 (m, 5H), 1.75–2.00 (m, 2H), 2.29 (s, 3H), 2.85–3.08 (m, 4H), 4.00 (t, J=5.5, 1H), 4.30 (m, 2H), 7.18–7.40 (m, 9H), 7.70 (d, J=7.6, 2H), 7.50–7.80 (br s, 1H).

Example 31

Preparation of Nα-Isobutyl-Nα-(4-methylbenzenesulfonyl)-Nε-[(N'-benzyl-N'-phenethyl)aminocarbonyl]-L-lysine The title compound was prepared from Nα-isobutyl-Nα-(4-methylbenzenesulfonyl)-L-lysine methyl ester (IVa) (example 2, step C) as described in general procedure A using N-benzyl-2-phenethylamine. The final product was obtained in 78% yield.

¹H NMR (DMSO-d₆): δ 0.80 (d, J=6.5, 3H), 0.82 (d, J=6.5, 3H), 1.15–1.50 (m, 5H), 1.75–1.95 (m, 2H), 2.37 (s, 3H), 2.70 (t, J=7.0, 2H), 2.88–3.00 (m, 4H), 4.18 (m, 1H), 4.38 (s, 2H), 6.35 (t, J=5.5, 1H), 7.15–7.40 (m, 12H), 7.66 (d, J=7.5, 2H), 12.70 (br s, 1H).

Example 32

Preparation of Nα-Isobutyl-Nα-(4-methylbenzenesulfonyl)-Nε-(N',N'-dibenzylaminocarbonyl)-L-lysine This product was obtained form Nα-isobutyl-Nα-(4-methylbenzenesulfonyl)-L-lysine methyl ester (IVa) (example 2, step C) as described in general procedure A using dibenzylamine. The final product was obtained in 65% yield.

¹H NMR (DMSO-d₆): δ 0.80 (d, J=6.5, 3H), 0.82 (d, J=6.5, 3H), 1.10 (m, 2H), 1.48 (m, 3H), 1.75–1.90 (m, 2H), 2.37 (s, 3H), 2.90 & 2.97 (ABX, J=14.0 & 7.0, 2H), 3.40 (m, 2H), 4.18 (t, J=5.6, 1H), 4.90 (s, 4H), 7.19 (d, J=7.5, 2H), 7.20–7.40 (m, 12H), 7.60–7.70 (m, 3H), 12.70 (br m, 1H).

Example 33

Preparation of (2S) 2-N-Isobutyl-2-N-(4-methylbenzenesullonyl)-6-N-(N',N'-dibenzylaminocarbonyl)-2,6-diaminohexanol The methyl ester intermediate of example 32, Nα-isobutyl-Nα-(4-methylbenzenesulfonyl)-Nε-(N',N'-dibenzylaminocarbonyl)-L-lysine methyl ester was reduced with LiAlH₄ following the indications of general procedure E. The desired material was obtained in 88% yield.

¹H NMR (DMSO-d₆): δ 0.82 (d, J=6.7, 3H), 0.84 (d, J=6.7, 3H), 0.90–1.10 (m, 2H), 1.20 (m, 1H), 1.35 (m, 2H), 1.50 (m, 1H), 1.85 (m, 1H), 2.37 (s, 3H), 2.80 & 2.92 (ABX, J=14.0 & 7.0, 2H), 3.27 (m, 2H), 3.35 (m, 2H), 3.50 (m, 1H), 4.61 (m, 1H), 4.90 (s, 4H), 7.16–7.40 (m, 12H), 7.60 (m, 1H), 7.68 (d, J=8.2, 2H).

Example 34

Preparation of (2S) 2-N-Isobutyl-2-N-(4-methylbenzenesulfonyl)-6-N-(N',N'-dibenzylaminothiocarbonyl)-2,6-diaminohexanol The methyl ester intermediate of example 37 below, Nα-isobutyl-Nα-(4-methylbenzenesulfonyl)-Nε-(N',N'- dibenzylaminothiocarbonyl)-L-lysine methyl ester, was reduced with LiAlH$_4$ following the indications of general procedure E. The desired material was obtained in 92% yield.

$^1$H NMR (DMSO-d$_6$): δ 0.82 (d, J=6.7, 3H), 0.84 (d, J=6.7, 3H), 0.90–1.10 (m, 2H), 1.20 (m, 1H), 1.35 (m, 2H), 1.50 (m, 1H), 1.85 (m, 1H), 2.37 (s, 3H), 2.80 & 2.92 (ABX, J=14.0 & 7.0, 2H), 3.27 (m, 2H), 3.35 (m, 2H), 3.50 (m, 1H), 4.61 (m, 1H), 4.90 (s, 4H), 7.16–7.40 (m, 12H), 7.60 (m, 1H), 7.68 (d, J=8.2, 2H).

Example 35

Preparation of Nα-Isobutyl-Nα-(4-methylbenzenesulfonyl)-Nε-(N',N'-diisobutylaminocarbonyl)-L-lysine This product was obtained form Nα-isobutyl-Nα-(4-methylbenzenesulfonyl)-L-lysine methyl ester (IVa) (example 2, step C) as described in general procedure A using diisobutylamine. The final product was obtained in 55% yield.

$^1$H NMR (DMSO-d$_6$): δ 0.77–0.84 (m, 18H), 1.15–1.50 (m, 5H), 1.75–1.95 (m, 4H), 2.37 (s, 3H), 2.85–3.00 (m, 8H), 4.18 (t, J=6.0, 1H), 6.00 (t, J=5.0, 1H), 7.37 (d, J=7.5, 2H), 7.67 (d, J=7.5, 2H), 12.70 (br s, 1H).

Example 36

Preparation of Nα-(4-Aminobenzenesulfonyl)-Nα-isobutyl-Nε-(N',N'-dibenzylaminocarbonyl)-L-lysine This product was obtained form Nα-(4-aminobenzenesulfonyl)-Nα-isobutyl-L-lysine methyl ester (IVb) (example 18, step B) as described in general procedure A using dibenzylamine. The final product was obtained in 44% yield.

$^1$H NMR (DMSO-d$_6$): δ 0.80 (d, J=6.5, 3H), 0.82 (d, J=6.5, 3H), 1.00–1.15 (m, 2H), 1.20–1.35 (m, 3H), 1.52 (m, 1H), 1.85 (m, 1H), 2.73 & 2.85 (ABX, J=14.0 & 7.0, 2H), 3.00 (m, 2H), 3.20 (m, 1H), 3.45 (m, 1H), 4.36 (s, 4H), 4.60 (t, J=5.5, 1H), 5.90 (s, 2H), 6.45 (t, J=5.5, 1H), 6.60 (d, J=8.9, 2H), 7.17 (d, J=7.5, 4H), 7.20–7.40 (m, 10H), 12.70 (br s, 1H).

Example 37

Preparation of Nα-Isobutyl-Nα-(4-methylbenzenesulfonyl)-Nε-(N',N'-dibenzylaminothiocarbonyl)-L-lysine This thiourea was prepared in the same manner as for the urea (general procedure A), by replacing 1,1'-carbonyldiimidazole with 1,1'-thiocarbonyldiimidazole and by using dibenzylamine. The final product was obtained in 69% yield.

$^1$H NMR (DMSO-d$_6$): δ 0.80 (d, J=6.5, 3H), 0.82 (d, J=6.5, 3H), 1.00–1.15 (m, 2H), 1.40–1.50 (m, 3H), 1.75 (m, 1H), 1.90 (m, 1H), 2.90 & 2.97 (ABX, J=14.0 & 7.0, 2H), 3.45 (m, 2H), 4.12 (t, J=7.0, 1H), 4.90 (s, 4H), 7.15–7.40 (m, 12H), 7.65 (m, 3H), 12.70 (br s, 1H).

Example 38

Preparation of Nα-Isobutyl-Nα-(4-methylbenzenesulfonyl)-Nε-[N'-benzyl-N'-(4-picolyl)aminocarbonyl]-L-lysine The title product was obtained form Nα-isobutyl-Nα-(4-methylbenzenesulfonyl)-L-lysine methyl ester (IVa) (example 2, step C) as described in general procedure A using N-benzyl-4-picolylamine. The final product was obtained in 65% yield.

$^1$H NMR (DMSO-d$_6$): δ 0.78 (d, J=7.0, 3H), 0.81 (d, J=7.0, 3H), 1.18 (m, 2H), 1.30–1.50 (m, 3H), 1.75–1.90 (m, 2H), 2.37 (s, 3H), 2.90 & 2.97 (ABX, J=14.0 & 7.0, 2H), 3.02 (m, 2H), 4.18 (t, J=6.2, 1H), 4.52 (s, 2H), 4.63 (s, 2H), 6.80 (t, J=5.5, 1H), 7.20–7.40 (m, 7H), 7.68 (m, 4H), 8.74 (d, J=5.3, 2H), 12.70 (br s, 1H).

Example 39

Preparation of Nα-Isobutyl-Nα-(4-methylbenzenesulfonyl)-Nε-[(N'-benzyl-N'-isopropyl)aminocarbonyl]-L-lysine This compound was obtained form Nα-isobutyl-Nα-(4-methylbenzenesulfonyl)-L-lysine methyl ester (IVa) (example 2, step C) as described in general procedure A using N-benzyl-isopropylamine. The final product was obtained in 47% yield.

$^1$H NMR (DMSO-d$_6$): δ 0.79 (d, J=6.5, 3H), 0.82 (d, J=6.5, 3H), 0.98 (d, J=7.0, 6H), 1.15–1.50 (m, 5H), 1.75–1.95 (m, 2H), 2.37 (s, 3H), 2.85–3.00 (m, 4H), 4.18 (t, J=7.3, 1H), 4.30 (m, 1H), 4.35 (s, 2H), 6.10 (t, J=5.0, 1H), 7.15–7.38 (m, 7H), 7.66 (d, J=7.5, 2H), 12.70 (br s, 1H).

Example 40

Preparation of Nα-Isobutyl-Nα-(4-methylbenzenesulfonyl)-Nε-[(N'-benzyl-N'-methyl)aminocarbonyl]-L-lysine This compound was obtained using the indications of general procedure A with Nα-isobutyl-Nα-(4-methylbenzenesulfonyl)-L-lysine methyl ester (IVa) (example 2, step C) and N-benzylmethylamine. The final product was obtained in 70% yield.

$^1$H NMR (DMSO-d$_6$): δ 0.79 (d, J=6.3, 3H), 0.82 (d, J=6.2, 3H), 1.15–1.50 (m, 5H), 1.75–1.95 (m, 2H), 2.37 (s, 3H), 2.71 (s, 3H), 2.90–3.00 (m, 4H), 4.18 (t, J=7.3, 1H), 4.40 (s, 2H), 6.30 (t, J=5.0, 1H), 7.15–7.38 (m, 7H), 7.66 (d, J=8.0, 2H), 12.70 (br s, 1H).

Example 41

Preparation of (2S) 2-N-(4-Aminobenzenesulfonyl)-2-N-isobutyl-6-N-(N',N'-dibenzylaminocarbonyl)-2,6-diaminohexanol The methyl ester intermediate of example 36, Nα-(4-aminobenzenesulfonyl)-Nα-isobutyl-Nε-(N',N'-dibenzylaminocarbonyl)-L-lysine methyl ester, was reduced with LiAlH$_4$ following the indications of general procedure E. The desired material was obtained in 68% yield.

$^1$H NMR (DMSO-d$_6$): δ 0.82 (d, J=6.3, 3H), 0.85 (d, J=6.4, 3H), 0.90–1.10 (m, 2H), 1.20–1.35 (m, 3H), 1.52 (m, 1H), 1.85 (m, 1H), 2.37 (s, 3H), 2.80 (dd, J=14.0 & 7.0, 1H), 2.94 (m, 3H), 3.22–3.37 (m, 2H), 3.52 (m, 1H), 4.15 (s, 2H), 4.30 (s, 2H), 4.65 (t, J=5.0, 1H), 4.95 (s, 2H), 6.30 (t, J=5.0, 1H, 6.50 (d, J=8.3, 2H), 6.85 (d, J=8.3, 1H), 7.15–7.40 (m, 7H), 7.67 (d, J=7.5, 2H).

Example 42

Preparation of Nα-Isobutyl-Nα-(4-methylbenzenesulfonyl)-Nε-[N'-benzyl-N'-(3-picolyl)aminocarbonyl]-L-lysine The title product was obtained form Nα-isobutyl-Nα-(4-methylbenzenesulfonyl)-L-lysine methyl ester (IVa)

(example 2, step C) as described in general procedure A using N-benzyl-3-picolylamine. The final product was obtained in 55% yield.

$^1$H NMR (DMSO-d$_6$): δ 0.78 (d, J=7.0, 3H), 0.81 (d, J=7.0, 3H), 1.18 (m, 2H), 1.30–1.50 (m, 3H), 1.75–1.90 (m, 2H), 2.37 (s, 3H), 2.90 & 2.97 (ABX, J=14.0 & 7.0, 2H), 3.02 (m, 2H), 4.18 (t, J=6.2, 1H), 4.41 (s, 4H), 6.58 (t, J=5.5, 1H), 7.18–7.40 (m, 7H), 7.55–7.22 (m, 3H), 8.37 (s, 1H), 8.44 (d, J=4.4, 1H), 12.70 (br s, 1H).

Example 43

Preparation of Nα-Isobutyl-Nα-(4-methylbenzenesulfonyl)-Nε-[N'-(4-methoxybenzyl)-N'-(4-picolyl)aminocarbonyl]-L-lysine This compound was obtained form Nα-isobutyl-Nα-(4-methylbenzenesulfonyl)-L-lysine methyl ester (IVa) (example 2, step C) as described in general procedure A using N-(4-methoxybenzyl)-4-picolylamine. The final product was obtained in 73% yield.

$^1$H NMR (DMSO-d$_6$): δ 0.78 (d, J=7.0, 3H), 0.81 (d, J=7.0, 3H), 1.18 (m, 2H), 1.30–1.45 (m, 3H), 1.75–1.90 (m, 2H), 2.37 (s, 3H), 2.90–3.05 (m, 4H), 3.71 (s, 3H), 4.10 (t, J=6.2, 1H), 4.38 (s, 2H), 4.40 (s, 2H), 6.65 (t, J=5.5, 1H), 6.93 (d, J=7.8, 2H), 7.13 (m, 4H), 7.38 (d, J=7.8, 2H), 7.73 (d, J=7.8, 2H), 8.52 (d, J=5.3, 2H), 12.70 (br s, 1H).

Example 44

Preparation of Nα-Isobutyl-Nα-(4-methylbenzenesulfonyl)-Nε-[N',N'-di-(4-picolyl)aminocarbonyl]-L-lysine Following the indications of general procedure A, with Nα-isobutyl-Nα-(4-methylbenzenesulfonyl)-L-lysine methyl ester (IVa) (example 2, step C) and N,N-di-(4-picolyl)amine the desired material was obtained in 55% yield. In this particular case, the reaction was heated at 50° C. for 3 days and the work-up was done at pH 4.

$^1$H NMR (DMSO-d$_6$): δ 0.75 (d, J=7.0, 3H), 0.80 (d, J=7.0, 3H), 1.18 (m, 2H), 1.35 (m, 3H), 1.75–1.90 (m, 2H), 2.35 (s, 3H), 2.90 & 2.97 (ABX, J=14.0 & 7.0, 2H), 3.00 (m, 2H), 4.00 (t, J=7.0, 1H), 4.46 (s, 4H), 6.71 (t, J=5.5, 1H), 7.17 (d, J=4.0, 4H), 7.30 (d, J=7.6, 2H), 7.72 (d, J=7.6, 2H), 8.50 (d, J=4.0, 4H), 12.70 (br s, 1H).

Example 45

Preparation of (2S) 2-N-Isobutyl-2-N-(4-methylbenzenesulfonyl)-6-N-[N'-(4-methoxybenzyl)-N'-(4-picolyl)aminocarbonyl]-2,6-diaminohexanol The methyl ester intermediate of example 43, Nα-isobutyl-Nα-(4-methylbenzenesulfonyl)-Nε-[N'-(4-methoxybenzyl)-N'-(4-picolyl)aminocarbonyl]-L-lysine methyl ester, was reduced with LiAlH$_4$ following the indications of general procedure E. The desired material was obtained in 88% yield.

$^1$H NMR (DMSO-d$_6$): δ 0.82 (d, J=6.7, 3H), 0.84 (d, J=6.7, 3H), 0.90–1.33 (m, 5H), 1.52 (m, 1H), 1.87 (m, 1H), 2.37 (s, 3H), 2.80 & 2.92 (ABX, J=14.0 & 7.0, 2H), 2.95 (m, 2H), 3.20–3.35 (m, 2H), 3.52 (m, 1H), 3.72 (s, 3H), 4.34 (s, 2H), 4.36 (s, 2H), 4.65 (t, J=5.0, 1H), 6.50 (t, J=5.0, 1H), 6.87 (d, J=7.8, 2H), 7.12 (m, 4H), 7.35 (d, J=7.8, 2H), 7.68 (d, J=7.6, 2H), 8.48 (d, J=4.5, 2H).

Example 46

Preparation of (2S) 2-N-Isobutyl-2-N-(4-methylbenzenesulfonyl)-6-N-[N',N'-di-(4-picolyl)aminocarbonyl]-2,6-diaminohexanol The methyl ester intermediate of example 44, Nα-isobutyl-Nα-(4-methylbenzenesulfonyl)-Nε-[N',N'-di-(4-picolyl)aminocarbonyl]-L-lysine methyl ester, was reduced with LiAlH$_4$ following the indications of general procedure E. The desired material was obtained in 28% yield.

$^1$H NMR (DMSO-d$_6$): δ 0.79 (d, J=6.7, 3H), 0.82 (d, J=6.7, 3H), 1.00–1.35 (m, 5H), 1.52 (m, 1H), 1.87 (m, 1H), 2.37 (s, 3H), 2.74 & 2.85 (ABX, J=14.0 & 7.0, 2H), 2.99 (m, 2H), 3.20–3.35 (m, 2H), 3.47 (m, 1H), 4.46 (s, 4H), 4.60 (t, J=5.0, 1H), 6.60 (t, J=5.0, 1H), 7.2 (d, J=4.5, 4H), 7.37 (d, J=7.8, 2H), 7.70 (d, J=7.7, 2H), 8.49 (d, J=4.5, 4H).

Example 47

Preparation of Nα-(4-Aminobenzenesulfonyl)-Nα-isobutyl-Nε-[N'-benzyl-N'-(3-picolyl)aminocarbonyl]-L-lysine This product was obtained in 48% yield from Nα-(4-aminobenzenesulfonyl)-Nα-isobutyl-L-lysine methyl ester (IVb) (example 18, step B) following general procedure A with N-benzyl-3-picolylamine.

$^1$H NMR (DMSO-d$_6$): δ 0.78 (d, J=6.0, 3H), 0.81 (d, J=6.0, 3H), 1.18 (m, 2H), 1.30–1.50 (m, 3H), 1.71–1.90 (m, 2H), 2.86 & 2.90 (ABX, J=14.0 & 7.0, 2H), 3.02 (m, 2H), 4.00 (t, J=7.0, 1H), 4.41 (s, 4H), 6.59 (m, 3H), 7.15–7.40 (m, 7H), 7.60 (d, J=7.5, 1H), 8.46 (d, J=4.0, 1H), 12.70 (br s, 1H).

Example 48

Preparation of Nα-(4-Aminobenzenesulfonyl)-Nα-isobutyl-Nε-[N'-benzyl-N'-(4-picolyl)aminocarbonyl]-L-lysine Nα-(4-aminobenzenesulfonyl)-Nα-isobutyl-Nε-[N'-benzyl-N'-(4-picolyl)aminocarbnyl]-L-lysine was obtained in 39% yield from Nα-(4-aminobenzenesulfonyl)-Nα-isobutyl-L-lysine methyl ester (IVb) (example 18, step B) following the indications of general procedure A with N-benzyl-4-picolylamine.

$^1$H NMR (DMSO-d$_6$): δ 0.78 (d, J=6.0, 3H), 0.81 (d, J=6.0, 3H), 1.18 (m, 2H), 1.30–1.50 (m, 3H), 1.71–1.90 (m, 2H), 2.86 & 2.90 (ABX, J=14.0 & 7.0, 2H), 3.02 (m, 2H), 4.00 (t, J=7.0, 1H), 4.41 (s, 4H), 6.59 (m, 3H), 7.15–7.40 (m, 7H), 7.60 (d, J=7.5, 1H), 8.40 (s, 1H), 8.46 (d, J=4.0, 1H), 12.70 (br s, 1H).

Example 49

Preparation of Nα-(4-Aminobenzenesulfonyl)-Nα-isobutyl-Nε-[N'-(4-methoxybenzyl)-N'-(4-picolyl)aminocarbonyl]-L-lysine The title compound was obtained in 42% yield from Nα-(4-aminobenzenesulfonyl)-Nα-isobutyl-L-lysine methyl ester (IVb) (example 18, step B) following the indications of general procedure A with N-(4-methoxybenzyl)-3-picolylamine.

$^1$H NMR (DMSO-d$_6$): δ 0.77 (d, J=7.0, 3H), 0.80 (d, J=7.0, 3H), 1.18 (m, 2H), 1.30–1.45 (m, 3H), 1.75–1.90 (m, 2H), 2.80–3.05 (m, 4H), 3.72 (s, 3H), 4.10 (t, J=7.0, 1H), 4.36 (s, 2H), 4.41 (s, 2H), 6.57 (d, J=7.5, 2H), 6.61 (t, J=5.5, 1H), 6.88 (d, J=7.8, 2H), 7.13 (d, J=7.8, 2H), 7.27 (d, J=4.0, 2H), 7.40 (d, J=7.8, 2H), 7.70 (m, 1H), 8.52 (d, J=5.3, 2H), 12.70 (br s, 1H).

Example 50

Preparation of (2S) 2-N-(4-Aminobenzenesulfonyl)-2-N-isobutyl-6-N-[N'-benzyl-N'-(3-picolyl)aminocarbonyl]-2,6-diaminohexanol The methyl ester intermediate of example 47, Nα-(4-aminobenzenesulfonyl)-Nα-isobutyl-Nε-[N'-benzyl-N'-(3- picolyl)aminocarbonyl]-L-lysine methyl ester, was reduced with LiAlH$_4$ following the indications of general procedure E. The desired material was obtained in 57% yield.

$^1$H NMR (DMSO-d$_6$): δ 0.80 (d, J=6.7, 3H), 0.82 (d, J=6.7, 3H), 1.00–1.35 (m, 5H), 1.52 (m, 1H), 1.87 (m, 1H), 2.74 & 2.85 (ABX, J=14.0 & 7.0, 2H), 2.99 (m, 2H), 3.20–3.35 (m, 2H), 3.48 (m, 1H), 3.72 (s, 3H), 4.41 (s, 4H), 4.60 (t, J=5.0, 1H), 5.90 (s, 2H), 6.53 (t, J=5.0, 1H), 6.60 (d, J=8.8, 2H), 7.15–7.60 (m, 8H), 8.38 (s, 1H), 8.47 (d, J=4.5, 2H).

Example 51

Preparation of (2S) 2-N-(4-Aminobenzenesulfonyl)-2-N-isobutyl-6-N[N',N'-di-(4-picolyl) aminocarbonyl]-2,6-diaminohexanol This product was obtained from Nα-(4-aminobenzenesulfonyl)-Nα-isobutyl-L-lysine methyl ester (IVb) (example 18, step B) following general procedure A with N,N-di-(4-picolyl)amine. The intermediate methyl ester was reduced with LiAlH$_4$ following the indications of general procedure E. The desired material was obtained in 35% yield.

$^1$H NMR (DMSO-d$_6$): δ 0.79 (d, J=6.7, 3H), 0.82 (d, J=6.7, 3H), 1.00–1.35 (m, 5H), 1.52 (m, 1H), 1.87 (m, 1H), 2.74 & 2.85 (ABX, J=14.0 & 7.0, 2H), 2.99 (m, 2H), 3.20–3.35 (m, 2H), 3.47 (m, 1H), 4.46 (s, 4H), 4.60 (t, J=5.0, 1H), 5.90 (s, 2H), 6.60 (m, 3H), 7.17 (d, J=5.0, 4H), 7.37 (d, J=7.8, 2H), 8.49 (d, J=4.5, 4H).

Example 52

Preparation of (2S) 2-N-(4-Aminobenzenesulfonyl)-2-N-isobutyl-6-N-[N'-benzyl-N'-(4-picolyl) aminocarbonyl]-2,6-diaminohexanol The methyl ester intemediate of example 48, Nα-(4-aminobenzenesulfonyl)-Nα-isobutyl-Nε-[N'-benzyl-N'-(4-picolyl)aminocarbonyl]-L-lysine methyl ester, was reduced with LiAlH$_4$ following the indications of general procedure E. The desired material was obtained in 36% yield.

$^1$H NMR (DMSO-d$_6$): δ 0.80 (d, J=6.7, 3H), 0.82 (d, J=6.7, 3H), 1.00–1.35 (m, 5H), 1.52 (m, 1H), 1.87 (m, 1H), 2.74 & 2.85 (ABX, J=14.0 & 7.0, 2H), 2.99 (m, 2H), 3.20–3.35 (m, 2H), 3.48 (m, 1H), 3.72 (s, 3H), 4.40 (s, 2H), 4.42 (s, 2H), 4.60 (t, J=5.0, 1H), 5.90 (s, 2H), 6.53 (t, J=5.0, 1H), 6.60 (d, J=8.8, 2H), 7.12–7.40 (m, 9H), 8.48 (d, J=4.5, 2H),

Example 53

Preparation of (2S) 2-N-(4-Aminobenzenesulfonyl)-2-N-isobutyl-6-N-[N'-(4-methoxybenzyl)-N'-(4-picolyl)aminocarbonyl]-2,6-diaminohexanol The methyl ester intermediate of example 49, Nα-(4-aminobenzenesulfonyl)-Nα-isobutyl-Nε-[N'-(4-methoxybenzyl)-N'-(4-picolyl)aminocarbonyl]-L-lysine methyl ester, was reduced with LiAlH$_4$ following the indications of general procedure E. The desired material was obtained in 67% yield.

$^1$H NMR (DMSO-d$_6$): δ 0.80 (d, J=6.7, 3H), 0.82 (d, J=6.7, 3H), 1.00–1.35 (m, 5H), 1.52 (m, 1H), 1.87 (m, 1H), 2.74 & 2.85 (ABX, J=14.0 & 7.0, 2H), 2.99 (m, 2H), 3.20–3.35 (m, 2H), 3.52 (m, 1H), 3.72 (s, 3H), 4.34 (s, 2H), 4.36 (s, 2H), 4.60 (t, J=5.0, 1H), 5.90 (s, 2H), 6.52 (t, J=5.0, 1H), 6.60 (d, J=8.8, 2H), 6.87 (d, J=7.8, 2H), 7.12 (m, 4H), 7.37 (d, J=7.8, 2H), 8.48 (d, J=4.5, 2H).

Example 54

Preparation of Nα-Isobutyl-Nα-(4-methylbenzenesulfonyl)-Nε-[N'-benzyl-N'-(2-nitrobenzyl)aminocarbonyl]-L-lysine Following the indications of general procedure A, with Nα-isobutyl-Nα-(4-methylbenzenesulfonyl)-L-lysine methyl ester (IVa) (example 2, step C) and N-benzyl-2-nitrobenzylamine the desired material was obtained in 82% yield.

$^1$H NMR (DMSO-d$_6$): δ 0.78 (d, J=6.8, 3H), 0.81 (d, J=6.7, 3H), 1.18 (m, 2H), 1.30–1.48 (m, 3H), 1.75–1.90 (m, 2H), 2.37 (s, 3H), 2.88 & 2.97 (ABX, J=14.0 & 7.0, 2H), 3.00 (m, 2H), 4.16 (t, J=7.0, 1H), 4.50 (s, 2H), 4.70 (s, 2H), 6.58 (t, J=5.5, 1H), 7.18–7.40 (m, 7H), 7.52 (t, J=7.6, 1H), 7.67 (d, J=7.5, 2H), 7.74 (t, J=7.6, 1H), 8.09 (d, J=7.5, 1H), 12.70 (br s, 1H).

Example 55

Preparation of Nα-Isobutyl-Nα-(4-methylbenzenesulfonyl)-Nε-[N'-benzyl-N'-(3-nitrobenzyl)aminocarbonyl]-L-lysine Following the indications of general procedure A, with Nα-isobutyl-Nα-(4-methylbenzenesulfonyl)-L-lysine methyl ester (IVa) (example 2, step C) and N-benzyl-3-nitrobenzylamine the desired material was obtained in 80% yield.

$^1$H NMR (DMSO-d$_6$): δ 0.78 (d, J=6.8, 3H), 0.81 (d, J=6.7, 3H), 1.18 (m, 2H), 1.35–1.50 (m, 3H), 1.75–1.90 (m, 2H), 2.37 (s, 3H), 2.88 & 2.97 (ABX, J=14.0 & 7.0, 2H), 3.00 (m, 2H), 4.16 (t, J=7.0, 1H), 4.45 (s, 2H), 4.52 (s, 2H), 6.63 (t, J=5.5, 1H), 7.18–7.40 (m, 7H), 7.58–7.70 (m, 4H), 8.00 (s, 1H), 8.09 (d, J=7.5, 1H), 12.70 (br s, 1H).

Example 56

Preparation of Nα-Isobutyl-Nα-(4-methylbenzenesulfonyl)-Nε-[N'-benzyl-N'-(4-nitrobenzyl)aminocarbonyl]-L-lysine Following the indications of general procedure A, with Nα-isobutyl-Nα-(4-methylbenzenesulfonyl)-L-lysine methyl ester (IVa) (example 2, step C) and N-benzyl-4-nitrobenzylamine the desired material was obtained in 88% yield.

$^1$H NMR (DMSO-d$_6$): δ 0.78 (d, J=6.3, 3H), 0.81 (d, J=6.3, 3H), 1.18 (m, 2H), 1.35–1.50 (m, 3H), 1.75–1.90 (m, 2H), 2.37 (s, 3H), 2.88 & 2.97 (ABX, J=14.0 & 7.0, 2H), 3.00 (m, 2H), 4.18 (t, J=7.0, 1H), 4.43 (s, 2H), 4.51 (s, 2H), 6.62 (t, J=5.5, 1H), 7.17–7.42 (m, 7H), 7.67 (d, J=7.6, 2H), 8.18 (m, 3H), 8.32 (d, J=7.8, 1H), 12.70 (br s, 1H).

Example 57

Preparation of Nα-Isobutyl-Nα-(4-methylbenzenesulfonyl)-Nε-[N'-(2-ninobenzyl)-N'-benzylaminocarbonyl]-L-lysine The product of example 54, Nα-isobutyl-Nα-(4-methylbenzenesulfonyl)-Nε-[N'-benzyl-N'-(2-nitrobenzyl) aminocarbonyl]-L-lysine, was reduced by catalytic hydrogenation following the indications of general procedure D. The desired material was obtained in 76% yield.

$^1$H NMR (DMSO-d$_6$): δ 0.79 (d, J=6.8, 3H), 0.81 (d, J=6.7, 3H), 1.18 (m, 2H), 1.30–1.48 (m, 3H), 1.75–1.90 (m, 2H), 2.37 (s, 3H), 2.88–3.12 (m, 4H), 4.13 (t, J=7.0, 1H), 4.20 (s, 2H), 4.34 (s, 2H), 6.45 (m, 2H), 6.60 (d, J=8.1, 1H), 6.80 (d, J=8.0, 1H), 6.97 (t, J=7.8, 1H), 7.18 (d, J=7.8, 2H), 7.25 (t, J=7.8, 1H), 7.30–7.40 (m, 4H), 7.67 (d, J=7.8, 2H), 12.70 (br s, 1H).

Example 58

Preparation of Nα-Isobutyl-Nα-(4-methylbenzenesulfonyl)-Nε-[N'-(3-aminobenzyl)-N'-benzylaminocarbonyl]-L-lysine The product of example 55, Nα-isobutyl-Nα-(4-methylbenzenesulfonyl)-Nε-[N'-benzyl-N'-(3-nitrobenzyl) aminocarbonyl]-L-lysine, was reduced by catalytic hydrogenation following the indications of general procedure D. The desired material was obtained in 66% yield.

$^1$H NMR (DMSO-d$_6$): δ 0.79 (d, J=6.8, 3H), 0.81 (d, J=6.7, 3H), 1.18 (m, 2H), 1.30–1.52 (m, 3H), 1.75–1.90 (m, 2H), 2.37 (s, 3H), 2.88–3.12 (m, 4H), 3.40 (t, J=6.0, 1H), 4.16 (t, J=7.0, 1H), 4.20 (s, 2H), 4.34 (s, 2H), 6.30–6.45 (m, 4H), 6.90–7.00 (m, 1H), 7.15–7.40 (m, 7H), 7.68 (d, J=8.1, 2H), 12.70 (br s, 1H).

Example 59

Preparation of (2S) 2-N-Isobutyl-2-N-(4-methylbenzenesulfonyl)-6-N-[N'-benzyl-N'-(2-nitrobenzyl)aminocarbonyl]-2,6-diaminohexanol The methyl ester intermediate of example 54, Nα-isobutyl-Nα-(4-methylbenzenesulfonyl)-Nε-[N'-benzyl-N'-(2-nitrobenzyl)aminocarbonyl]-L-lysine methyl ester, was reduced with LiAlH$_4$ following the indications of general procedure E. The desired material was obtained in 71% yield.

$^1$H NMR (DMSO-d$_6$): δ 0.81 (d, J=6.7, 3H), 0.83 (d, J=6.7, 3H), 0.90–1.40 (m, 5H), 1.50 (m, 1H), 1.88 (m, 1H), 2.37 (s, 3H), 2.80 & 2.92 (ABX, J=14.0 & 7.0, 2H), 2.93 (m, 2H), 3.20–3.35 (m, 2H), 3.50 (m, 1H), 4.50 (s, 2H), 4.65 (t, J=5.0, 1H), 4.70 (s, 2H), 6.50 (t, J=5.5, 1H), 7.17–7.38 (m, 9H), 7.50 (t, J=7.5, 1H), 7.65 (d, J=7.6, 2H), 7.75 (t, J=7.5, 1H), 8.09 (d, J=8.3, 2H).

Example 60

Preparation of (2S) 2-N-Isobutyl-2-N-(4-methylbenzenesulfonyl)-6-N-[N'-benzyl-N'-(3-nitrobenzyl)aminocarbonyl]-2,6-diaminohexanol The methyl ester intermediate of example 55, Nα-isobutyl-Nα-(4-methylbenzenesulfonyl)-Nε-[N'-benzyl-N'-(3-nitrobenzyl)aminocarbonyl]-L-lysine methyl ester, was reduced with LiAlH$_4$ following the indications of general procedure E. The desired material was obtained in 66% yield.

$^1$H NMR (DMSO-d$_6$): δ 0.81 (d, J=6.7, 3H), 0.83 (d, J=6.7, 3H), 0.90–1.33 (m, 5H), 1.50 (m, 1H), 1.88 (m, 1H), 2.37 (s, 3H), 2.80 & 2.92 (ABX, J=14.0 & 7.0, 2H), 2.97 (m, 2H), 3.20–3.35 (m, 2H), 3.50 (m, 1H), 4.45 (s, 2H), 4.52 (s, 2H), 4.65 (t, J=5.0, 1H), 6.55 (t, J=5.0, 1H), 7.17–7.38 (m, 9H), 7.58–7.68 (m, 4H), 8.00 (s, 1H), 8.20 (d, J=7.6, 2H).

Example 61

Preparation of (2S) 2-N-Isobutyl-2-N-(4-methylbenzenesulfonyl)-6-N-[N'-benzyl-N'-(4-nitrobenzyl)aminocarbonyl]-2,6-diaminohexanol The methyl ester intermediate of example 56, Nα-isobutyl-Nα-(4-methylbenzenesulfonyl)-Nε-[N'-benzyl-N'-(4-nitrobenzyl)aminocarbonyl]-L-lysine methyl ester, was reduced with LiAlH$_4$ following the indications of general procedure E. The desired material was obtained in 78% yield.

$^1$H NMR (DMSO-d$_6$): δ 0.81 (d, J=6.7, 3H), 0.83 (d, J=6.7, 3H), 0.90–1.40 (m, 5H), 1.50 (m, 1H), 1.88 (m, 1H), 2.37 (s, 3H), 2.80 & 2.92 (ABX, J=14.0 & 7.0, 2H), 2.97 (m, 2H), 3.20–3.35 (m, 2H), 3.50 (m, 1H), 4.43 (s, 2H), 4.51 (s, 2H), 4.68 (t, J=5.0, 1H), 6.55 (t, J=5.5, 1H), 7.17–7.42 (m, 9H), 7.65 (d, J=7.6, 2H), 8.18 (d, J=7.6, 2H).

Example 62

Preparation of (2S) 2-N-Isobutyl-2-N-(4-methylbenzenesulfonyl)-6-N-[N'-(2-aminobenzyl)-N'-benzylaminocarbonyl]-2,6-diaminohexanol The product of example 59, (2S) 2-N-isobutyl-2-N-(4-methylbenzenesulfonyl)-6-N-[N'-benzyl-N'-(2-nitrobenzyl)aminocarbonyl]-2,6-diaminohexanol, was reduced by catalytic hydrogenation following the indications of general procedure D. The desired material was obtained in 86% yield.

$^1$H NMR (DMSO-d$_6$): δ 0.81 (d, J=6.7, 3H), 0.84 (d, J=6.7, 3H), 0.90–1.10 (m, 2H), 1.20–1.32 (m, 3H), 1.52 (m, 1H), 1.87 (m, 1H), 2.37 (s, 3H), 2.80 (dd, J=14.0 & 7.0, 1H), 2.91 (m, 3H), 3.22–3.37 (m, 2H), 3.52 (m, 1H), 4.20 (s, 2H), 4.35 (s, 2H), 4.65 (t, J=5.0, 1H), 5.27 (s, 2H), 6.39 (t, J=5.0, 1H), 6.47 (t, J=7.5, 1H), 6.60 (d, J=7.5, 1H), 6.80 (d, J=7.6, 1H), 6.95 (t, J=5.0, 1H), 7.16 (d, J=7.5, 2H), 7.20–7.38 (m, 6H), 7.66 (d, J=7.5, 2H).

Example 63

Preparation of (2S) 2-N-Isobutyl-2-N-(4-methylbenzenesulfonyl)-6-N-[N'-(3-aminobenzyl)-N'-benzylaminocarbonyl]-2,6-diaminohexanol The product of example 60, (2S) 2-N-isobutyl-2-N-(4-methylbenzenesulfonyl)-6-N-[N'-benzyl-N'-(3-nitrobenzyl)aminocarbonyl]-2,6-diaminohexanol, was reduced by catalytic hydrogenation following the indications of general procedure D. The desired material was obtained in 86% yield.

$^1$H NMR (DMSO-d$_6$): δ 0.82 (d, J=6.7, 3H), 0.84 (d, J=6.7, 3H), 0.90–1.10 (m, 2H), 1.20–1.35 (m, 3H), 1.52 (m, 1H), 1.87 (m, 1H), 2.37 (s, 3H), 2.80 (dd, J=14.0 & 7.0, 1H), 2.94 (m, 3H), 3.22–3.37 (m, 2H), 3.52 (m, 1H), 4.20 (s, 2H), 4.35 (s, 2H), 4.65 (t, J=5.0, 1H), 5.02 (s, 2H), 6.30 (d, J=7.5, 1H), 6.36 (t, J=5.0, 1H), 6.40 (s, 1H), 6.43 (d, J=7.5, 1H), 6.95 (t, J=5.0, 1H, 7.16 (d, J=7.5, 2H), 7.20–7.38 (m, 5H), 7.66 (d, J=7.5, 2H).

Example 64

Preparation of (2S) 2-N-Isobutyl-2-N-(4-methylbenzenesulfonyl)-6-N-[N'-(4-aminobenzyl)-N'-benzylaminocarbonyl]-2,6-diaminohexanol The product of example 61, (2S) 2-N-isobutyl-2-N-(4-methylbenzenesulfonyl)-6-N-[N'-benzyl-N'-(4-nitrobenzyl)aminocarbonyl]-2,6-diaminohexanol, was reduced by catalytic hydrogenation following the indications of general procedure D. The desired material was obtained in 89% yield.

$^1$H NMR (DMSO-d$_6$): δ 0.82 (d, J=6.3, 3H), 0.85 (d, J=6.4, 3H), 0.90–1.10 (m, 2H), 1.20–1.35 (m, 3H), 1.52 (m, 1H), 1.85 (m, 1H), 2.37 (s, 3H), 2.80 (dd, J=14.0 & 7.0, 1H), 2.94 (m, 3H), 3.22–3.37 (m, 2H), 3.52 (m, 1H), 4.15 (s, 2H), 4.30 (s, 2H), 4.65 (t, J=5.0, 1H), 4.95 (s, 2H), 6.30 (t, J=5.0, 1H), 6.50 (d, J=8.3, 2H), 6.85 (d, J=8.3, 1H), 7.15–7.40 (m, 7H), 7.67 (d, J=7.5, 2H).

Example 65

Preparation of (2S,2'S) 2-N-(4-Aminobenzenesulfonyl)-2-N-isobutyl-6-N-(S-tryptophanyl-N'-carbonyl)-2,6-diaminohexanol The preparation of the title compound is based on schemes 4 and 6 of this invention.

Step A. Preparation of Nα-Isobutyl-Nα-(4-acetamidobenzenesulfonyl)-L-α-amino-ε-caprolactam Nα-isobutyl-L-α-amino-ε-caprolactam (XII, 4.14 g, 21.1 mmol, free base, example 1, step C) was dissolved in DCE (50 mL) and treated with diisopropylethylarmine (6 mL, 0.3 mol) followed by freshly recrystallized 4-acetamidobenzenesulfonyl chloride (5.06 g, 21.6 mmol). The mixture was stirred overnight (TLC shows the reaction to be complete after 2 h). The solution was extracted with 1N HCl (50 mL) and the organic layer was dried and evaporated. The crude material (7.01 g, 83%) was of sufficient purity to be used as such in the next step.

$^1$H NMR (CDCl$_3$): δ 0.93 (d, J=6.0, 3H), 0.96 (d, J=6.0, 3H), 1.39 (t, J=12.0, 1H), 1.85–1.65 (m, 3H), 2.08–2.18 (m and s, 6H), 2.90–2.97 (m 1H), 3.00–3.06 (m, 2H), 3.35 (dd, J=14.2, 8.5, 1H), 4.65 (d, J=8.7, 1H), 6.3 (s, 1H), 7.42 (d, J=8.8, 2H), 7.6 (d, J=8.8, 2H).

Step B. Preparation of Nα-(4-Aminobenzenesulfonyl)-Nα-isobutyl-L-lysine Potassium Salt A mixture of Nα-isobutyl-Nα-(4-acetamidobenzenesulfonyl)-L-α-amino-ε-caprolactam (6.8 g, 2 mmol) and 6N HCl (200 mL) was refluxed for 12 h until all solids had disappeared. Afterwards, the solution was evaporated to dryness. The resulting solid was dissolved in EtOH (15 mL), neutralized with KOH and precipitated from acetone to give 8.0 g (100%) of the pure potassium salt.

$^1$H NMR (DMSO-d$_6$): δ 0.72 (dd, J=5.8, 6.4, 6H), 1.13–1.27 (m, 3H), 1.37–1.44 (m 1H), 1.72–1.78 (m, 1H), 1.92–1.98 (m, 1H), 2.67–2.73 (m, 2H), 2.80–2.91 (m, 2H), 3.85 (t, J=7.2, 1H), 6.56 (d, J=8.5, 2H), 7.44 (d, J=8.5, 2H).

Step C. Preparation of (2S) 2-N-(4-Aminobenzenesulfonyl)-2-N-isobutyl-2,6-diaminohexanol A solution of Nα-(4-aminobenzenesulfonyl)-Nα-isobutyl-L-lysine (13.0 g, 40.0 mmol, step B) dissolved in MeOH (200 mL) was treated with of trimethylsilyl chloride (25 mL). The mixture was refluxed 3 h before stirring at room temperature for 2 h. Afterwards, the solution was evaporated and placed under high vacuum until a white solid was obtained (14.0 g). This was suspended in dry THF (100 mL) and added dropwise to a solution of LiAlH (5.0 g, 150 mmol) in THF (300 mL). The solution was stirred for 4 h. After cooling in an ice bath the solution was quenched by addition of MeOH (50 mL), water (5 mL), then 10% NaOH (5 mL). The solvent was evaporated and the product was extracted from the precipitate with MeOH using a Soxlet apparatus during 18 h. Then, the solvent was evaporated to form a white solid which was dissolved in EtOH, filtered to eliminate Al$_2$O$_3$ and, after cooling, crystallized on standing (12.0 g, 88%).

$^1$H NMR (DMSO-d$_6$): δ 0.82 (m, 6H), 0.97–1.12 (m, 2H), 1.15–1.30 (m, 3H), 1.57 (m, 1H), 1.84 (m, 1H), 2.40 (t, J=7.0, 2H), 2.75 (m, 1H), 2.85 (m, 1H), 3.21 (m, 1H), 3.44 (d, J=6.0, 2H), 5.92 (s, 2H), 6.59 (d, J=8.0, 2H), 7.39 (d, J=8.0, 2H).

Step D. Preparation of (2S) 2-N-(4-Aminobenzenesulfonyl)-2-N-isobutyl-6-N-(9-fluorenylmethoxycarbonyl)-2,6-diaminohexanol (XVIII)

The product of step C of this example (1 mmol) was partially dissolved in K$_2$CO$_3$ (1M)/THF/CH$_3$CN (4 mL/4 mL/4 mL). To this suspension was added N-(9-fluorenylmethoxycarbonyloxy) succinimide (371 mg, 1.10 mmol). The reaction turned slowly to colourless and was left stirring for 1 h. HCl (1M) was added until acidic pH and the reaction mixture was extracted twice with EtOAc. The combined organic layers were washed with brine, dried over MgSO$_4$ and concentrated. The residue was purified by flash chromatography eluting with a mixture of hexane/EtOAc containing 0.4% AcOH to yield 448 mg, 79% of the title compound.

$^1$H NMR (DMSO-d$_6$): δ 0.80 (d, J=6.7, 3H), 0.81 (d, J=6.3, 3H), 1.04 (m, 1H), 1.14 (m, 1H), 1.29 (m, 3H), 1.53 (m, 1H), 1.84 (m, 1H), 2.73 (dd, J=7.2 & 14.4, 1H), 2.86 (m, 3H), 3.24 (t, J=7.1, 2H), 3.45 (m, 1H), 4.21 (d, J=6.6, 1H), 4.28 (d, J=6.8, 2H), 4.59 (br s, 1H), 5.90 (br s, 2H), 6.59 (d, J=8.9, 2H), 7.20 (m, 1H), 7.33 (t, J=7.4, 1H), 7.41 (m, 4H), 7.68 (d, J=7.4, 2H), 7.89 (d, J=7.5, 2H).

Step E. Preparation of (2S,2'S) 2-N-(4-Aminobenzenesulfonyl)-2-N-isobutyl-6-N-(S-tryptophanyl-N'-carbonyl)-2,6-diaminohexanol The title compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (step D) as described in general procedure C using commercially available L-tryptophan (1.1 molar excess). The final product was purified by preparative HPLC to yield 17 mg (21%) of the desired material.

$^1$H NMR (CDCl$_3$): δ 0.82 (d, J=6.8, 3H), 0.84 (d, J=6.8, 3H), 1.08–1.11 (m, 2H), 1.18–1.22 (m, 2H), 1.45–1.52 (m, 1H), 2.38 (s, 3H), 2.84–3.09 (m, 4H), 3.15–3.18 (m, 1H), 3.44–3.66 (m, 3H), 4.25 (t, J=7.3, 1H), 6.85, (t, J=7.2, 1H), 7.00–7.04 (m, 2H), 7.28–7.32 (m, J=8.1, 2H), 7.56 (d, J=8.1, 1H), 7.69, (d, J=7.2, 2H).

Example 66

Preparation of (2S) 2-N-(4-Aminobenzenesulfonyl)-2-N-isobutyl-6-N-[N'-cyclohexyl-N'-(4-fluorobenzyl)aminocarbonyl]-2,6-diaminohexanol The title compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-cyclohexyl-4-fluorobenzylamine (1.1 molar excess). The preparation of the amine was done as described in general procedure F. The final product was purified by preparative HPLC to yield 6.6 mg (7%) of the desired material.

$^1$H NMR (CDCl$_3$): δ 0.83 (d, J=6.9, 6H), 1.08–1.11 (m, 3H), 1.23–1.45 (m, 8H), 1.62–1.72 (m, 6H), 1.89–1.99 (m, 2H), 2.94–3.09 (m, 4H), 3.44–3.66 (m, 3H), 4.03 (t, J=5.9, 1H), 4.41 (s, 2H), 6.75 (d, J=5.1, 2H), 7.06 (t, J=5.5, 2H), 7.33 (t, J=5.5, 2H), 7.43 (d, J=5.1, 2H).

Example 67

Preparation of (2S) 2-N-(4-Aminobenzenesulfonyl)-2-N-isobutyl-6-N-[N'-(4-fluorobenzyl)-N'-piperonylaminocarbonyl]-2,6-diaminohexanol The title compound was prepared from solid phase bound (2S) 2-N-(4-aminobenzenesulfonyl)-2-N-isobutyl-6-N-(9- fluorenylmethoxycarbonyl)-2,6-diaminohexanol (XVIII) (example 65, step D) as described in general procedure C using freshly prepared N-4-fluorobenzyl-piperonylamine (1.1 molar excess). The preparation of the amine was done as described in general procedure F. The final product was purified by preparative HPLC to yield 2.7 mg (2%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 4.41 (s, 2H), 4.57 (s, 2H), 5.96 (s, 2H), 6.75 (d, J=5.1, 2H), 7.06 (t, J=5.5, 2H), 7.33 (t, J=5.5, 2H), 7.43 (d, J=5.1, 2H).

Example 68

Preparation of (2S) 2-N-(4-Aminobenzenesulfonyl)-2-N-isobutyl-6-N-[N'-benzyl-N'-(4-fluorobenzyl)aminocarbonyl]-2,6-diaminohexanol This derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-benzyl-4-fluorobenzylamine (1.1 molar excess). The preparation of the amine was done as described in general procedure F. The final product was purified by preparative HPLC to yield 3.1 mg (3%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 2H), 1.89–1.99 (m, 1H), 2.84–2.99 (m, 2H), 3.09–3.2 (m, 2H), 3.44–3.66 (m, 3H), 4.61 (s, 4H), 6.75 (d, J=5.1, 2H), 7.06 (t, J=5.5, 2H), 7–15–7.33 (m, 8H), 7.43 (d, J=5.1, 2H), 7.9 (s, 1H), 8.2 (s, 1H), 8.7 (s, 2H).

Example 69

Preparation of (2S) 2-N-(4-Aminobenzenesulfonyl)-2-N-isobutyl-6-N-[N'-(4-fluorobenzyl)-N'-(2-thiophenethyl)aminocarbonyl]-2,6-diaminohexanol This compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-4-fluorobenzyl-2-thiophenethylamine (1.1 molar excess). The preparation of the amine was done as described in general procedure F. The final product was purified by preparative HPLC to yield 3.3 mg (3%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 5H), 3.44–3.66 (m, 6H), 4.51 (s, 2H), 6.75 (d, J=5.1, 2H), 6.80 (s, 1H), 6.88 (t, J=4.4, 1H), 7.06 (t, J=5.5, 2H), 7.22 (d, J=4.4, 1H), 7.33 (t, J=5.5, 2H), 7.43 (d, J=5.1, 2H).

Example 70

Preparation of (2S) 2-N-(4-Aminobenzenesulfonyl)-2-N-isobutyl-6-N-[N'-(4-fluorobenzyl)-N'-(3-picolyl)aminocarbonyl]-2,6-diaminohexanol This derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-4-fluorobenzyl-3-picolylamine (1.1 molar excess). The preparation of the amine was done as described in general procedure F. The final product was purified by preparative HPLC to yield 7.4 mg (7%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 2H), 1.89–1.99 (m, 1H), 2.84–2.99 (m, 2H), 3.09–3.2 (m, 2H), 3.44–3.66 (m, 3H), 4.61 (s, 2H), 4.77 (s, 2H), 6.75 (d, J=5.1, 2H,), 7.06 (t, J=5.5, 2H), 7.33 (t, J=5.5, 2H), 7.43 (d, J=5.1, 2H), 7.9 (s, 1H), 8.2 (s, 1H, 8.7 (s, 2H).

Example 71

Preparation of (2S) 2-N-(4-Aminobenzenesulfonyl)-2-N-isobutyl-6-N-[N'-cyclohexyl-N'-(3-fluorobenzyl)aminocarbonyl]-2,6-diaminohexanol The title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-cyclohexyl-3-fluorobenzylamine (1.1 molar excess). The preparation of the amine was done as described in general procedure F. The final product was purified by preparative HPLC to yield 1.0 mg (1%) of the desired material.

$^1$H NMR (CDCl$_3$): δ 0.83 (d, J=6.9, 6H), 1.08–1.11 (m, 3H), 1.23–1.45 (m, 8H), 1.65–1.72 (m, 6H), 1.89–1.99 (m, 2H), 2.94–3.09 (m, 4H), 3.44–3.66 (m, 3H), 4.03 (t, J=5.9, 1H), 4.41 (s, 2H), 6.85 (t, J=4.1, 1H), 6.96 (d, J=4.4, 1H), 7.06 (d, J=4.4, 1H), 7.33 (t, J=4.1, 1H).

Example 72

Preparation of (2S) 2-N-(4-Aminobenzenesulfonyl)-2-N-isobutyl-6-N-[N'-(3-fluorobenzyl)-N'-(3-picolyl)aminocarbonyl]-2,6-diaminohexanol The title compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-3-fluorobenzyl-3-picolylamine (1.1 molar excess). The preparation of the amine was done as described in general procedure F. The final product was purified by preparative HPLC to yield 3.5 mg (3%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 2H), 1.89–1.99 (m, 1H), 2.84–2.99 (m, 2H), 3.09–3.2 (m, 2H), 3.44–3.66 (m, 3H), 4.51 (s, 2H), 4.57 (s, 2H), 6.85 (t, J=4.1, 1H), 6.96 (d J=4.4, 1H), 7.06 (d J=4.4, 1H), 7.33 (t, J=4.1, 1H), 7.9 (s, 1H), 8.2 (s, 1H), 8.7 (s, 2H).

Example 73

Preparation of (2S) 2-N-(4-Aminobenzenesulfonyl)-2-N-isobutyl-6-N-[N'-(2-fluorobenzyl)-N'-(3-picolyl)aminocarbonyl]-2,6-diaminohexanol This product was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-2-fluorobenzyl-3-picolylamine (1.1 molar excess). The preparation of the amine was done as described in general procedure F. The final product was purified by preparative HPLC to yield 4.5 mg (4%) of the desired material.

¹H NMR (CDCl₃): δ 0.83 (d, J=6.9, 6H), 1.08–1.71 (m, 2H), 1.23–1.45 (m, 3H), 1.65–1.72 (m, 2H), 1.89–1.99 (m, 1H), 2.84–2.99 (m, 2H), 3.09–3.2 (m, 2H), 3.44–3.66 (m, 3H), 4.61 (s, 2H), 4.87 (s, 2H), 6.85 (t, J=4.1, 1H), 6.96 (d, J=4.4, 1H), 7.06–7.25 m, 2H), 7.9 (s, 1H), 8.2 (s, 1H), 8.7 (s, 2H).

Example 74

Preparation of (2S) 2-N-(4-Aminobenzenesulfonyl)-2-N-isobutyl-6-N-piperonylaminocarbonyl-2,6-diaminohexanol This compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using commercially available piperonylamine (1.1 molar excess). The final product was purified by preparative HPLC to yield 11.0 mg (13%) of the desired material.

¹H NMR (CDCl₃): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 4.21 (s, 2H), 5.96 (s, 2H), 6.75–6.80 (m, 4H), 7.43 (d, J=5.1, 2H).

Example 75

Preparation of (2S) 2-N-(4-Aminobenzenesulfonyl)-2-N-isobutyl-6-N-[N'-(2-thiophenemethyl)-N'-piperonylaminocarbonyl]-2,6-diaminohexanol The title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-2-thiophenemethyl-3-piperonylamine (1.1 molar excess). The preparation of the amine was done as described in general procedure F. The final product was purified by preparative HPLC to yield 9.0 mg (8%) of the desired material.

¹H NMR (CDCl₃): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 4.31 (s, 2H), 4.47 (s, 2H), 5.96 (s, 2H), 6.75–6.80 (m, 4H), 6.96 (d, J=5.2, 1H), 7.43 (d, J=5.1, 2H), 7.62 (d, J=5.2, 1H), 7.77 (d, J=5.2, 1H).

Example 76

Preparation of (2S) 2-N-(4-Aminobenzenesulfonyl)-2-N-isobutyl-6-N-[N'-benzyl-N'-(3-thiophenemethyl)aminocarbonyl]-2,6-diaminohexanol This compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-benzyl-3-thiophenemethylamine (1.1 molar excess). The preparation of the amine was done as described in general procedure F. The final product was purified by preparative HPLC to yield 4.0 mg (4%) of the desired material.

¹H NMR (CDCl₃): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 4.41 (s, 2H), 4.47 (s, 2H), 6.75–6.80 (m, 2H), 6.96 (d, J=5.2, 1H), 7.12–7.33 (m, 8H), 7.43 (d, J=5.1, 2H), 7.62 (d, J=5.2, 1H), 7.77 (d, J=5.2, 1H).

Example 77

Preparation of (2S) 2-N-(4-Aminobenzenesulfonyl)-2-N-isobutyl-6-N-(N'-4-methoxybenzylaminocarbonyl)-2,6-diaminohexanol The title compound was prepared from solid phase bound (2S) 2-N-(4-anobenzenesulfonyl)-2-N-isobutyl-6-N-(9-fluorenylmethoxycarbonyl)-2,6-diaminohexanol (XVIII) (example 65, step D) as described in general procedure C using commercially available 4-methoxybenzylamine (1.1 molar excess). The final product was purified by preparative HPLC to yield 14 mg (15%) of the desired material.

¹H NMR (CDCl₃): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 3.72 (s, 3H), 4.21 (s, 2H), 6.75 (d, J=5.2, 2H), 6.80 (d, J=5.3, 2H), 7.22 (d, J=5.3, 2H), 7.43 (d, J=5.1, 2H).

Example 78

Preparation of (2S) 2-N-(4-Aminobenzenesulfonyl)-2-N-isobutyl-6-N-(N'-2,6-dimethoxybenzylaminocarbonyl)-2,6-diaminohexanol This derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using commercially available 2,6-dimethoxybenzylamine (1.1 molar excess). The final product was purified by preparative HPLC to yield 12 mg (15%) of the desired material.

¹H NMR (CDCl₃): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 3.72 (s, 6H), 4.21 (s, 2H), 6.75 (d, J=5.2, 2H), 6.80 (d, J=8.3, 2H), 7.02 (t, J=5.3, 1H), 7.43 (d, J=5.1, 2H).

Example 79

Preparation of (2S) 2-N-(4-Aminobenzenesulfonyl)-2-N-isobutyl-6-N-(N'-2,4-dimethoxybenzylaminocarbonyl)-2,6-diaminohexanol This compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using commercially available 2,4-dimethoxybenzylamine (1.1 molar excess). The final product was purified by preparative HPLC to yield 9.0 mg (12%) of the desired material.

¹H NMR (CDCl₃): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 3.72 (s, 6H), 4.21 (s, 2H), 6.75 (d, J=5.2, 2H), 6.80 (d, J=8.3, 2H), 6.91 (s, 1H), 7.43 (d, J=2H).

Example 80

Preparation of (2S) 2-N-(4-Aminobenzenesulfonyl)-2-N-isobutyl-6-N-(N'-3,5-dimethoxybenzylaminocarbonyl)-2,6-diaminohexanol The title derivative was prepared from solid phase bound (2S) 2-N-(4-aminobenzenesulfonyl)-2-N-isobutyl-6-N-(9- fluorenylmethoxycarbonyl)-2,6-diaminohexanol (XVIII) (example 65, step D) as described in general procedure C using commercially available 3,5-dimethoxybenzylamine (1.1 molar excess). The final product was purified by preparative HPLC to yield 8.0 mg (10%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.44–3.66 (m, 3H), 3.72 (s, 6H), 4.21 (s, 2H), 6.33 (s, 1H), 6.40 (s, 2H), 6.75 (d, J=5.2, 2H), 6.80 (d, J=8.3, 2H), 7.02 (t, J=5.3, 1H), 7.43 (d, J=5.1, 2H).

Example 81

Preparation of (2S) 2-N-(4-Aminobenzenesulfonyl)-2-N-isobutyl-6-N-[N'-(3-thiophenemethyl)-N'-piperonylaminocarbonyl]-2,6-diaminohexanol The title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-3-thiophenemethylpiperonylamine (1.1 molar excess). The preparation of the amine was done as described in general procedure F. The final product was purified by preparative HPLC to yield 6.0 mg (9%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.56–3.66 (m, 3H), 4.37 (s, 2H), 4.47 (s, 2H), 5.96 (s, 2H), 6.75–6.80 (m, 4H), 6.96 (d, J=5.2, 1H), 7.43 (d, J=5.1, 2H), 7.62 (d 1H J=5.2), 7.77 (d, J=5.2, 1H).

Example 82

Preparation of (2S) 2-N-(4-Aminobenzenesulfonyl)-2-N-isobutyl-6-N-(N'-benzyl-N'-piperonylaminocarbonyl)-2,6-diaminohexanol The title compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-benzyl-piperonylamine (1.1 molar excess). The preparation of the amine was done as described in general procedure F. The final product was purified by preparative HPLC to yield 8.0 mg (10%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.56–3.66 (m, 3H), 4.37 (s, 2H), 4.47 (s, 2H), 5.96 (s, 2H), 6.75 (m, 2H), 6.96 (d, J=5.2, 1H), 7.11–7.35 (m 4H), 7.43 (d, J=5.1, 2H), 7.62 (d 1H J=5.2), 7.77 (d, J=5.2, 1H).

Example 83

Preparation of (2S) 2-N-(4-Aminobenzenesulfonyl)-2-N-isobutyl-6-N-[N'-(4-methoxybenzyl)-N'-piperonylaminocarbonyl]-2,6-diaminohexanol The title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-4-methoxybenzylpiperonylamine (1.1 molar excess). The preparation of the amine was done as described in general procedure F. The final product was purified by preparative HPLC to yield 7.0 mg (8%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.56–3.66 (m, 3H), 3.71 (s 3H), 4.37 (s, 2H), 4.47 (s, 2H), 5.96 (s, 2H), 6.75–6.80 (m, 4H), 6.96 (d, J=5.2, 1H), 7.22 (d, J=5.2, 1H), 7.77 (d, J=5.2, 1H).

Example 84

Preparation of (2S) 2-N-(4-Aminobenzenesulfonyl)-2-N-isobutyl-6-N-[N'-(4-nitrobenzyl)-N'-piperonylaminocarbonyl]-2,6-diaminohexanol The title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-4-nitrobenzylpiperonylamine (1.1 molar excess). The preparation of the amine was done as described in general procedure F. The final product was purified by preparative HPLC to yield 6.0 mg (6%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H), 3.56–3.66 (m, 3H), 4.37 (s, 2H), 4.77 (s, 2H), 5.96 (s, 2H), 6.75–6.80 (m, 4H), 6.96 (d, J=5.2, 1H), 7.82 (d, J=7.2, 2H), 8.35 (d, J=7.2, 2H).

Example 85

Preparation of (2S) 2-N-(4-Aminobenzenesulfonyl)-2-N-isobutyl-6-N-(N',N'-dipiperonylaminocarbonyl)-2,6-diaminohexanol The title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared dipiperonylamine (1.1 molar excess). The preparation of the amine was done as described in general procedure F. The final product was purified by preparative HPLC to yield 5.0 mg (6%) of the desired material.

$^1$H NMR (CDCl$_3$): δ 0.83 (d, J=6.9, 6H), 1.08–1.71 (m, 2H), 1.23–1.45 (m, 3H), 1.65–1.72 (m, 1H), 1.89–1.99 (m, 1H), 2.84–2.99 (m, 2H), 3.09–3.2 (m, 2H) 3.56–3.66 (m, 3H), 4.35 (s, 2H), 4.38 (s, 2H), 5.96 (s, 2H), 6.00 (s, 2H), 6.75–6.80 (m, 6H), 6.96 (d, J=5.2, 2H).

Example 86

Preparation of (2S) 2-N-(4-Aminobenzenesulfonyl)-2-N-(3-methylbutyl)-6-N-(N'-N'-dibenzylaminocarbonyl)-2,6-diaminohexanol The title derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol (itself prepared as described for the preparation of the isobutyl analogue) as described in general procedure C using commercially available dibenzylamine (1.1 molar excess). The starting material was prepared in the same way as the compound XVIII. The final product was purified by preparative HPLC to yield 2.0 mg (10%).

LC-MS: 581.5 (M+H)$^+$, 98% pure. $^1$H NMR (CD$_3$OD): δ 0.88 (d, J=6.8, 6H), 0.97 (m, 1H), 1.08–1.18 (2m, 2H), 1.29–1.60 (#m, 8H), 3.09 (m, 1H), 3.17 (m, 3H), 3.42 (dd, J=7.2 and 10.7, 1H), 3.49 (dd, J=5.6 and 10.7, 1H), 3.62 (m, 1H), 4.47 (s, 4H), 4.55 (s, 1H), 6.67 (d, J=9.0, 2H), 7.21 (d, J=7.4, 4H), 7.26 (t, J=6.9, 2H), 7.33 (t, J=7.3, 4H), 7.49 (d, J=8.9, 2H).

Example 87

Preparation of (2S) 2-N-(4-Aminobenzenesulfonyl)-2-N-(3-methylbutyl)-6-N-[N'-(2-thiophenemethyl)-N'-piperonylaminocarbonyl]-2,6-diaminohexanol This compound was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(2-thiophenemethyl)piperonylamine (1.1 molar excess). The preparation of the amine was done as described in general procedure F. The starting material was prepared in the same way as the compound XVIII. The final product was purified by preparative HPLC to yield 5.0 mg (2%).

LC-MS: 631.4 (M+H)$^+$, 98% pure. $^1$H NMR (DMSO-d$_6$): δ 0.83 (d, J=6.0, 6H), 1.07–1.54 (#m, 12H), 2.95 (m, 1H), 3.02 (m, 3H), 3.28 (m, 3H), 4.27 (s, 2H), 4.48 (s, 2H), 5.98 (s, 2H), 6.48 (m, 1H), 6.58 (d, J=8.4, 2H), 6.67 (d, J=8.0, 1H), 6.74 (s, 1H), 6.85 (d, J=7.9, 1H), 6.93 (d, J=5.2, 2H), 7.40 (d, J=8.1, 3H).

N-(2-thiophenemethyl)piperonylamine: $^1$H NMR (DMSO-d$_6$): δ 4.04 (s, 2H), 4.31 (s, 2H), 6.05 (s, 2H), 6.95 (d, J=7.3, 1H), 6.99 (d, J=7.8, 1H), 7.10 (d, J=3.7, 1H), 7.18 (s, 1H), 7.35 (d, J=3.1, 1H), 7.62 (d, J=5.1, 1H), 9.70 (br s, 2H).

Example 88

Preparation of (2S) 2-N-(4-Aminobenzenesulfonyl)-2-N-(3-methylbutyl)-6-N-[N'-(4-methoxybenzyl)-N'-piperonylaminocarbonyl]-2,6-diaminohexanol This product was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-methoxybenzyl)piperonylamine (1.1 molar excess). The preparation of the amine was done as described in general procedure F. The starting material was prepared in the same way as the compound XVIII. The final product was purified by preparative HPLC to yield 4.0 mg (2%).

LC-MS: 655.4 (M+H)$^+$, 98% pure. $^1$H NMR (DMSO-d$_6$): δ 0.82 (d, J=6.0, 6H), 1.07–1.54 (#m, 12H), 2.93 (m, 1H), 3.01 (m, 3H), 3.51 (m, 1H), 3.72 (s, 3H), 4.22 (s, 2H), 4.26 (s, 2H), 4.61 (t, J=5.0, 1H), 5.97 (s, 2H), 6.41 (m, 1H), 6.58 (d, J=8.3, 2H), 6.64 (d, J=7.8, 1H), 6.71 (s, 1H), 6.84 (d, J=7.8, 1H), 6.88 (d, J=8.3, 2H), 7.10 (d, J=8.3, 2H), 7.40 (d, J=8.3, 2H).

N-(4-methoxybenzyl)piperonylamine: $^1$H NMR (DMSO-d$_6$): δ 3.58 (s, 4H), 3.72 (s, 3H), 5.97 (s, 2H), 6.74 (d, J=7.8, 1H), 6.81 (d, J=7.8, 1H), 6.87 (d, J=8.3, 2H), 6.90 (s, 1H), 7.21 (m, 2H).

Example 89

Preparation of (2S) 2-N-(4-Aminobenzenesulfonyl)-2-N-(3-methylbutyl)-6-N-[N'-(4-nitrobenzyl)-N'-piperonylaminocarbonyl]-2,6-diaminohexanol This derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-nitrobenzyl)piperonylamine (1.1 molar excess). The preparation of the amine was done as described in general procedure F. The starting material was prepared in the same way as the compound XVIII. The final product was purified by preparative HPLC to yield 6.0 mg (3%).

LC-MS: 670.4 (M+H)$^+$, 95% pure. $^1$H NMR (DMSO-d$_6$): δ 0.82 (d, J=6.0, 6H), 1.07–1.54 (#m, 12H), 2.93 (m, 1H), 3.02 (m, 3H), 3.27 (m, 3H), 4.33 (s, 2H), 4.49 (s, 2H), 5.97 (s, 2H), 6.58 (m, 3H), 6.67 (d, J=7.45, 1H), 6.75 (s, 1H), 6.84 (d, J=7.3, 1H), 7.41 (t, J=8.0, 4H), 8.18 (d, J=8.2, 2H).

N-(4-nitrobenzyl)piperonylamine: $^1$H NMR (DMSO-d$_6$): δ 3.60 (s, 2H), 3.77 (s, 2H), 5.97 (s, 2H), 6.77 (d, J=8.0, 1H), 6.83 (d, J=8.1, 1H), 6.93 (s, 1H), 7.62 (d, J=8.3, 2H), 8.18 (d, J=8.6, 2H).

Example 90

Preparation of (2S) 2-N-(4-Aminobenzenesulfonyl)-2-N-isobutyl-6-N-[N'-(4-trifluoromethylbenzyl)-N'-(2,3-methylenedioxy)benzylaminocarbonyl]-2,6-diaminohexanol This compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-(4-trifluoromethylbenzyl)-2,3-methylenedioxybenzylamine (1.1 molar excess). The preparation of the amine was done as described in general procedure F. The final product was purified by preparative HPLC to yield 13.0 mg (11%).

LC-MS: 679,4 (M+H)$^+$, 98% pure. $^1$H NMR (DMSO-d$_6$): δ 0.81 (d, J=6.8, 6H), 1.03 (m, 1H), 1.14 (m, 1H), 1.24–1.32 (2m, 4H), 1.53 (m, 1H), 1.85 (m, 1H), 2.73 (dd, J=7.1 and 14.2, 1H), 2.84 (dd, J=7.8 and 14.3, 1H), 2.99 (m, 2H), 3.24 (m, 2H), 3.46 (m, 1H), 4.36 (s, 2H), 4.48 (s, 2H), 4.60 (m, 1H), 5.94 (s, 2H), 6.58 (m, 3H), 6.69 (m, 1H), 6.80 (d, J=4.2, 2H), 7.39 (m, 4H), 7.66 (d, J=7.6, 2H).

N-(4-trifluoromethylbenzyl)-2,3-methylenedioxybenzylamine: $^1$H NMR (DMSO-d$_6$): δ 4.10 (s, 2H), 4.28 (s, 2H), 6.06 (s, 2H), 6.89 (t, J=7.6, 1H), 6.96 (d, J=7.8, 1H), 7.11 (d, J=7.9, 1H), 7.80 (s, 4H), 9.87 (br s, 1H).

Example 91

Preparation of (2S) 2-N-(4-Aminobenzenesulfonyl)-2-N-isobutyl-6-N-[N'-benzyl-N'-(2,3-methylenedioxy)benzylaminocarbonyl]-2,6-diaminohexanol This title derivative was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-benzyl-2,3-methylenedioxybenzylamine (1.1 molar excess). The preparation of the amine was done as described in general procedure F. The final product was purified by preparative HPLC to yield 16.0 mg (16%).

LC-MS: 611.5 (M+H)$^+$, 98% pure. $^1$H NMR (DMSO-d$_6$): δ 0.79 (d, J=6.0, 6H), 0.98 (m, 1H), 1.08 (m, 1H), 1.20–1.28 (2m, 4H), 1.49 (m, 1H), 1.81 (m, 1H), 2.70 (dd, J=7.3 and 14.4, 1H), 2.82 (dd, J=7.5 and 14.3, 1H), 2.96 (m, 2H), 3.21 (m, 2H), 3.42 (m, 1H), 4.29 (s, 2H), 4.35 (s, 2H), 4.56 (m, 1H), 5.91 (s, 2H), 6.45 (m, 1H), 6.55 (d, J=8.2, 2H), 6.65 (t, J=4.8, 1H), 6.77 (d, J=4.6, 2H), 7.14 (d, J=7.3, 2H), 7.20 (t, J=7.1, 1H), 7.28 (t, J=7.2, 2H), 7.35 (d, J=8.7, 2H).

N-benzyl-2,3-methylenedioxybenzylamine $^1$H NMR (DMSO-d$_6$): δ 3.64 (s, 2H), 3.69 (s, 2H), 5.97 (s, 2H), 6.80 (m, 2H), 6.91 (m, 1H), 7.22 (t, J=6.8, 1H), 7.31 (m, 4H), Example 92

Preparation of (2S) 2-N-(4-Aminobenzenesulfonyl)-2-N-isobutyl-6-N-[N'-(4-trifluoromethylbenzyl)-N'-piperonylaminocarbonyl]-2,6-diaminohexanol This product was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-(4-trifluoromethylbenzyl)piperonylamine (1.1 molar excess). The preparation of the amine was done as described in general procedure F. The final product was purified by preparative HPLC to yield 17.0 mg (14%).

LC-MS: 679.4 (M+H)$^+$, 98% pure. $^1$H NMR (DMSO-d$_6$): δ 0.80 (d, J=6.7, 6H), 1.02 (m, 1H), 1.12 (m, 1H), 1.23–1.30 (2m, 4H), 1.51 (m, 1H), 1.83 (m, 1H), 2.73 (dd, J=6.9 and 14.3, 1H), 2.84 (dd, J=7.6 and 14.3, 1H), 2.99 (m, 2H), 3.22 (m, 2H), 3.46 (m, 1H), 4.30 (s, 2H), 4.44 (s, 2H), 4.56 (m, 2H), 5.97 (s, 2H), 6.51 (m, 1H), 6.58 (d, J=8.6, 2H), 6.66 (d, J=7.5, 1H), 6.74 (s, 1H), 6.84 (d, J=8.4, 1H), 7.38 (t, J=7.9, 4H), 7.67 (d, J=7.8, 2H).

N-(4-trifluoromethylbenzyl)piperonylamine: $^1$H NMR (DMSO-d$_6$): δ 4.08 (br s, 2H), 4.20 (br s, 2H), 6.04 (s, 2H), 6.94 (d, J=7.5, 1H), 7.02 (d, J=7.9, 1H), 7.22 (s, 1H), 7.79 (s, 4H), 9.86 (br s, 2H).

Example 93

Preparation of (2S) 2-N-(4-Aminobenzenesulfonyl)-2-N-isobutyl-6-N-[N'-benzyl-N'-(2,4-difluorobenzyl)aminocarbonyl]-2,6-diaminohexanol This compound was prepared from solid phase bound (2S) 2-N-(4-aminobenzenesulfonyl)-2-N-isobutyl-6-N-(9-fluorenylmethoxycarbonyl)-2,6-diaminohexanol (XVIII) (example 65, step D) as described in general procedure C using freshly prepared N-benzyl-2,4-difluorobenzylamine (1.1 molar excess). The preparation of the amine was done as described in general procedure F. The final product was purified by preparative HPLC to yield 28.0 mg (26%).

LC-MS: 603.5 (M+H)$^+$, 96% pure. $^1$H NMR (DMSO-d$_6$): δ 0.82 (m, 6H), 1.09–1.31 (#m, 6H), 1.53 (m, 1H), 1.85 (m, 1H), 2.86 (m, 1H), 2.98 (m, 2H), 3.23 (m, 1H), 3.31 (m, 1H), 3.47 (m, 1H), 4.39 (d, J=7.2, 4H), 6.58 (m, 3H), 7.05 (m, 1H), 7.17 (d, J=7.3, 3H), 7.23 (m, 2H), 7.30 (d, J=7.1, 2H), 7.38 (d, J=8.3, 2H), 7.70 (s, 1H).

N-benzyl-2,4-difluorobenzylamine: $^1$H NMR (DMSO-d$_6$): δ 4.15 (t, J=5.5, 2H), 4.20 (t, J=5.5, 2H), 7.20 (m, 1H), 7.36 (m, 1H), 7.44 (d, J=6.9, 3H), 7.60 (d, J=2.2, 2H), 7.83 (q, J=6.7 & 15.2, 1H), 9.92 (s, 2H).

Example 94

Preparation of (2S) 2-N-(4-Aminobenzenesulfonyl)-2-N-(3-methylbutyl)-6-N-[N'-(4-trifluoromethylbenzyl)-N'-piperonylaminocarbonyl]-2,6-diaminohexanol This derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-trifluoromethylbenzyl)piperonylamine (1.1 molar excess). The preparation of the amine was done as described in general procedure F. The starting material was prepared in the same way as the compound XVIII. The final product was purified by preparative HPLC to yield 8.0 mg (4%).

LC-MS: 693.5 (M+H)$^+$, 98% pure. $^1$H NMR (DMSO-d$_6$): δ 0.81 (m, 6H), 1.06–1.53 (#m, 12H), 2.93 (m, 1H), 3.02 (m, 3H), 3.25 (m, 2H), 4.30 (s, 2H), 4.43 (s, 2H), 5.97 (s, 2H), 6.53 (m, 1H), 6.58 (d, J=8.4, 2H), 6.66 (d, J=7.7, 1H), 6.74 (s, 1H), 6.84 (d, J=7.6, 1H), 7.38 (m, 4H), 7.67 (d, J=8.0, 2H).

N-(4-trifluoromethylbenzyl)piperonylamine: see example 92.

Example 95

Preparation of (2S) 2-N-(4-Aminobenzenesulfonyl)-2-N-(3-methylbutyl)-6-N-[N'-(4-picolyl)-N'-piperonylaminocarbonyl]-2,6-diaminohexanol This product was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-picolyl)piperonylamine (1.1 molar excess). The preparation of the amine was done as described in general procedure F. The starting material was prepared in the same way as the compound XVIII. The final product was purified by preparative HPLC to yield 7.0 mg (3%).

LC-MS 626.5 (M+H)$^+$, 90% pure. $^1$H NMR (DMSO-d$_6$): δ 0.82 (d, J=6.4, 6H), 0.90 (m, 1H), 1.09–1.55 (#m, 12H), 2.93 (m, 1H), 3.02 (m, 3H), 3.25 (m, 1H), 3.66 (m, 1H), 4.38 (s, 2H), 4.51 (s, 2H), 5.98 (s, 2H), 6.59 (d, J=8.3, 2H), 6.64 (m, 1H), 6.68 (d, J=7.9, 1H), 6.78 (s, 1H), 6.84 (d, J=7.7, 1H), 7.40 (d, J=8.4, 2H), 7.46 (m, 2H), 8.64 (br s, 2H).

N-(4-picolyl)piperonylamine: 4.23 (s, 2H), 4.30 (s, 2H), 6.01 (s, 2H), 6.90 (d, J=7.4, 1H), 7.00 (s, 1H), 7.02 (d, J=5.8, 1H), 7.55 (d, J=5.2, 2H), 8.63 (d, J=5.1, 2H).

Example 96

Preparation of (2S) 2-N-(4-Aminobenzenesulfonyl)-2-N-(3-methylbutyl)-6-N-[N'-benzyl-N'-(2,3-methylenedioxy)benzylaminocarbonyl]-2,6-diaminohexanol This compound was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-benzyl-2,3-methylenedioxybenzylamine (1.1 molar excess). The preparation of the amine was done as described in general procedure F. The starting material was prepared in the same way as the compound XVIII. The final product was purified by preparative HPLC to yield 5.0 mg (3%).

LC-MS 625.4 (M+H)$^+$, 98% pure. $^1$H NMR (DMSO-d$_6$): δ 0.82 (d, J=6.2, 6H), 0.91 (m, 1H), 1.08–1.53 (#m, 12H), 2.94 (m, 1H), 3.02 (m, 3H), 3.51 (m, 2H), 4.32 (s, 2H), 4.39 (s, 2H), 5.95 (s, 2H), 6.49 (m, 1H), 6.59 (d, J=8.4, 2H), 6.69 (m, 1H), 6.80 (d, J=4.0, 2H), 7.17 (d, J=7.2, 2H), 7.23 (m, 1H), 7.31 (t, J=7.2, 2H), 7.40 (d, J=8.3, 2H).

N-benzyl-2,3-methylenedioxybenzylamine see example 91.

Example 97

Preparation of (2S) 2-N-(4-Aminobenzenesulfonyl)-2-N-(2-methylbutyl)-6-N-[N'-benzyl-N'-(2,3-methylenedioxy)benzylaminocarbonyl]-2,6-diaminohexanol This derivative was prepared from solid phase bound (2S) 2-N-(4-aminobenzenesulfonyl)-2-N-(2-methylbutyl)-6-N-

(9-fluorenylmethoxycarbonyl)-2,6-diaminohexanol (itself prepared as described for the preparation of the isobutyl analogue) as described in general procedure C using freshly prepared N-benzyl-2,3-methylenedioxybenzylamine (1.1 molar excess). The preparation of the amine was done as described in general procedure F. The starting material was prepared in the same way as the compound XVIII. The final product was purified by preparative HPLC to yield 16.0 mg (27%).

LC-MS: 625.4 (M+H)$^+$, 90% pure. $^1$H NMR (DMSO-d$_6$): δ 0.80 (m, 6H), 0.93–1.00 (m, 4H), 1.23–1.61 (#m, 6H), 2.85 (m, 2H), 2.95 (m, 2H), 3.24 (m, 1H), 3.31 (m, 1H), 3.46 (m, 2H), 4.31 (s, 2H), 4.38 (s, 2H), 5.94 (s, 2H), 6.47 (m, 1H), 6.59 (d, J=8.3, 2H), 6.62 (s, 1H), 6.68 (m, 1H, 6.80 (d, J=4.0, 1H), 7.17 (d, J=7.4, 2H), 7.23 (m, 1H), 7.31 (m, 2H), 7.37 (m, 2H).

N-benzyl-2,3-methylenedioxybenzylamine: see example 91.

Example 98

Preparation of (2S) 2-N-(4-Aminobenzenesulfonyl)-2-N-(2-methylbutyl)-6-N-[N'-benzyl-N'-piperonylaminocarbonyl]-2,6-diaminohexanol This product was prepared from solid phase bound (2S) 2-N-(4-aminobenzenesulfonyl)-2-N-(2-methylbutyl)-6-N-(9-fluorenylmethoxycarbonyl)-2,6-diaminohexanol as described in general procedure C using freshly prepared N-benzyl-piperonylamine (1.1 molar excess). The preparation of the amine was done as described in general procedure F. The starting material was prepared in the same way as the compound XVIII. The final product was purified by preparative HPLC to yield 22.0 mg (35%).

LC-MS: 624.4 (M+H)$^+$, 85% pure. $^1$H NMR (DMSO-d$_6$): δ 0.80 (m, 6H), 0.95–1.07 (m, 4H), 1.23–1.61 (#m, 6H), 2.74 (m, 1H), 2.81 (m, 2H), 2.97 (m, 2H), 3.23 (m, 1H), 3.31 (m, 1H), 3.47 (m, 2H), 4.25 (s, 2H), 4.34 (s, 2H), 5.97 (s, 2H), 6.42 (m, 1H), 6.61 (m, 3H), 6.73 (s, 1H), 6.83 (d, J=7.9, 1H), 7.16 (d, J=7.3, 2H), 7.24 (m, 1H), 7.32 (m, 2H), 7.37 (d, J=8.1, 2H).

N-benzyl-piperonylamine: $^1$H NMR (DMSO-d$_6$): δ 4.25 (s, 2H), 4.35 (s, 2H), 5.97 (s, 2H), 6.68 (m, 1H), 6.70 (s, 1H), 6.8 (d, J=7.9, 1H), 7.16 (d, J=7.3, 2H), 7.24 (m, 1H), 7.32 (m, 2H).

Example 99

Preparation of (2S) 2-N-(4-Aminobenzenesulfonyl)-2-N-(2-methylbutyl)-6-N-[N'-(2-thiophenemethyl)-N'-piperonylaminocarbonyl]-2,6-diaminohexanol This compound was prepared from solid phase bound (2S) 2-N-(4-aminobenzenesulfonyl)-2-N-(2-methylbutyl)-6-N-(9-fluorenylmethoxycarbonyl)-2,6-diaminohexanol as described in general procedure C using freshly prepared N-(2-thiophenemethyl)piperonylamine (1.1 molar excess). The preparation of the amine was done as described in general procedure F. The starting material was prepared in the same way as the compound XVIII. The final product was purified by preparative HPLC to yield 13.0 mg (21%).

LC-MS: 631.4 (M+H)$^+$, 50% pure. $^1$H NMR (Acetone-d$_6$): δ 0.88 (m, 6H), 1.05–1.29 (m, 3H), 1.34–1.85 (#m, 7H), 2.80–3.71 (#m, 9H), 4.40 (s, 2H), 4.62 (s, 2H), 5.98 (s, 2H), 6.77 (m, 4H), 6.96 (m, 2H), 7.35 (d, J=5.01, 1H), 7.52 (m, 3H), 7.77 (m, 1H).

N-(2-thiophenemethyl)piperonylamine: see example 87.

Example 100

Preparation of (2S) 2-N-(4-Aminobenzenesulfonyl)-2-N-(2-methylbutyl)-6-N-[N'-(4-methoxybenzyl)-N'-piperonylaminocarbonyl]-2,6-diaminohexanol This title derative was prepared from solid phase bound (2S) 2-N-(4-aminobenzenesulfonyl)-2-N-(2-methylbutyl)-6-N-(9-fluorenylmethoxycarbonyl)-2,6-diaminohexanol as described in general procedure C using freshly prepared N-(4-methoxybenzyl)piperonylamine (1.1 molar excess). The preparation of the amine was done as described in general procedure F. The starting material was prepared in the same way as the compound XVIII. The final product was purified by preparative HPLC to yield 13.0 mg (20%).

LC-MS: 655.5 (M+H)$^+$, 50% pure. $^1$H NMR (Acetone-d$_6$): δ 0.88 (m, 6H), 1.02–1.22 (m, 3H), 1.29–1.73 (#m, 7H), 2.77–3.16 (#m, 5H), 3.45 (m, 1H), 3.57 (m, 2H), 3.78 (s, 3H), 4.38 (s, 2H), 4.40 (s, 2H), 5.97 (s, 2H), 6.76 (m, 5H), 6.89 (d, J=8.1, 2H), 7.18 (d, J=8.2, 2H), 7.50 (m, 4H).

N-(4-methoxybenzyl)piperonylamine: see example 88.

Example 101

Preparation of (2S) 2-N-(4-Aminobenzenesulfonyl)-2-N-(3-methylbutyl)-6-N-[N'-benzyl-N'-piperonylaminocarbonyl]-2,6-diaminohexanol This product was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-benzyl-piperonylamine (1.1 molar excess). The preparation of the amine was done as described in general procedure F. The starting material was prepared in the same way as the compound XVIII. The final product was purified by preparative HPLC to yield 2.0 mg (2%).

LC-MS 625.5 (M+H)$^+$, 99% pure. $^1$H NMR (DMSO-d$_6$): δ 0.82 (d, J=6.0, 6H), 1.06–1.55 (6m, 12H), 2.94 (m, 1H), 3.00 (m, 3H), 3.51 (m, 1H), 4.27 (s, 2H), 4.35 (s, 2H), 5.98 (s, 2H), 6.44 (m, 1H), 6.59 (d, J=8.3, 2H), 6.65 (d, J=7.9, 1H), 6.73 (s, 1H), 6.84 (d, J=8.1, 1H), 7.17 (d, J=7.9, 2H), 7.24 (t, J=7.5, 1H), 7.33 (t, J=7.5, 2H), 7.40 (d, J=8.4, 2H).

N-benzyl-piperonylamine: see example 98.

Example 102

Preparation of (2S) 2-N-(4-Aminobenzenesulfonyl)-2-N-(3-methylbutyl)-6-N-[N'-(4-fluorobenzyl)-N'-piperonylaminocarbonyl]-2,6-diaminohexanol This title derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-fluorobenzyl)piperonylamine (1.1 molar excess). The preparation of the amine was done as described in general procedure F. The starting material was prepared in the same way as the compound XVIII. The final product was purified by preparative HPLC to yield 9.0 mg (4%).

LC-MS: 643.4 (M+H)$^+$, 97% pure. $^1$H NMR (DMSO-d$_6$): δ 0.83 (d, J=6.0, 6H), 1.07–1.55 (#m, 10H), 1.76 (s, 1H), 2.94 (m, 1H), 3.06 (m, 3H), 3.28 (m, 2H), 4.26 (s, 2H), 4.33 (s, 2H), 5.98 (s, 2H), 6.46 (br s, 1H), 6.59 (d, J=8.3, 2H), 6.65 (d, J=7.9, 1H), 6.73 (s, 1H), 6.84 (d, J=8.1, 1H), 7.14 (m, 2H), 7.20 (m, 2H), 7.40 (d, J=8.4, 2H).

N-(4-fluorobenzyl)piperonylamine: $^1$H NMR (DMSO-d$_6$): δ 3.39 (s, 1H), 3.46 (s, 1H), 3.57 (s, 1H), 3.62 (s, 1H), 5.97 (s, 2H), 6.76 (d, J=7.7, 1H), 6.83 (m, 1H), 6.92 (s, 1H), 7.14 (m, 2H), 7.36 (m, 2H).

Example 103

Preparation of (2S) 2-N-(4-Aminobenzenesulfonyl)-2-N-(3-methylbutyl)-6-N-[N'-(4-fluorobenzyl)-N'-(3,4-ethylenedioxy)benzylaminocarbonyl]-2,6-diaminohexanol This compound was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-fluorobenzyl)-3,4-(ethylenedioxy)benzylamine (1.1 molar excess). The preparation of the amine was done as described in general procedure F. The starting material was prepared in the same way as the compound XVIII. The final product was purified by preparative HPLC to yield 14.0 mg (7%).

LC-MS: 657.5 (M+H)$^+$, 98% pure. $^1$H NMR (DMSO-d$_6$): δ 0.82 (d, J=6.7, 6H), 0.91 (m, 1H), 1.06–1.53 (#m, 10H), 2.93 (m, 1H), 3.01 (m, 3H), 3.27 (m, 2H), 4.20 (s, 4H), 4.22 (s, 2H), 4.31 (s, 2H), 6.44 (m, 1H), 6.58 (d, J=8.5, 2H), 6.64 (m, 2H), 6.78 (d, J=8.2, 1H), 7.13 (m, 2H), 7.20 (m, 2H), 7.40 (d, J=8.4, 2H).

N-(4-fluorobenzyl)-3,4-(ethylenedioxy)benzylamine: $^1$H NMR (DMSO-d$_6$): δ 4.01 (m, 1H), 4.10 (m, 2H), 4.20 (m, 1H), 4.25 (s, 4H), 6.88 (m, 1H), 6.97 (d, J=8.6, 1H), 7.07 (d, J=14.4, 1H), 7.25 (m, 2H), 7.59 (m, 2H), 9.49 (br s, 1H).

Example 104

Preparation of (2S) 2-N-(4-Aminobenzenesulfonyl)-2-N-(3-methylbutyl)-6-N-(N'-isobutyl-N'-piperonylaminocarbonyl)-2,6-diaminohexanol This product was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-isobutyl-piperonylamine (1.1 molar excess). The preparation of the amine was done as described in general procedure F. The starting material was prepared in the same way as the compound XVIII. The final product was purified by preparative HPLC to yield 5.0 mg (3%).

LC-MS: 591.5 (M+H)$^+$, 98% pure. $^1$H NMR (DMSO-d$_6$): δ 0.82 (m, 14H), 0.91 (d, J=6.5, 2H), 1.06–1.48 (#m, 10H), 1.84 (m, 1H), 2.90 (d, J=7.4, 2H), 2.93 (m, 2H), 3.09 (m, 1H), 3.25 (m, 2H), 4.32 (s, 2H), 5.96 (s, 2H), 6.19 (m, 1H), 6.58 (d, J=8.5, 2H), 6.65 (d, J=7.9, 1H), 6.73 (s, 1H), 6.83 (d, J=7.3, 1H), 7.39 (d, J=8.3, 2H).

N-isobutyl-piperonylamine: $^1$H NMR (DMSO-d$_6$): δ 0.92 (d, J=6.6, 6H), 2.66 (m, 2H), 4.03 (t, J=5.0, 2H), 6.05 (s, 2H), 6.95 (d, J=7.7, 1H), 7.01 (d, J=7.5, 1H), 7.18 (s, 1H), 8.95 (br s, 2H).

Example 105

Preparation of (2S) 2-N-(4-Aminobenzenesulfonyl)-2-N-(3-methylbutyl)-6-N-[N'-(3-methoxybenzyl)-N'-piperonylaminothiocarbonyl]-2,6-diaminohexanol This compound was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(3-methoxybenzyl)piperonylamine (1.1 molar excess). The preparation of the amine was done as described in general procedure F. The starting material was prepared in the same way as the compound XVIII. The final product was purified by preparative HPLC to yield 12.0 mg (6%).

LC-MS: 671.5 (M+H)$^+$, 60% pure. $^1$H NMR (DMSO-d$_6$): δ 0.82 (d, J=6.3, 6H), 0.90 (m, 1H), 1.00–1.19 (2m, 2H), 1.23–1.51 (#m, 9H), 2.93 (m, 1H), 3.03 (m, 1H), 3.25 (m, 3H), 3.71 (s, 3H), 4.80 (s, 4H), 5.98 (s, 2H), 6.58 (d, J=8.4, 2H), 6.69 (d, J=7.9, 1H), 6.74 (m, 2H), 6.82 (m, 2H), 6.86 (d, J=8.1, 1H), 7.25 (t, J=7.7, 1H), 7.39 (d, J=8.5, 2H).

N-(3-methoxybenzyl)piperonylamine: $^1$H NMR (DMSO-d$_6$): δ 3.77 (s, 4H), 4.04 (m, 3H), 4.17 (m, 1H), 6.05 (s, 2H), 6.94 (d, J=7.5, 2H), 7.00 (d, J=8.0, 1H), 7.07 (d, J=7.5, 1H), 7.20 (d, J=8.7, 1H), 7.32 (q, J=8.2 & 16.2, 2H), 9.65 (br s, 1H).

Example 106

Preparation of (2S) 2-N-(4-Aminobenzenesulfonyl)-2-N-(3-methylbutyl)-6-N-[N'-(3,4-dimethoxybenzyl)-N'-piperonylaminothiocarbonyl]-2,6-diaminohexanol This title derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(3,4-dimethoxybenzyl)piperonylamine (1.1 molar excess). The preparation of the amine was done as described in general procedure F. The starting material was prepared in the same way as the compound XVIII. The final product was purified by preparative HPLC to yield 7.0 mg (3%).

LC-MS: 701.5 (M+H)$^+$, 80% pure. $^1$H NMR (DMSO-d$_6$): δ 0.82 (d, J=6.0, 6H), 1.03–1.15 (2m, 2H), 1.23–1.51 (#m, 9H), 2.92 (m, 1H), 3.04 (m, 1H), 3.24 (m, 2H), 3.44 (m, 2H), 3.50 (m, 1H), 3.68 (s, 3H), 3.72 (s, 3H), 4.66 (br s, 1H), 4.76 (s, 2H), 4.80 (s, 2H), 5.99 (s, 2H), 6.58 (d, J=8.3, 2H), 6.70 (d, J=7.3, 2H), 6.81 (s, 2H), 6.87 (d, J=8.2, 1H), 6.91 (d, J=8.4, 1H), 7.40 (d, J=8.3, 1H), 7.58 (br s, 1H).

N-(3,4-dimethoxybenzyl)piperonylamine: $^1$H NMR (DMSO-d$_6$): δ 3.75 (d, J=7.4, 6H), 3.99 (br s, 4H), 6.04 (s, 2H), 6.94 (m, 2H), 7.00 (d, J=5.8, 2H), 7.22 (s, 1H), 7.31 (s, 1H), 9.72 (br s, 2H).

Example 107

Preparation of (2S) 2-N-(4-Aminobenzenesulfonyl)-2-N-(3-methylbutyl)-6-N-[N'-(3,4,5-trimethoxybenzyl)-N'-piperonylaminothiocarbonyl]-2,6-diaminohexanol This product was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(3,4,5-trimethoxybenzyl)piperonylamine (1.1 molar excess). The preparation of the amine was done as described in general procedure F. The starting material was prepared in the same way as the compound XVIII. The final product was purified by preparative HPLC to yield 10.0 mg (5%).

LC-MS: 731.5 (M+H)$^+$, 60% pure. $^1$H NMR (DMSO-d$_6$): δ 0.83 (d, J=6.0, 6H), 0.90 (m, 1H), 1.02–1.46 (#m, 11H), 2.92 (m, 1H, 3.03 (m, 2H), 3.24 (m, 2H), 3.62 (s, 3H), 3.70 (s, 6H), 4.78 (s, 2H), 4.83 (s, 2H), 5.99 (s, 2H), 6.48 (s, 2H), 6.59 (d, J=9.2, 2H), 6.71 (d, J=7.6, 1H, 6.86 (m, 2H), 7.39 (d, J=8.3, 2H), 7.60 (m, 1H).

N-(3,4,5-trimethoxybenzyl)piperonylamine: $^1$H NMR (DMSO-d$_6$): δ 3.66 (s, 3H), 3.78 (s, 6H), 4.02 (m, 4H), 6.04 (s, 2H), 6.95 (d, J=7.5, 1H), 7.00 (d, J=7.7, 1H), 7.19 (s, 1H), 9.59 (br s, 2H).

Example 108

Preparation of (2S) 2-N-(4-Aminobenzenesulfonyl)-2-N-(3-methylbutyl)-6-N-[N'-(4-fluorobenzyl)-N'-(3, 4-ethylenedioxy)benzylaminothiocarbonyl]-2,6-dianinohexanol This derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-fluorobenzyl)-3,4-ethylenedioxybenzylamine (1.1 molar excess). The preparation of the amine was done as described in general procedure F. The starting material was prepared in the same way as the compound XVIII. The final product was purified by preparative HPLC to yield 16.0 mg (8%).

LC-MS: 673.4 (M+H)$^+$, 75% pure. $^1$H NMR (DMSO-d$_6$): δ 0.83 (d, J=6.5, 6H), 0.90 (m, 1H), 1.03–1.56 (#m, 8H), 2.93 (m, 1H), 3.03 (m, 1H), 3.26 (m, 2H), 3.44 (m, 2H), 3.48 (m, 1H), 4.21 (s, 4H), 4.73 (s, 2H), 4.85 (s, 2H), 6.59 (d, J=8.4, 2H), 6.66 (d, J=8.3, 1H), 6.70 (s, 1H), 6.81 (d, J=8.4, 1H), 7.16 (m, 2H), 7.24 (m, 2H), 7.40 (d, J=8.3, 2H), 7.64 (br s, 1H).

N-(4-fluorobenzyl)-3,4-ethylenedioxybenzylamine: see example 103.

Example 109

Preparation of (2S) 2-N-(4-Aminobenzenesulfonyl)-2-N-(3-methylbutyl)-6-N-[N'-(4-methoxybenzyl)-N'-piperonylaminothiocarbonyl]-2,6-diaminohexanol This compound was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(4-methoxybenzyl)piperonylamine (1.1 molar excess). The preparation of the amine was done as described in general procedure F. The starting material was prepared in the same way as the compound XVIII. The final product was purified by preparative HPLC to yield 11.0 mg (5%).

LC-MS: 671.5 (M+H)$^+$, 50% pure. $^1$H NMR (DMSO-d$_6$): δ 0.82 (d, J=6.6, 6H), 0.90 (m, 1H), 1.01–1.54 (#m, 11H), 2.93–3.06 (2m, 2H), 3.26 (m, 2H), 3.73 (s, 3H), 4.76 (br s, 4H), 5.99 (s, 2H), 6.58 (d, J=8.3, 2H), 6.68 (d, J=8.0, 1H), 6.79 (s, 1H), 6.88 (m, 3H), 7.13 (d, J=8.0, 2H), 7.40 (d, J=8.3, 2H), 7.60 (br s, 1H).

N-(4-methoxybenzyl)piperonylamine: see example 88.

Example 110

Preparation of (2S) 2-N-(4-Aminobenzenesulfonyl)-2-N-(3-methylbutyl)-6-N-[N'-(3-methoxybenzyl)-N'-piperonylaminocarbonyl]-2,6-diaminohexanol This title derivative was prepared from solid phase bound (2S) 2-N-(4-aminobenzenesulfonyl)-2-N-(3-methylbutyl)-6-N-(9-fluorenylmethoxycarbonyl)-2,6-diaminohexanol as described in general procedure C using freshly prepared N-(3-methoxybenzyl)piperonylamine (1.1 molar excess). The preparation of the amine was done as described in general procedure F. The starting material was prepared in the same way as the compound XVIII. The final product was purified by preparative HPLC to yield 7.0 mg (3%).

LC-MS: 655.5 (M+H)$^+$, 90% pure $^1$H NMR (DMSO-d$_6$): δ 0.82 (d, J=5.9, 6H), 1.05–1.56 (#m, 10H), 2.94 (m, 1H), 3.01 (m, 3H), 3.26 (m, 1H), 3.51 (m, 1H), 3.71 (s, 3H), 4.27 (s, 2H), 4.32 (s, 2H), 4.61 (t, J=4.7, 1H), 5.97 (s, 2H), 6.42 (t, J=4.6, 1H), 6.58 (d, J=8.3, 2H), 6.65 (d, J=7.9, 1H), 6.71 (s, 1H), 6.74 (d, J=7.6, 2H), 6.80 (d, J=8.6, 1H), 6.84 (d, J=8.1, 1H), 7.23 (t, J=8.1, 1H), 7.39 (d, J=8.4, 2H).

N-(3-methoxybenzyl)piperonylamine: see example 105.

Enzymatic Assay for Determining the Inhibition Constant (Ki) of Synthetic Compounds Targeting the HIV Protease This is a fluorometric assay based on the cleavage by protease of a substrate carrying a donor group (EDANS) and an acceptor group (DABCYL) on each side of the cleavage site, interacting together through fluorescence resonance energy transfer (FRET) as described by Matayoshi et al. (Science 247:954–954, 1990).

After calculation of Vo and Vi, the inhibition constant (Ki) of the compound is determined using the equation of Henderson:

$$\frac{Vo}{Vi} = 1 + \frac{[I]}{Ki_{app}} \quad \text{Where } Ki = \frac{Ki_{app}}{1 + \frac{[S]}{Km}}$$

where Vo=the enzyme's initial velocity

Vi=the enzyme velocity in the presence of the inhibitory compound,

[I]=inhibitor concentration, [S]=substrate concentration,

Km=Michaelis-Menten constant and Ki$_{app}$=apparent Ki

Graphs are traced and the Ki determined using GraphPad Prism software v. 3.0.

The compounds listed in Table 1 were prepared by following Scheme 1, 2, 3, 4, 5 or 6; and more particularly as described in each example listed above. The numbers of the compounds listed in Table 1 and Table 2 (Ex. No.) corresponds to the example numbers presented above. The activities of the compounds are also listed in the same tables demonstrating their potential usefulness. In Table 1 are shown compounds of formula I wherein Y, n, Cx, R$_1$, R$_2$, R$_3$, and R$_4$ are as presented in Table 1. Ki results for compounds of formula I are also presented in Table 1.

TABLE 1

Anti-protease activity of Nε-amino carbonyl substituted L-lysine derivatives and analogs

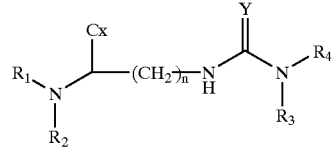

| Ex. No. | Cx | $R_1$ | $R_2$ | $R_3$ | $R_4$ | Y | n | Ki (nM) | D, L DL R, S, RS |
|---|---|---|---|---|---|---|---|---|---|
| 1 | COOH | 4-$CH_3C_6H_4SO_2$ | i-$C_4H_9$ | H | $C_6H_5CH_2CH_2$ | O | 4 | 204 | L |
| 2 | COOH | 4-$CH_3C_6H_4SO_2$ | i-$C_4H_9$ | H | $C_6H_5CH_2$ | O | 4 | 32 | L |
| 3 | COOH | 4-$CH_3C_6H_4SO_2$ | i-$C_4H_9$ | H | $C_6H_4N$-2-$CH_2$ | O | 4 | >300 | L |
| 4 | COOH | 4-$CH_3C_6H_4SO_2$ | i-$C_4H_9$ | H | 1-Indanyl (RS) | O | 4 | ND | S, RS |
| 5 | COOH | 4-$CH_3C_6H_4SO_2$ | i-$C_4H_9$ | H | 4-HO-$C_6H_4CH_2CH_2$ | O | 4 | >300 | L |
| 6 | COOH | 4-$CH_3C_6H_4SO_2$ | i-$C_4H_9$ | H | Indole-3-$CH_2CH_2$ | O | 4 | 40 | L |
| 7 | COOH | 4-$CH_3C_6H_4SO_2$ | i-$C_4H_9$ | i-$C_4H_9$ | Cyclohexyl | O | 4 | >300 | L |
| 8 | COOH | 4-$CH_3C_6H_4SO_2$ | i-$C_4H_9$ | H | $C_6H_5CH(CONH_2)$ | O | 4 | 60 | L, L |
| 9 | COOH | 4-$CH_3C_6H_4SO_2$ | i-$C_4H_9$ | H | $C_6H_5CH(CONH_2)$ | O | 4 | 131 | L, D |
| 10 | COOH | 4-$CH_3C_6H_4SO_2$ | i-$C_4H_9$ | H | 2-HO-$C_6H_4CONH$ | O | 4 | 55 | L |
| 11 | COOH | 4-$CH_3C_6H_4SO_2$ | i-$C_4H_9$ | H | $C_5H_4N$-4-$CONH$ | O | 4 | >300 | L |
| 12 | COOH | 4-$CH_3C_6H_4SO_2$ | i-$C_4H_9$ | H | $C_6H_5CH(CONH$-i-$C_4H_9)$ | O | 4 | 47 | L, L |
| 13 | COOH | 4-$CH_3C_6H_4SO_2$ | i-$C_4H_9$ | H | $C_6H_5CH(CONHC_6H_5)$ | O | 4 | 60 | L, L |
| 14 | COOH | 4-$CH_3C_6H_4SO_2$ | i-$C_4H_9$ | H | 1-Indanyl (RS) | S | 4 | >300 | S, RS |
| 15 | COOH | 4-$CH_3C_6H_4SO_2$ | i-$C_4H_9$ | H | Indole-3-$CH_2CH_2$ | S | 4 | 111 | L |
| 16 | COOH | 4-$CH_3C_6H_4SO_2$ | i-$C_4H_9$ | H | $C_6H_5CH_2$ | S | 4 | 152 | L |
| 17 | COOH | 4-$CH_3C_6H_4SO_2$ | i-$C_4H_9$ | H | $C_5H_{10}NCH_2CH_2$ | O | 4 | >300 | L |
| 18 | COOH | 4-$NH_2C_6H_4SO_2$ | i-$C_4H_9$ | H | $C_6H_5CH_2$ | O | 4 | 200 | L |
| 19 | $COOCH_3$ | 4-$CH_3C_6H_4SO_2$ | i-$C_4H_9$ | H | $C_5H_4N$-2-$CH_2CH_2$ | O | 4 | >300 | L |
| 20 | COOH | 4-$CH_3C_6H_4SO_2$ | i-$C_4H_9$ | H | 1-Isoquinolyl | O | 4 | >300 | L |
| 21 | COOH | 4-$CH_3C_6H_4SO_2$ | i-$C_4H_9$ | H | $C_6H_5CH_2CH_2$ | O | 4 | 167 | L |
| 22 | COOH | 4-$CH_3C_6H_4SO_2$ | i-$C_4H_9$ | H | 2-Hydroxy-1-indanyl | O | 4 | 300 | >S, R, S |
| 23 | COOH | 4-$CH_3C_6H_4SO_2$ | i-$C_4H_9$ | H | 2-Hydroxy-1-indanyl | O | 4 | >300 | S, S, R |
| 24 | COOH | 4-$CH_3C_6H_4SO_2$ | i-$C_4H_9$ | H | 1-Indanyl | O | 4 | 196 | S, R |
| 25 | COOH | 4-$CH_3C_6H_4SO_2$ | i-$C_4H_9$ | H | 1-Indanyl | O | 4 | >300 | S, S |
| 26 | COOH | 4-$CH_3C_6H_4SO_2$ | i-$C_4H_9$ | H | 1-Indanyl | O | 4 | >300 | R, S |
| 27 | COOH | 4-$CH_3C_6H_4SO_2$ | i-$C_4H_9$ | H | 1-Indanyl | O | 4 | >300 | R, R |
| 28 | COOH | 4-$CH_3C_6H_4SO_2$ | i-$C_4H_9$ | H | $C_6H_5CH_2$ | N—CN | 4 | 63 | L |
| 29 | COOH | 4-$CH_3C_6H_4SO_2$ | i-$C_4H_9$ | H | Indole-3-$CH_2CH_2$ | N—CN | 4 | 8.2 | L |
| 30 | COOH | 4-$CH_3C_6H_4SO_2$ | i-$C_4H_9$ | H | $C_6H_5CH_2$ | NH | 4 | >300 | DL |
| 31 | COOH | 4-$CH_3C_6H_4SO_2$ | i-$C_4H_9$ | $C_6H_5CH_2$ | $C_6H_5CH_2CH_2$ | O | 4 | >300 | L |
| 32 | COOH | 4-$CH_3C_6H_4SO_2$ | i-$C_4H_9$ | $C_6H_5CH_2$ | $C_6H_5CH_2$ | O | 4 | 7.2 | L |
| 33 | $CH_2OH$ | 4-$CH_3C_6H_4SO_2$ | i-$C_4H_9$ | $C_6H_5CH_2$ | $C_6H_5CH_2$ | O | 4 | 17 | S |
| 34 | $CH_2OH$ | 4-$CH_3C_6H_4SO_2$ | i-$C_4H_9$ | $C_6H_5CH_2$ | $C_6H_5CH_2$ | S | 4 | 78 | S |
| 35 | COOH | 4-$CH_3C_6H_4SO_2$ | i-$C_4H_9$ | i-$C_4H_9$ | i-$C_4H_9$ | O | 4 | >300 | L |
| 36 | COOH | 4-$NH_2C_6H_4SO_2$ | i-$C_4H_9$ | $C_6H_5CH_2$ | $C_6H_5CH_2$ | O | 4 | 1.8 | L |
| 37 | COOH | 4-$CH_3C_6H_4SO_2$ | i-$C_4H_9$ | $C_6H_5CH_2$ | $C_6H_5CH_2$ | S | 4 | 12 | L |
| 38 | COOH | 4-$CH_3C_6H_4SO_2$ | i-$C_4H_9$ | $C_6H_5CH_2$ | $C_5H_4N$-4-$CH_2$ | O | 4 | 3.7 | L |
| 39 | COOH | 4-$CH_3C_6H_4SO_2$ | i-$C_4H_9$ | $(CH_3)_2CH$ | $C_6H_5CH_2$ | O | 4 | 19 | L |
| 40 | COOH | 4-$CH_3C_6H_4SO_2$ | i-$C_4H_9$ | $CH_3$ | $C_6H_5CH_2$ | O | 4 | 55 | L |
| 41 | $CH_2OH$ | 4-$NH_2C_6H_4SO_2$ | i-$C_4H_9$ | $C_6H_5CH_2$ | $C_6H_5CH_2$ | O | 4 | 12 | S |
| 42 | COOH | 4-$CH_3C_6H_4SO_2$ | i-$C_4H_9$ | $C_6H_5CH_2$ | $C_5H_4N$-3-$CH_2$ | O | 4 | 3.7 | L |
| 43 | COOH | 4-$CH_3C_6H_4SO_2$ | i-$C_4H_9$ | 4-$CH_3OC_6H_4CH_2$ | $C_5H_4N$-4-$CH_2$ | O | 4 | 7.9 | L |
| 44 | COOH | 4-$CH_3C_6H_4SO_2$ | i-$C_4H_9$ | $C_5H_4N$-4-$CH_2$ | $C_5H_4N$-4-$CH_2$ | O | 4 | 187 | L |
| 45 | $CH_2OH$ | 4-$CH_3C_6H_4SO_2$ | i-$C_4H_9$ | 4-$CH_3OC_6H_4CH_2$ | $C_5H_4N$-4-$CH_2$ | O | 4 | 54 | S |
| 46 | $CH_2OH$ | 4-$CH_3C_6H_4SO_2$ | i-$C_4H_9$ | $C_6H_4N$-4-$CH_2$ | $C_5H_4N$-4-$CH_2$ | O | 4 | >300 | S |
| 47 | COOH | 4-$NH_2C_6H_4SO_2$ | i-$C_4H_9$ | $C_6H_5CH_2$ | $C_5H_4N$-3-$CH_2$ | O | 4 | 2.4 | L |
| 48 | COOH | 4-$NH_2C_6H_4SO_2$ | i-$C_4H_9$ | $C_6H_5CH_2$ | $C_5H_4N$-4-$CH_2$ | O | 4 | 12 | L |
| 49 | COOH | 4-$NH_2C_6H_4SO_2$ | i-$C_4H_9$ | 4-$CH_3OC_6H_4CH_2$ | $C_5H_4N$-4-$CH_2$ | O | 4 | 12 | L |
| 50 | $CH_2OH$ | 4-$NH_2C_6H_4SO_2$ | i-$C_4H_9$ | $C_6H_5CH_2$ | $C_5H_4N$-3-$CH_2$ | O | 4 | 34 | S |
| 51 | $CH_2OH$ | 4-$NH_2C_6H_4SO_2$ | i-$C_4H_9$ | $C_5H_4N$-4-$CH_2$ | $C_5H_4N$-4-$CH_2$ | O | 4 | >300 | S |
| 52 | $CH_2OH$ | 4-$NH_2C_6H_4SO_2$ | i-$C_4H_9$ | $C_6H_5CH_2$ | $C_5H_4N$-4-$CH_2$ | O | 4 | 90 | S |
| 53 | $CH_2OH$ | 4-$NH_2C_6H_4SO_2$ | i-$C_4H_9$ | 4-$CH_3OC_6H_4CH_2$ | $C_5H_4N$-4-$CH_2$ | O | 4 | 90 | S |
| 54 | COOH | 4-$CH_3C_6H_4SO_2$ | i-$C_4H_9$ | $C_6H_5CH_2$ | 2-$NO_2C_6H_4CH_2$ | O | 4 | 0.9 | L |
| 55 | COOH | 4-$CH_3C_6H_4SO_2$ | i-$C_4H_9$ | $C_6H_5CH_2$ | 3-$NO_2C_6H_4CH_2$ | O | 4 | 1.1 | L |
| 56 | COOH | 4-$CH_3C_6H_4SO_2$ | i-$C_4H_9$ | $C_6H_5CH_2$ | 4-$NO_2C_6H_4CH_2$ | O | 4 | 1.5 | L |
| 57 | COOH | 4-$CH_3C_6H_4SO_2$ | i-$C_4H_9$ | $C_6H_5CH_2$ | 2-$NH_2C_6H_4CH_2$ | O | 4 | 1.7 | L |
| 58 | COOH | 4-$CH_3C_6H_4SO_2$ | i-$C_4H_9$ | $C_6H_5CH_2$ | 3-$NH_2C_6H_4CH_2$ | O | 4 | >300 | L |
| 59 | $CH_2OH$ | 4-$CH_3C_6H_4SO_2$ | i-$C_4H_9$ | $C_6H_5CH_2$ | 2-$NO_2C_6H_4CH_2$ | O | 4 | 1.7 | S |
| 60 | $CH_2OH$ | 4-$CH_3C_6H_4SO_2$ | i-$C_4H_9$ | $C_6H_5CH_2$ | 3-$NO_2C_6H_4CH_2$ | O | 4 | 6.0 | S |
| 61 | $CH_2OH$ | 4-$CH_3C_6H_4SO_2$ | i-$C_4H_9$ | $C_6H_5CH_2$ | 4-$NO_2C_6H_4CH_2$ | O | 4 | 9.0 | S |
| 62 | $CH_2OH$ | 4-$CH_3C_6H_4SO_2$ | i-$C_4H_9$ | $C_6H_5CH_2$ | 2-$NH_2C_6H_4CH_2$ | O | 4 | 39 | S |
| 63 | $CH_2OH$ | 4-$CH_3C_6H_4SO_2$ | i-$C_4H_9$ | $C_6H_5CH_2$ | 3-$NH_2C_6H_4CH_2$ | O | 4 | 54 | S |
| 64 | $CH_2OH$ | 4-$CH_3C_6H_4SO_2$ | i-$C_4H_9$ | $C_6H_5CH_2$ | 4-$NH_2C_6H_4CH_2$ | O | 4 | 21 | S |

TABLE 1-continued

Anti-protease activity of Nε-amino carbonyl substituted L-lysine derivatives and analogs

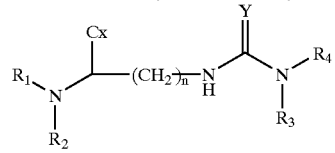

| Ex. No. | Cx | $R_1$ | $R_2$ | $R_3$ | $R_4$ | Y | n | Ki (nM) | D, L DL R, S, RS |
|---|---|---|---|---|---|---|---|---|---|
| 65 | $CH_2OH$ | $4-NH_2C_6H_4SO_2$ | $i-C_4H_9$ | H | 3-Indole-$CH_2CH(CO_2H)$ | O | 4 | >300 | S, S |
| 66 | $CH_2OH$ | $4-NH_2C_6H_4SO_2$ | $i-C_4H_9$ | $4-FC_6H_4CH_2$ | $C_6H_{11}$ | O | 4 | 175 | S |
| 67 | $CH_2OH$ | $4-NH_2C_6H_4SO_2$ | $i-C_4H_9$ | $4-FC_6H_4CH_2$ | Piperonyl | O | 4 | 2.0 | S |
| 68 | $CH_2OH$ | $4-NH_2C_6H_4SO_2$ | $i-C_4H_9$ | $4-FC_6H_4CH_2$ | $C_6H_5CH_2$ | O | 4 | 3.3 | S |
| 69 | $CH_2OH$ | $4-NH_2C_6H_4SO_2$ | $i-C_4H_9$ | $4-FC_6H_4CH_2$ | 2-Thiophene-$CH_2CH_2$ | O | 4 | 34 | S |
| 70 | $CH_2OH$ | $4-NH_2C_6H_4SO_2$ | $i-C_4H_9$ | $4-FC_6H_4CH_2$ | $C_5H_4N-3-CH_2$ | O | 4 | 30 | S |
| 71 | $CH_2OH$ | $4-NH_2C_6H_4SO_2$ | $i-C_4H_9$ | $3-FC_6H_4CH_2$ | $C_6H_{11}$ | O | 4 | 235 | S |
| 72 | $CH_2OH$ | $4-NH_2C_6H_4SO_2$ | $i-C_4H_9$ | $3-FC_6H_4CH_2$ | $C_5H_4N-3-CH_2$ | O | 4 | >300 | S |
| 73 | $CH_2OH$ | $4-NH_2C_6H_4SO_2$ | $i-C_4H_9$ | $2-FC_6H_4CH_2$ | $C_5H_4N-3-CH_2$ | O | 4 | >300 | S |
| 74 | $CH_2OH$ | $4-NH_2C_6H_4SO_2$ | $i-C_4H_9$ | H | Piperonyl | O | 4 | 22 | S |
| 75 | $CH_2OH$ | $4-NH_2C_6H_4SO_2$ | $i-C_4H_9$ | $C_4H_3S-2-CH_2$ | Piperonyl | O | 4 | 2.0 | S |
| 76 | $CH_2OH$ | $4-NH_2C_6H_4SO_2$ | $i-C_4H_9$ | $C_6H_5CH_2$ | $C_4H_3S-2-CH_2$ | O | 4 | 11 | S |
| 77 | $CH_2OH$ | $4-NH_2C_6H_4SO_2$ | $i-C_4H_9$ | H | $4-CH_3OC_6H_4CH_2$ | O | 4 | >300 | S |
| 78 | $CH_2OH$ | $4-NH_2C_6H_4SO_2$ | $i-C_4H_9$ | H | $2,6-(CH_3O)_2C_6H_3CH_2$ | O | 4 | >300 | S |
| 79 | $CH_2OH$ | $4-NH_2C_6H_4SO_2$ | $i-C_4H_9$ | H | $2,4-(CH_3O)_2C_6H_3CH_2$ | O | 4 | >300 | S |
| 80 | $CH_2OH$ | $4-NH_2C_6H_4SO_2$ | $i-C_4H_9$ | H | $3,5-(CH_3O)_2C_6H_3CH_2$ | O | 4 | >300 | S |
| 81 | $CH_2OH$ | $4-NH_2C_6H_4SO_2$ | $i-C_4H_9$ | $C_4H_3S-3-CH_2$ | Piperonyl | O | 4 | 6.3 | S |
| 82 | $CH_2OH$ | $4-NH_2C_6H_4SO_2$ | $i-C_4H_9$ | $C_6H_5CH_2$ | Piperonyl | O | 4 | 2.6 | S |
| 83 | $CH_2OH$ | $4-NH_2C_6H_4SO_2$ | $i-C_4H_9$ | $4-CH_3OC_6H_4CH_2$ | Piperonyl | O | 4 | 2.2 | S |
| 84 | $CH_2OH$ | $4-NH_2C_6H_4SO_2$ | $i-C_4H_9$ | $4-NO_2C_6H_4CH_2$ | Piperonyl | O | 4 | 2.0 | S |
| 85 | $CH_2OH$ | $4-NH_2C_6H_4SO_2$ | $i-C_4H_9$ | Piperonyl | Piperonyl | O | 4 | 1.7 | S |
| 86 | $CH_2OH$ | $4-NH_2C_6H_4SO_2$ | 3-methylbutyl | $C_6H_5CH_2$ | $C_6H_5CH_2$ | O | 4 | 5.8 | S |
| 87 | $CH_2OH$ | $4-NH_2C_6H_4SO_2$ | 3-methylbutyl | $C_4H_3S-2-CH_2$ | Piperonyl | O | 4 | 1.4 | S |
| 88 | $CH_2OH$ | $4-NH_2C_6H_4SO_2$ | 3-methylbutyl | $4-CH_3OC_6H_4CH_2$ | Piperonyl | O | 4 | 2.9 | S |
| 89 | $CH_2OH$ | $4-NH_2C_6H_4SO_2$ | 3-methylbutyl | $4-NO_2C_6H_4CH_2$ | Piperonyl | O | 4 | 2.2 | S |
| 90 | $CH_2OH$ | $4-NH_2C_6H_4SO_2$ | $i-C_4H_9$ | $4-CF_3C_6H_4CH_2$ | $2,3-(OCH_2O)C_6H_3CH_2$ | O | 4 | 8.9 | S |
| 91 | $CH_2OH$ | $4-NH_2C_6H_4SO_2$ | $i-C_4H_9$ | $C_6H_5CH_2$ | $2,3-(OCH_2O)C_6H_3CH_2$ | O | 4 | 5.4 | S |
| 92 | $CH_2OH$ | $4-NH_2C_6H_4SO_2$ | $i-C_4H_9$ | $4-CF_3C_6H_4CH_2$ | Piperonyl | O | 4 | 2.5 | S |
| 93 | $CH_2OH$ | $4-NH_2C_6H_4SO_2$ | $i-C_4H_9$ | $C_6H_5CH_2$ | $2,4-F_2C_6H_3CH_2$ | O | 4 | 12 | S |
| 94 | $CH_2OH$ | $4-NH_2C_6H_4SO_2$ | 3-methylbutyl | $4-CF_3C_6H_4CH_2$ | Piperonyl | O | 4 | 3.0 | S |
| 95 | $CH_2OH$ | $4-NH_2C_6H_4SO_2$ | 3-methylbutyl | $C_5H_4N-4-CH_2$ | Piperonyl | O | 4 | 7.1 | S |
| 96 | $CH_2OH$ | $4-NH_2C_6H_4SO_2$ | 3-methylbutyl | $C_6H_5CH_2$ | $2,3-(OCH_2O)C_6H_3CH_2$ | O | 4 | 4.0 | S |
| 97 | $CH_2OH$ | $4-NH_2C_6H_4SO_2$ | 2-methylbutyl | $C_6H_5CH_2$ | $2,3-(OCH_2O)C_6H_3CH_2$ | O | 4 | 21 | S |
| 98 | $CH_2OH$ | $4-NH_2C_6H_4SO_2$ | 2-methylbutyl | $C_6H_5CH_2$ | Piperonyl | O | 4 | 13 | S |
| 99 | $CH_2OH$ | $4-NH_2C_6H_4SO_2$ | 2-methylbutyl | $C_4H_3S-2-CH_2$ | Piperonyl | O | 4 | 24 | S |
| 100 | $CH_2OH$ | $4-NH_2C_6H_4SO_2$ | 2-methylbutyl | $4-CH_3OC_6H_4CH_2$ | Piperonyl | O | 4 | >300 | S |
| 101 | $CH_2OH$ | $4-NH_2C_6H_4SO_2$ | 3-methylbutyl | $C_6H_5CH_2$ | Piperonyl | O | 4 | 4.1 | S |
| 102 | $CH_2OH$ | $4-NH_2C_6H_4SO_2$ | 3-methylbutyl | $4-FC_5H_4CH_2$ | Piperonyl | O | 4 | 4.9 | S |
| 103 | $CH_2OH$ | $4-NH_2C_6H_4SO_2$ | 3-methylbutyl | $4-FC_6H_4CH_2$ | $3,4-(OCH_2CH_2O)C_6H_3CH_2$ | O | 4 | 5.4 | S |
| 104 | $CH_2OH$ | $4-NH_2C_6H_4SO_2$ | 3-methylbutyl | $i-C_4H_9$ | Piperonyl | O | 4 | 77 | S |
| 105 | $CH_2OH$ | $4-NH_2C_6H_4SO_2$ | 3-methylbutyl | $3-CH_3OC_6H_4CH_2$ | Piperonyl | S | 4 | 2.6 | S |
| 106 | $CH_2OH$ | $4-NH_2C_6H_4SO_2$ | 3-methylbutyl | $3,4-(CH_3O)_2C_6H_3CH_2$ | Piperonyl | S | 4 | 2.9 | S |
| 107 | $CH_2OH$ | $4-NH_2C_6H_4SO_2$ | 3-methylbutyl | $3,4,5-(CH_3O)_3C_6H_2CH_2$ | Piperonyl | S | 4 | 4.9 | S |
| 108 | $CH_2OH$ | $4-NH_2C_6H_4SO_2$ | 3-methylbutyl | $4-FC_6H_4CH_2$ | $3,4-(OCH_2CH_2O)C_6H_3CH_2$ | S | 4 | 9.9 | S |
| 109 | $CH_2OH$ | $4-NH_2C_6H_4SO_2$ | 3-methylbutyl | $4-CH_3OC_6H_4CH_2$ | Piperonyl | S | 4 | 3.6 | S |
| 110 | $CH_2OH$ | $4-NH_2C_6H_4SO_2$ | 3-methylbutyl | $3-CH_3OC_6H_4CH_2$ | Piperonyl | O | 4 | 2.2 | S |

Anti-viral and Cytotoxicity Assays in Vitro

To evaluate the $EC_{50}$ of our compounds, various drug concentrations are incubated with the infected cell for six days and then the metabolic activity of the cells is monitored by the MTT assay. (See A. J. Japour et al, Antimicrobial Agents and Chemotherapy, 37, 1095–1101, 1993 and R. Pauwels et al. Journal of Virological Methods, 20, 309–321, 1988).

We use the laboratory viral strain NL4.3 as wild type virus and the cell line used is MT-4 which is a T-cell line highly sensitive to HIV-1. We also use some WT clinical strains. To address the resistance issue we assay the inhibitors with NL4.3 mutants which are designed to be resistant to specific commercially available inhibitors.

The same MTT assay is used to evaluate the $CCIC_{50}$ (cell culture $IC_{50}$) of our compounds except that the virus is omitted.

Table 2 presents the anti-viral and the cytotoxic activities of selected compounds illustrating their potential usefulness.

TABLE 2

Anti-viral and cytotoxic activity of Nε-amino carbonyl substituted L-Lysinol derivatives.

| Example No. | $EC_{50}$ (nM)* | $CCIC_{50}$ (nM)* |
|---|---|---|
| 59 | 385 | 4600 |
| 60 | 1800 | 4600 |

TABLE 2-continued

Anti-viral and cytotoxic activity of Nε-amino carbonyl substituted L-Lysinol derivatives.

| Example No. | EC$_{50}$ (nM)* | CCIC$_{50}$ (nM)* |
|---|---|---|
| 61 | 3800 | 5100 |
| 67 | 488 | 11000 |
| 82 | 1400 | 12500 |
| 85 | 130 | 13100 |
| 95 | 550 | 28800 |
| 102 | 1200 | 24400 |
| 107 | 680 | 10700 |
| 110 | 350 | ND |

*Average of at least two determinations

We claim:

1. A compound of formula I

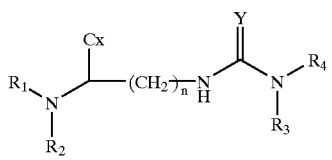

I and when the compound of formula I comprises an amino group, pharmaceutically acceptable ammonium salts thereof, wherein n is 3, 4 or 5, wherein Y is O, S, NH or N—CN, wherein Cx is selected from the group consisting of —COOM, —COOR$_5$, and —CH$_2$OR$_6$ wherein M is selected from the group consisting of alkali metals and alkaline earth metals, wherein R$_1$ is a benzenesulfonyl group of formula II

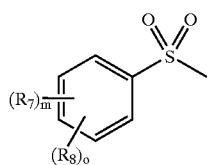

II wherein R$_2$ is selected from the group consisting of a straight alkyl group of 1 to 6 carbon atoms, a branched alkyl group of 3 to 6 carbon atoms, and a cycloalkylalkyl group having 3 to 6 carbon atoms in the cycloalkyl part thereof and 1 to 3 carbon atoms in the alkyl part thereof, wherein R$_3$ is selected from the group consisting of H, a straight alkyl group of 1 to 6 carbon atoms, a branched alkyl group of 3 to 6 carbon atoms, a piperonyl group, a phenyl group, a picolyl group selected from the group consisting of

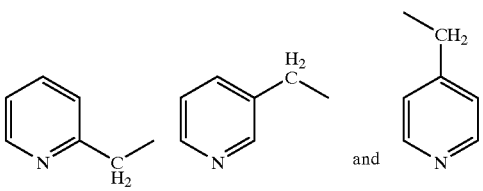

a thiophene group selected from the group consisting of

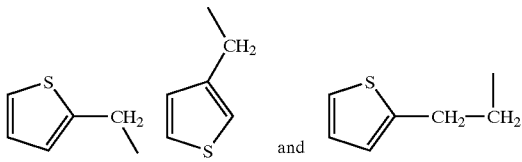

and a benzyl group of formula III

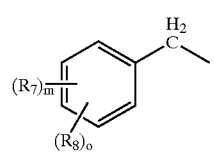

III wherein R$_4$ is selected from the group consisting of a straight alkyl group of 1 to 6 carbon atoms, a branched alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl, (S)-2-hydroxy-1-indanyl, 1-isoquinolyl, 2-quinolyl, a group of formula IIIa

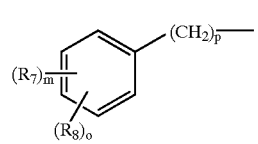

IIIa a picolyl group selected from the group consisting of

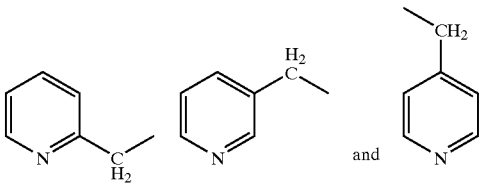

thiophene group selected from the group consisting of

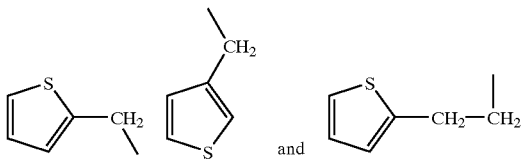

a group selected from the group consisting of

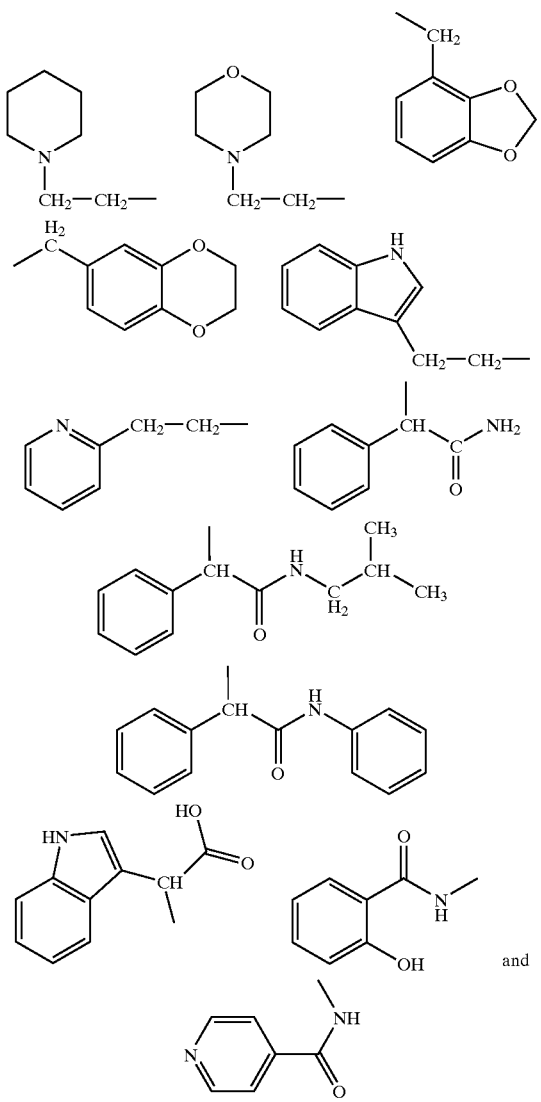

wherein $R_5$ is selected from the group consisting of H, a straight alkyl group of 1 to 4 carbon atoms and a branched alkyl group of 3 or 4 carbon atoms, wherein $R_6$ is selected from the group consisting of H, a straight alkyl group of 1 to 4 carbon atoms and a branched alkyl group of 3 or 4 carbon atoms, wherein $R_7$ and $R_8$, same or different, are selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$, wherein $R_9$ and $R_{10}$, same or different, are selected from the group consisting of H, a straight alkyl group of 1 to 4 carbon atoms and a branched alkyl group of 3 or 4 carbon atoms, wherein m is 0 or 1, wherein o is 0, 1 or 2, wherein p is 0, 1 or 2.

2. A compound of formula IA

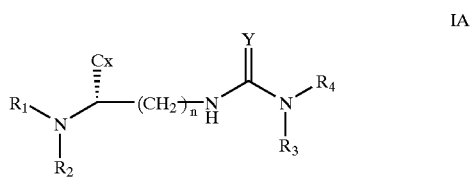

and when the compound of formula IA comprises an amino group, pharmaceutically acceptable ammonium salts thereof, wherein n is 3, 4 or 5, wherein Y is O, S, NH or N—CN, wherein Cx is selected from the group consisting of —COOM, —$COOR_5$, and —$CH_2OR_6$ wherein M is selected from the group consisting of alkali metals and alkaline earth metals, wherein $R_1$ is a benzenesulfonyl group of formula II

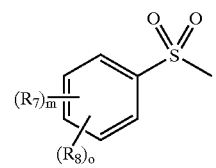

wherein $R_2$ is selected from the group consisting of a straight alkyl group of 1 to 6 carbon atoms, a branched alkyl group of 3 to 6 carbon atoms, and a cycloalkylalkyl group having 3 to 6 carbon atoms in the cycloalkyl part thereof and 1 to 3 carbon atoms in the alkyl part thereof, wherein $R_3$ is selected from the group consisting of H, a straight alkyl group of 1 to 6 carbon atoms, a branched alkyl group of 3 to 6 carbon atoms, a piperonyl group, a phenyl group, a picolyl group selected from the group consisting of

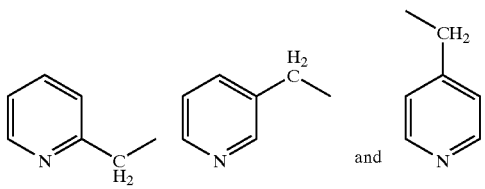

a thiophene group selected from the group consisting of

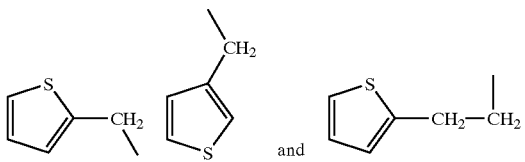

and a benzyl group of formula III

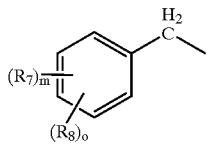

III wherein R₄ is selected from the group consisting of a straight alkyl group of 1 to 6 carbon atoms, a branched alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl, (S)-2-hydroxy-1-indanyl, 1-isoquinolyl, 2-quinolyl, a group of formula IIIa

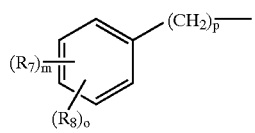

IIIa a picolyl group selected from the group consisting of

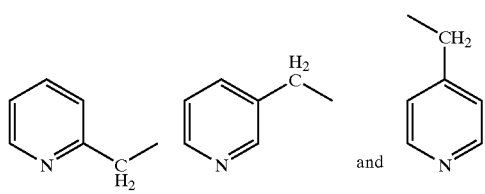

a thiophene group selected from the group consisting of

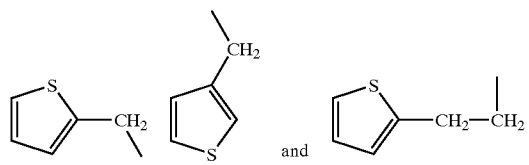

a group selected from the group consisting of

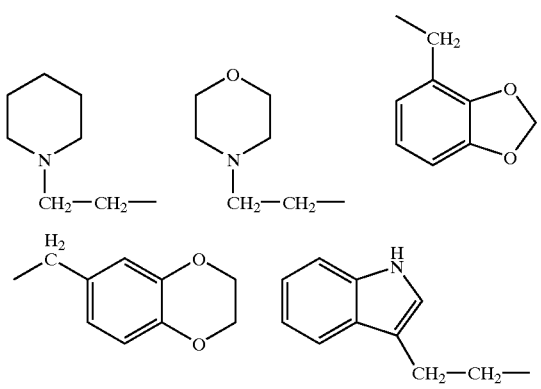

-continued

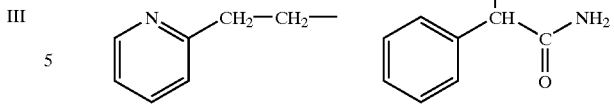

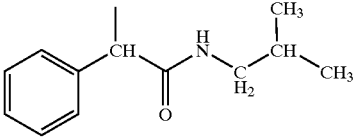

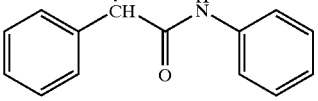

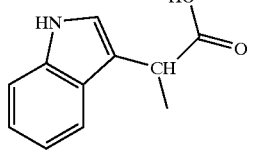 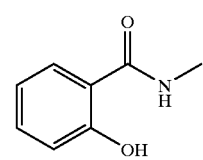 and

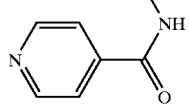

wherein $R_5$ is selected from the group consisting of H, a straight alkyl group of 1 to 4 carbon atoms and a branched alkyl group of 3 or 4 carbon atoms, wherein $R_6$ is selected from the group consisting of H, a straight alkyl group of 1 to 4 carbon atoms and a branched alkyl group of 3 or 4 carbon atoms, wherein $R_7$ and $R_8$, same or different, are selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$, wherein $R_9$ and $R_{10}$, same or different, are selected from the group consisting of H, a straight alkyl group of 1 to 4 carbon atoms, and a branched alkyl group of 3 or 4 carbon atoms, wherein m is 0 or 1, wherein o is 0, 1 or 2, wherein p is 0, 1 or 2.

3. A compound as defined in claim 2, wherein Cx is —$CO_2H$, Y is O and n is 4.

4. A compound as defined in claim 2, wherein Cx is —$CH_2OH$, Y is O and n is 4.

5. A compound as defined in claim 3, wherein $R_2$ is iso-butyl.

6. A compound as defined in claim 4, wherein $R_2$ is selected from the group consisting of iso-butyl, 2-methylbutyl and 3-methylbutyl.

7. A compound as defined in claim 2, wherein Cx is —$CO_2H$, Y is S and n is 4.

8. A compound as defined in claim 2, wherein Cx is —$CH_2OH$, Y is S and n is 4.

9. A compound as defined in claim 3, wherein $R_1$ is selected from the group consisting of 4-$CH_3C_6H_4SO_2$— and 4-$NH_2C_6H_4SO_2$— and $R_2$ is iso-butyl.

10. A compound as defined in claim 4, wherein $R_1$ is selected from the group consisting of 4-$CH_3C_6H_4SO_2$— and 4-$NH_2C_6H_4SO_2$— and $R_2$ is iso-butyl.

11. A compound as defined in claim 4, wherein $R_1$ is 4-$NH_2C_6H_4SO_2$— and $R_2$ is selected from the group consisting of 2-methylbutyl and 3-methylbutyl.

12. A compound as defined in claim 5, wherein $R_1$ is selected from the group consisting of 4-$CH_3C_6H_4SO_2$— and 4-$NH_2C_6H_4SO_2$—.

13. A compound as defined in claim 7, wherein $R_1$ is 4-$CH_3C_6H_4SO_2$— and $R_2$ is iso-butyl.

14. A compound of formula Ia

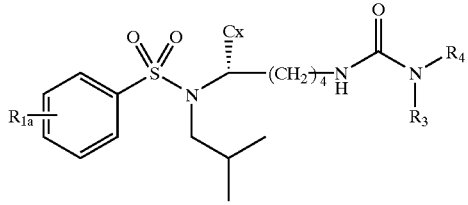

Ia and when the compound of formula Ia comprises an amino group, pharmaceutically acceptable ammonium salts thereof, wherein Cx is selected from the group consisting of —COOM, —COOH and —$CH_2OH$, wherein M is selected from the group consisting of alkali metals and alkaline earth metals, wherein $R_{1a}$ is selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$—, —$NHCOR_9$, —$OR_9$, —$SR_9$, —$COOR_9$, —$COR_9$ and —$CH_2OH$, wherein $R_3$ is selected from the group onsisting of H, a straight alkyl group of 1 to 6 carbon ators, a branched alkyl group of 3 to 6 carbon atoins, a piperonyl group, a phenyl group, a picolyl group selected from the group consisting of

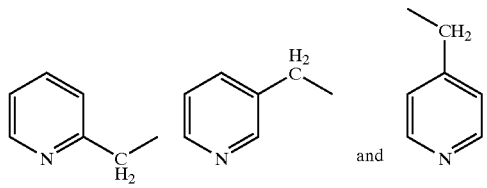

a thiophene group selected from the group consisting of

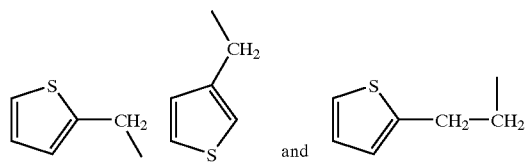

and a benzyl group of formula III

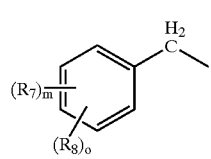

III wherein $R_4$ is selected from the group consisting of a straight alkyl group of 1 to 6 carbon atoms, a branched alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl (S)-2-hydroxy-1-indanyl, 1-isoquinolyl, 2-quinolyl, a group of formula IIIa

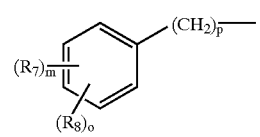

IIIa a picolyl group selected from the group consisting of

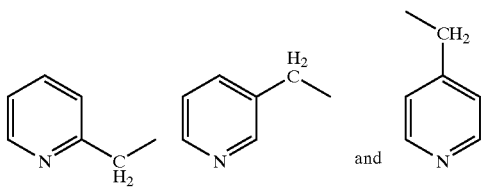

a thiophene group selected from the group consisting of

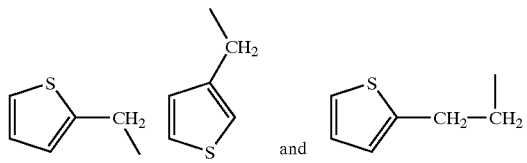

a group selected from the group consisting of

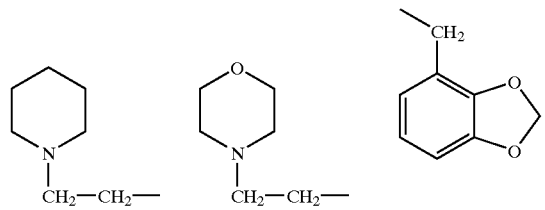

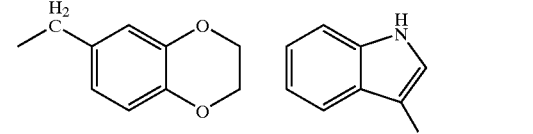

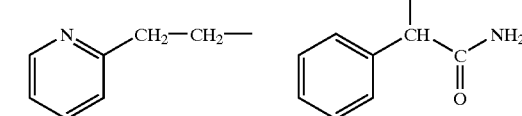

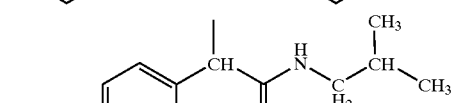

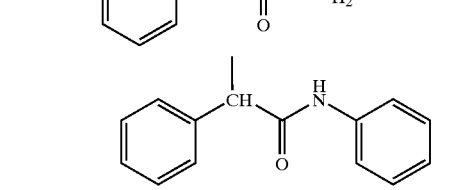

-continued

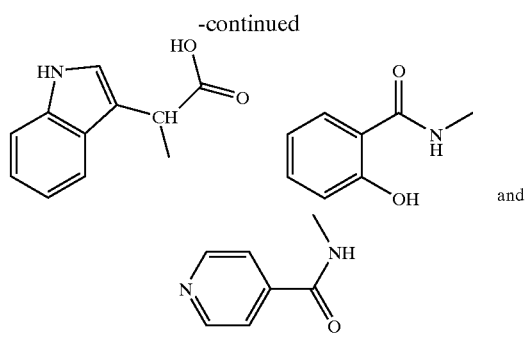

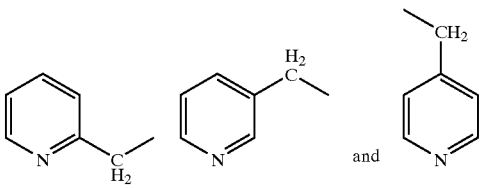

and wherein $R_7$ and $R_8$, same or different, are selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$, wherein $R_9$ and $R_{10}$, same or different, are selected from the group consisting of H, a straight alkyl group of 1 to 4 carbon atoms and a branched alkyl group of 3 or 4 carbon atoms, wherein m is 0 or 1, wherein o is 0, 1 or 2, and wherein p is 0, 1 or 2.

15. A compound as defined in claim 14, wherein $R_3$ is a group selected from the group consisting of

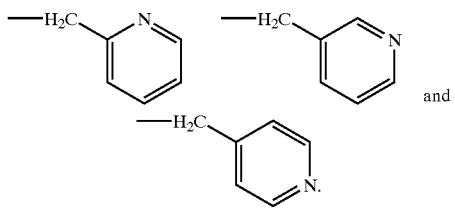

and

16. A compound as defined in claim 14, wherein $R_3$ is a group of formula IV

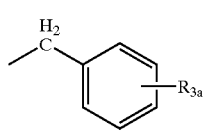

IV wherein $R_{3a}$ is selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$.

17. A compound of formula Ib

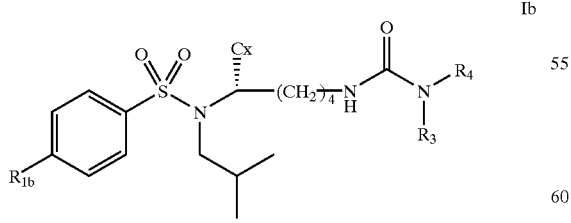

Ib and when the compound of formula Ib comprises an amino group, pharmaceutically acceptble ammonium salts thereof, wherein Cx is selected from the group consisting of —COOM, —COOH and —$CH_2OH$, wherein M is selected from the group consisting of alkali metals and alkaline earth metals, wherein $R_{1b}$ is selected from the group consisting of H, a straight alkyl group of 1 to 4 carbon atoms, a branched alkyl group of 3 or 4 carbon atoms, P, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$, wherein $R_3$ is selected from the group consisting of H, a straight alkyl group of 1 to 6 carbon atoms, a branched alkyl group of 3 to 6 carbon atoms, a piperonyl group, a phenyl group, a picolyl group selected from the group consisting of

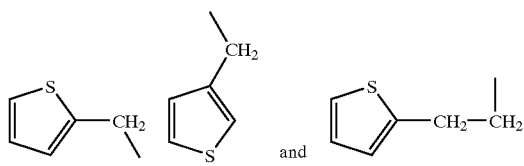

and a thiopene group selected from the group consisting of

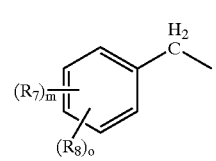

and and a benzyl group of formula III

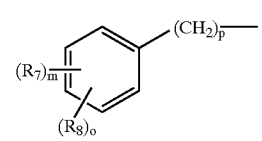

III wherein $R_4$ is selected from the group consisting of a straight alkyl group of 1 to 6 carbon atoms a branched alkyl group of 3 to 6 carbon atoms, a cycloalkyl group having 3 to 6 carbon, a piperonyl (i.e. 3,4-ethylenedioxybenzyl) group, 1-indanyl, (R)-2-hydroxy-1-indanyl, (S)-2-hydroxy-1-indanyl, 1-isoquinolyl, 2-quinolyl, a group of formula IIIa

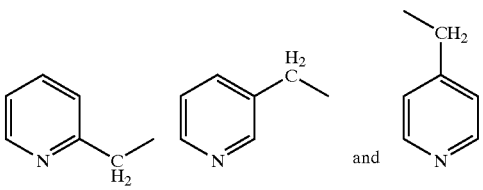

IIIa a picolyl group selected from the group consisting of a thiophene group selected from the group consisting of

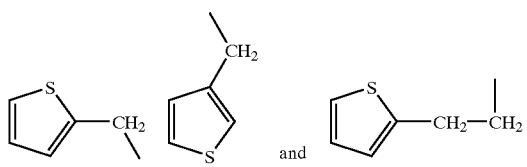

and a group selected from the group consisting of

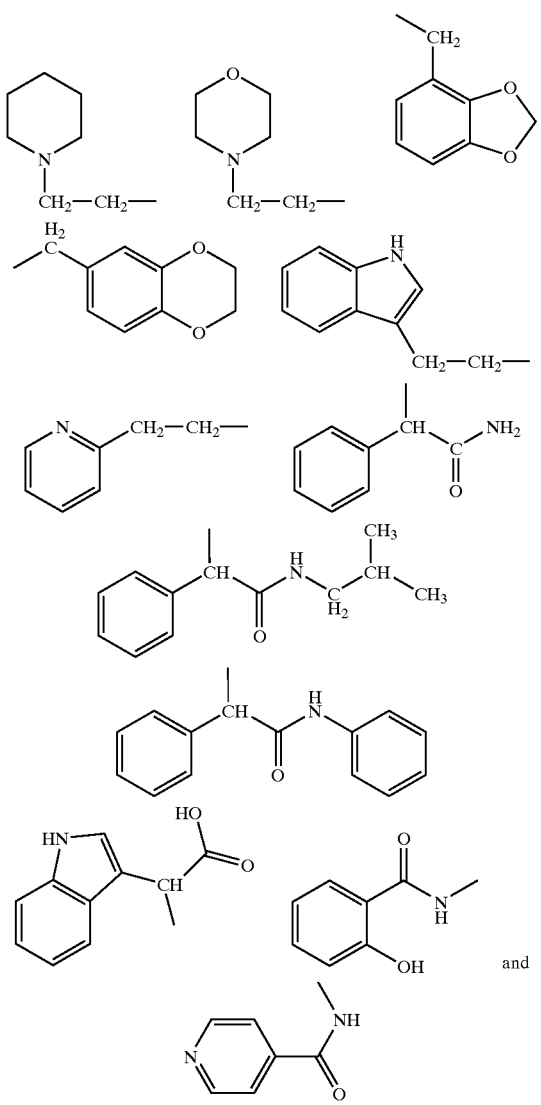

wherein $R_7$ and $R_8$, same or different are selected from the group consisting of H, a straight alkyl group of 1 to 4 carbon atoms, a branched alkyl group of 3 or 4 carbon atoms, F, Cl, Br, I, —$CF_3$, —$NO_2$, —$NR_9R_{10}$, —$NHCOR_9$, —$OR_9$, —$SR_9$, —$COOR_9$, —$COR_9$ and —$CH_2OH$, wherein $R_9$ and $R_{10}$, same or different, are selected from the group consisting of H, a straight alkyl group of 1 to 4 carbon atoms and a branched alkyl group of 3 or 4 carbon atoms, wherein m is 0 or 1, wherein o is 0, 1 or 2, and wherein p is 0, 1 or 2.

18. A compound as defined in claim 17, wherein Cx is selected from the group consisting of —COOH and —COOM, wherein M is selected from the group consisting of Na, K and Cs.

19. A compound as defined in claim 17, wherein Cx is —$CH_2OH$.

20. A compound as defined in claim 18, wherein $R_{1b}$ is —$NH_2$, $R_3$ is benzyl and $R_4$ is benzyl.

21. A compound as defined in claim 18, wherein $R_{1b}$ is —$CH_3$, $R_3$ is a group of formula

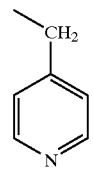

and $R_4$ is benzyl.

22. A compound as defined in claim 18, wherein $R_{1b}$ is —$CH_3$, $R_3$ is a group of formula

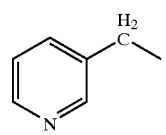

and $R_4$ is benzyl.

23. A compound as defined in claim 18, wherein $R_{1b}$ is —$NH_2$, $R_3$ is a group of formula

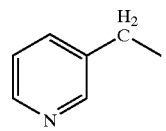

and $R_4$ is benzyl.

24. A compound as defined in claim 18, wherein $R_{1b}$ is —$CH_3$, $R_3$ is benzyl, and $R_4$ is a group of formula

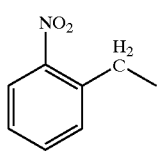

25. A compound as defined in claim 18, wherein $R_{1b}$ is —$CH_3$, $R_3$ is benzyl and $R_4$ is a group of formula

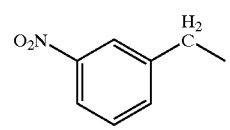

26. A compound as defined in claim 18, wherein $R_{1b}$ is —$CH_3$, $R_3$ is benzyl and $R_4$ is a group of formula

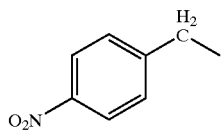

27. A compound as defined in claim 18, wherein $R_{1b}$ is —CH$_3$, $R_3$ is benzyl and $R_4$ is a group of formula

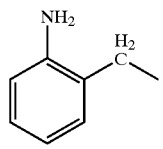

28. A compound as defined in claim 19, wherein $R_{1b}$ is —CH$_3$, $R_3$ is benzyl, and $R_4$ is a group of formula

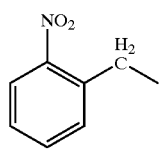

29. A compound as defined in claim 19, wherein $R_{1b}$ is —NH$_2$, $R_3$ is piperonyl and $R_4$ is a group of formula

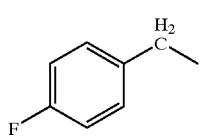

30. A compound as defined in claim 19, wherein $R_{1b}$ is —NH$_2$, $R_3$ is benzyl, $R_4$ is a group of formula

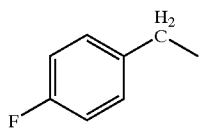

31. A compound as defined in claim 19, wherein $R_{1b}$ is —NH$_2$, $R_3$ is a group of formula

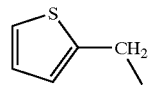

and $R_4$ is piperonyl.

32. A compound as defined in claim 19, wherein $R_{1b}$ is —CH$_3$, $R_3$ is benzyl, and $R_4$ is a group of formula

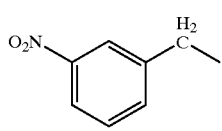

33. A compound as defined in claim 19, wherein $R_{1b}$ is —CH$_3$, $R_3$ is benzyl, and $R_4$ is a group of formula

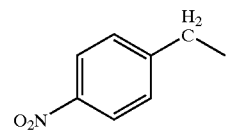

34. A compound as defined in claim 19, wherein $R_{1b}$ is —NH$_2$, $R_3$ is benzyl and $R_4$ is piperonyl.

35. A compound as defined in claim 19, wherein $R_{1b}$ is —NH$_2$, $R_3$ is a group of formula

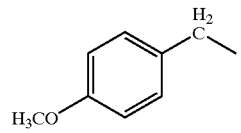

and $R_4$ is piperonyl.

36. A compound as defined in claim 19, wherein $R_{1b}$ is —NH$_2$, $R_3$ is a group of formula

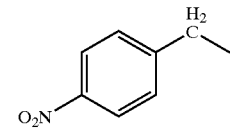

and $R_4$ is piperonyl.

37. A compound as defined in claim 19, wherein $R_{1b}$ is —NH$_2$, $R_3$ is piperonyl and $R_4$ is piperonyl.

38. A compound as defined in claim 19 wherein $R_{1b}$ is —NH$_2$, $R_3$ is a group of formula

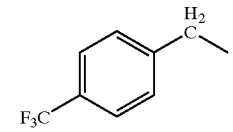

and $R_4$ is piperonyl.

39. A compound of formula Ic

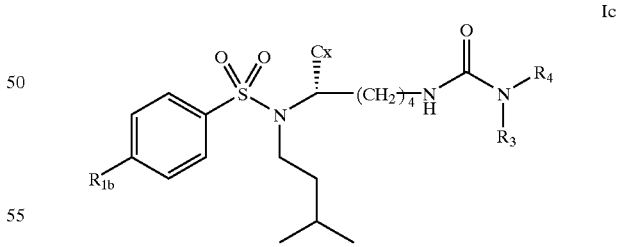

and when the compound of formula Ic comprises an amino group, pharmaceutically acceptable ammonium salts thereof, wherein Cx is selected from the group consisting of —COOM, —COOH and —CH$_2$OH, wherein M is selected from the group consisting of alkali metals and alkaline earth metals, wherein $R_{1b}$ is selected from the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, wherein R$_3$ is selected from the group consisting of H, a straight alkyl group of 1 to 6 carbon atoms, a branched alkyl group of 3 to 6 carbon atoms, a piperonyl group, a phenyl group, a picolyl group selected from the group consisting of

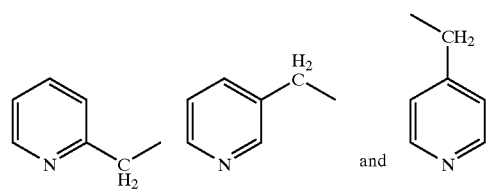

a thiophene group selected from the group consisting of

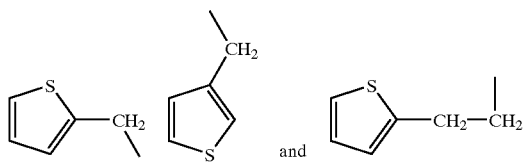

and a benzyl group of formula III

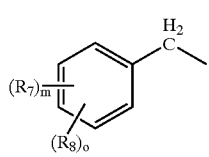

III wherein R$_4$ is selected from the group consisting of a straight alkyl group of 1 to 6 carbon atoms, a branched alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl, (S)-2-hydroxy-1-indanyl, 1-isoquinolyl, 2-quinolyl, a group of formula IIIa

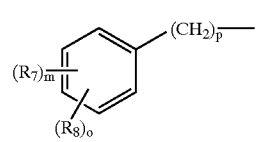

IIIa a picolyl group selected from the group consisting of

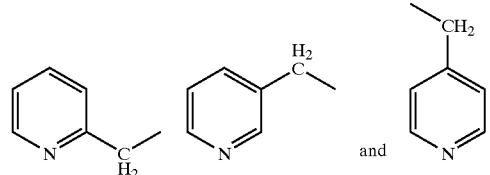

a thiophene group selected from the group consisting of

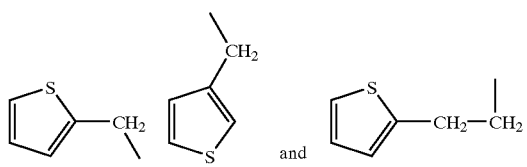

a group selected from group consisting of

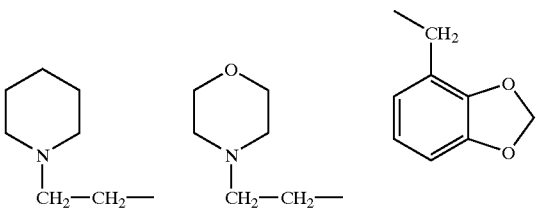

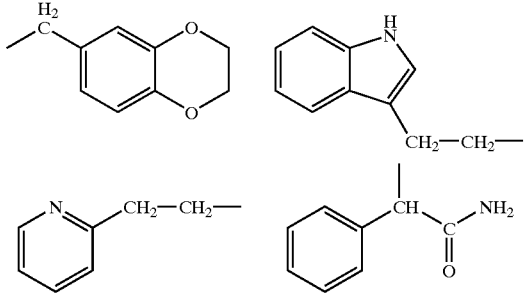

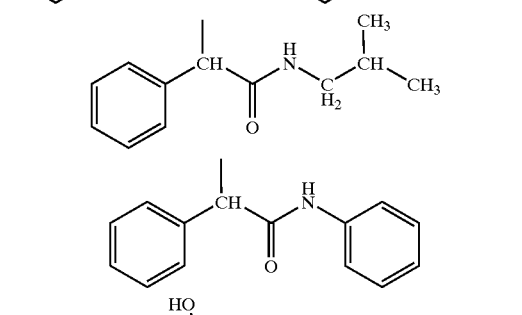

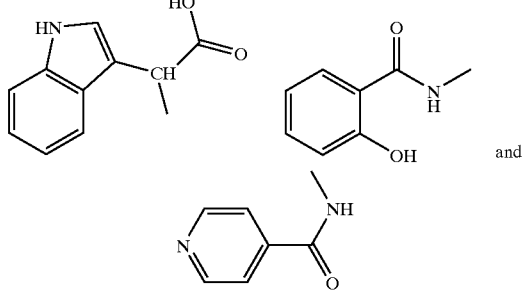

and wherein R$_7$ and R$_8$, same or different, are selected fron the group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH.

wherein R$_9$ and R$_{10}$, same or different, are selected from the group consisting of H, a straight alkyl group of 1 to 4 carbon atoms and a branched alkyl group of 3 or 4 carbon atoms, wherein m is 0 or 1, wherein o is 0, 1 or 2, and wherein p is 0, 1 or 2.

40. A compound as defined in claim 39, wherein Cx is —CH$_2$OH.

41. A compound as defined in claim 40, wherein R$_{1b}$ is —NH$_2$, R$_3$ is a group of formula

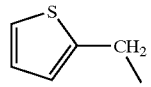

and R$_4$ is piperonyl.

42. A compound of as defined in claim 40, wherein R$_{1b}$ is —NH$_2$, R$_3$ is a group of formula

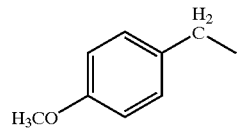

and R$_4$ is piperonyl.

43. A compound as defined in claim 40, wherein R$_{1b}$ is —NH$_2$, R$_3$ is a group of formula

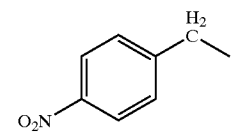

and R$_4$ is piperonyl.

44. A compound as defined in claim 40, wherein R$_{1b}$ is —NH$_2$, R$_3$ is a group of formula

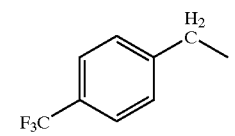

and R$_4$ is piperonyl.

45. A compound as defined in claim 40, wherein R$_{1b}$ is —NH$_2$, R$_3$ is a group of formula

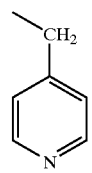

and R$_4$ is piperonyl.

46. A compound as defined in claim 40, wherein R$_{1b}$ is —NH$_2$, R$_3$ is benzyl and R$_4$ is a group of formula

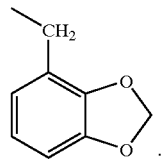

47. A compound as defined in claim 40, wherein R$_{1b}$ is —NH$_2$, R$_3$ is benzyl and R$_4$ is piperonyl.

48. A compound as defined in claim 40, wherein R$_{1b}$ is —NH$_2$, R$_3$ is a group of formula

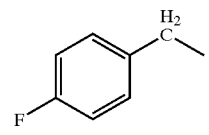

and R$_4$ is piperonyl.

49. A compound as defined in claim 40, wherein R$_{1b}$ is —NH$_2$, R$_3$ is a group of formula

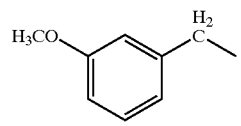

and R$_4$ is piperonyl.

50. A compound of formula Id

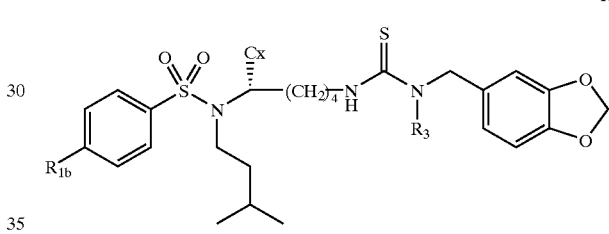

and when the compound of formula Id comprises an amino group, pharmaceutically acceptable ammonium salts thereof, wherein Cx is selected from the group consisting of —COOM, —COOH and —CH$_2$OH, wherein M is selected from the group consisting of alkali metals and alkaline earth metals, wherein R$_{1b}$ is selected from fe group consisting of H, a straight alkyl group of 1 to 4 carbon atoms, a branched alkyl group of 3 or 4 carbon atoms, F, Cl, Br, I, —CF$_3$, —NO$_2$, —NR$_9$R$_{10}$, —NHCOR$_9$, —OR$_9$, —SR$_9$, —COOR$_9$, —COR$_9$ and —CH$_2$OH, wherein R$_3$ is selected from the group consisting of H, a straight alkyl group of 1 to 6 carbon atoms, a branched alyl group of 3 to 6 carbon atoms, a piperonyl group, a phenyl group, a picolyl group selected from the group consisting of

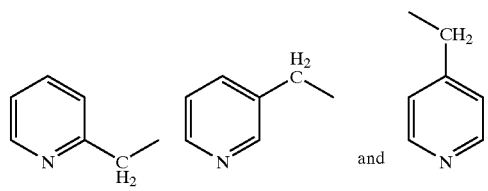

a thiophene group selected fom the group consisting of

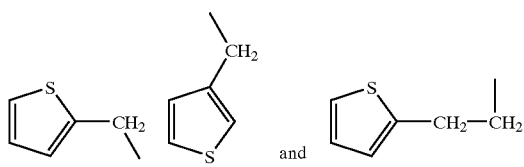

and a benzyl group of formula III

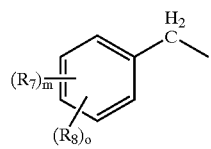    III wherein R₄ is selected from the group consisting of a straight alkyl group of 1 to 6 carbon atoms, a branch alkyl group of 3 to 6 carbon atoms, a cycloalkyl group having 3 to 6 carbon, a piperonyl (i.e. 3,4-methylenedioxybenzyl) group, 1-indanyl, (R)-2-hydroxy-1-indanyl, (S)-2-hydroxy-1-indanyl, 1-isoquinolyl, 2-quniolyl, a group of formula IIIa

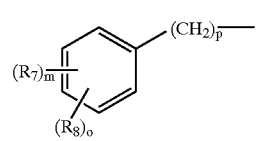    IIIa a picolyl group selected from the group consisting of

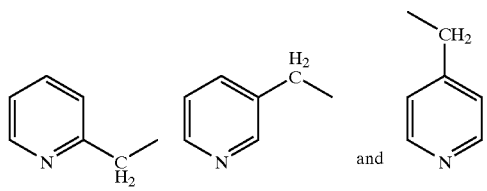

a thiophene group selected from the group consisting of

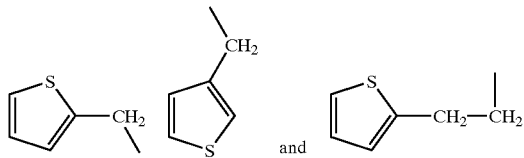

a group selected from the group consisting of

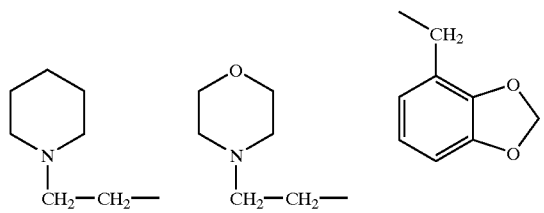

-continued

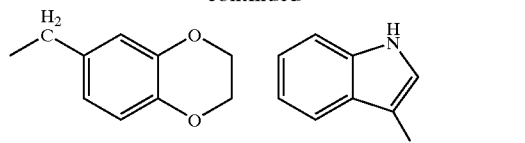

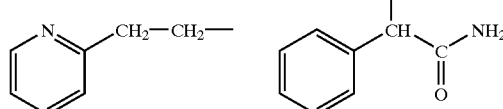

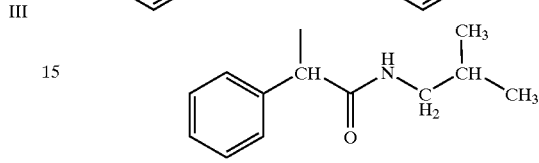

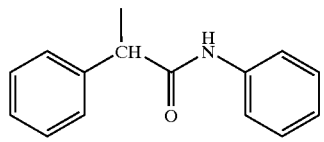

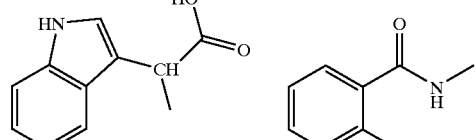

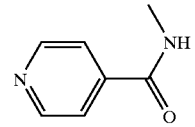

wherein $R_7$ and $R_8$, same or different, are selected from the group consisting of H, a straight alkyl group of 1 to 4 carbon atoms, a branched akyl group of 3 or 4 carbon atoms, F, Cl, Br, I, —CF₃, —NO₂, —NR₉R₁₀, —NHCOR₉, —OR₉, —SR₉, —COOR₉, —COR₉ and —CH₂OH, wherein $R_9$ and $R_{10}$, same or different, are selected from the group consisting of H, a straight alkyl group of 1 to 4 carbon atoms and a branched alkyl group of 3 or 4 carbon atoms, wherein m is 0 or 1, wherein o is 0, 1 or 2, and where p is 0, 1 or 2.

51. A compound as defined in claim 50, wherein Cx is —CH₂OH.

52. A compound as defined in claim 51, wherein $R_{1b}$ is —NH₂ and $R_3$ is a group of formula

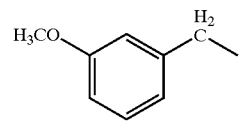

53. A compound as defined in claim 51, wherein $R_{1b}$ is —NH₂ and $R_3$ is a group of formula

54. A compound as defined in claim 51, wherein $R_{1b}$ is —$NH_2$ and $R_3$ is a group of formula

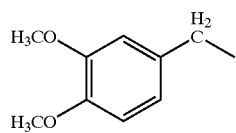

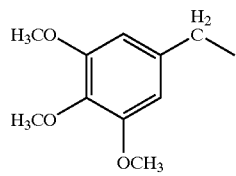

55. A compound as defined in claim 51, wherein $R_{1b}$ is —$NH_2$ and $R_3$ is a group of formula

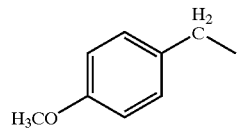

56. A pharmaceutical composition comprising a pharmaceutically acceptable carrier and at least one compound as defined in claim 1.

57. A pharmaceutical composition comprising a pharmaceutically acceptable carrier and at least one compound as defined in claim 2.

* * * * *

UNITED STATES PATENT AND TRADEMARK OFFICE
CERTIFICATE OF CORRECTION

PATENT NO. : 6,528,532 B1
DATED : March 4, 2003
INVENTOR(S) : Brent Richard Stranix et al.

It is certified that error appears in the above-identified patent and that said Letters Patent is hereby corrected as shown below:

Column 26,
Line 49, the phrase " ...similar to HW..." should read -- similar to HIV... --;

Column 45,
Line 61, the phrase " ...Nω)-benzyl-DL-homoarginine..." should read
-- " ...Nω- benzyl-DL-homoarginine...--;

Column 52,
Line 58, the phrase "...-Nε-N'-(2-ninobenzyl)-..." should read -- "...-Nε-N'-(2-aminobenzyl)-... --;

Column 55,
Line 53, the phrase "a solution of LiAlH..." should read -- a solution of LiAlH$_4$... --;

Column 60,
Line 7, the phrase "...2-N-(4-anobenzenesulfonyl)-..." should read
-- ...2-N-(4-aminobenzenesulfonyl)-...--;

Column 83,
Line 22, the phrase "...phannaceutically acceptable..." should read
-- ..pharmaceutically acceptable... --;
Line 32, the phrase "...selected from the group onsisting of..." should read
-- ...selected from the group consisting of... --;
Line 34, the phrase "... 3 to 6 carbon atoins..." should read -- ... 3 to 6 carbon atoms... --;

Column 86,
Line 3, the phrase "... ,P, Cl, Br, I,..." should read -- ... , F, Cl, Br, I, ... --;

UNITED STATES PATENT AND TRADEMARK OFFICE
CERTIFICATE OF CORRECTION

PATENT NO. : 6,528,532 B1
DATED : March 4, 2003
INVENTOR(S) : Brent Richard Stranix et al.

It is certified that error appears in the above-identified patent and that said Letters Patent is hereby corrected as shown below:

<u>Column 94,</u>
Line 48, the phrase "… from fe group…" should read -- … from the group… --.

Signed and Sealed this

Tenth Day of August, 2004

JON W. DUDAS
*Acting Director of the United States Patent and Trademark Office*